(12) United States Patent
Berezovski et al.

(10) Patent No.: US 9,644,202 B2
(45) Date of Patent: May 9, 2017

(54) SWITCHABLE APTAMERS

(71) Applicant: University of Ottawa, Ottawa (CA)

(72) Inventors: Maxim V. Berezovski, Ottawa (CA); Mohamed Wehbe, Ottawa (CA); Mahmoud Aziz Mahmoud Labib, Ottawa (CA); Darija Muharemagic, Gatineau (CA); Anna S. Zamay, Krasnoyarsk (RU); Shahrokh Ghobadloo, Ottawa (CA)

(73) Assignee: University of Ottawa, Ottawa (CA)

( * ) Notice: Subject to any disclaimer, the term of this patent is extended or adjusted under 35 U.S.C. 154(b) by 99 days.

(21) Appl. No.: 14/277,110

(22) Filed: May 14, 2014

(65) Prior Publication Data
US 2014/0342918 A1 Nov. 20, 2014

Related U.S. Application Data

(60) Provisional application No. 61/823,638, filed on May 15, 2013.

(51) Int. Cl.
| | |
|---|---|
| C12Q 1/68 | (2006.01) |
| C12N 15/10 | (2006.01) |
| C07K 1/14 | (2006.01) |
| C12N 7/00 | (2006.01) |
| C12N 15/115 | (2010.01) |
| C12N 15/11 | (2006.01) |

(52) U.S. Cl.
CPC ............ *C12N 15/1048* (2013.01); *C07K 1/14* (2013.01); *C12N 7/00* (2013.01); *C12N 15/111* (2013.01); *C12N 15/115* (2013.01); *C12N 2310/16* (2013.01); *C12N 2320/13* (2013.01); *C12N 2760/20051* (2013.01); *C12N 2760/20251* (2013.01)

(58) Field of Classification Search
CPC ...................................................... C12Q 1/68
See application file for complete search history.

(56) References Cited

PUBLICATIONS

Deng et al. (Journal of Chromatography A, 1005 (2003) 123-130).*
Ayyar, B. V.; Arora, S.; Murphy, C.; O'Kennedy, R. Methods 2012, 56, 116.
Berezovski MV, Lechmann M, Musheev MU, Mak TW, Krylov SN. "Aptamer-facilitated biomarker discovery (AptaBiD)" J Am Chem Soc. Jul. 16, 2008;130(28):9137-43.
Carrasquilla C, Li Y, Brennan JD. Surface immobilization of structure-switching DNA aptamers on macroporous sol gel-derived films for solid-phase biosensing applications. Anal Chem. Feb. 1, 2011;83(3):957-65).
Darfeuille, F.; S. Reigadas, J. Hansen, H. Orum, C. Di Primo, J. Toulme (2006). "Aptamers targeted to an RNA hairpin show improved specificity compared to that of complementary oligonucleotides" Biochemistry 45: 12076-12082.
Deng QP, Tie C, Zhou YL, Zhang XX, Cocaine detection by structure-switch aptamer-based capillary zone electrophoresis, Electrophoresis. May 2012;33(9-10):1465-70.
Diallo, J.; Vähä-Koskela, M.; Le Boeuf, F.; Bell, J. Methods in Molecular Biology 2012, 127.
Fitzgerald, J.; Leonard, P.; Darcy, E.; O'Kennedy, R. Methods Mol Biol 2011, 681, 35.
Jeong, S.; S.R. Han, Y.J. Lee, S.W. Lee (2010). "Selection of RNA aptamers specific to active prostate-specific antigen." Biotechnology Letters 32: 379-85.
Liu, M.; T. Kagahara, H. Abe, Y. Ito (2009). "Direct In Vitro Selection of Hemin-Binding DNA Aptamer with Peroxidase Activity". Bulletin of the Chemical Society of Japan 82: 99-104.
Long, S.; M. Long, R. White, B. Sullenger (2008). "Crystal structure of an RNA aptamer bound to thrombin". RNA 14(2): 2504-2512.
Min, K.; M. Cho, S. Han, Y. Shim, J. Ku, C. Ban (2008). "A simple and direct electrochemical detection of interferon-gamma using its RNA and DNA aptamers." Biosensors & Bioelectronics 23: 1819-1824.
Ng E.W.M; D.T. Shima, P. Calias, E.T. Cunningham, D.R. Guyer, A.P. Adamis (2006). "Pegaptanib, a targeted anti-VEGF aptamer for ocular vascular disease." Nature Reviews Drug Discovery 5 (2): 123-132.
Potty, A.; K. Kourentzi, H. Fang, G. Jackson, X. Zhang, G. Legge, R. Willson (2009). Biophysical Characterization of DNA Aptamer Interactions with Vascular Endothelial Growth Factor, Biopolymers 91: 145-156.
Romig TS, Bell C, Drolet DW. J Chromatogr B Biomed Sci Appl. Aug. 20, 1999;731(2):275-84.
Savory, N.; K. Abe, K. Sode, K. Ikebukuro (2010). "Selection of DNA aptamer against prostate specific antigen using a genetic algorithm and application to sensing." Biosensors & Bioelectronics 15: 1386-91.
Sefah et al. (Sefah K, Phillips JA, Xiong X, Meng L, Van Simaeys D, Chen H, Martin J, Tan W. Nucleic acid aptamers for biosensors and bio-analytical applications. Analyst. Sep. 2009;134(9):1765-75.
Wei, S.; Mizaikoff, B. J Sep Sci 2007, 30, 1794.
Yang, H.; Gurgel, P. V.; Carbonell, R. G. J Chromatogr A 2009, 1216, 910.
Zhu Z, Ravelet C, Perrier S, Guieu V, Roy B, Perigaud C, Peyrin E. Multiplexed detection of small analytes by structure-switching aptamer-based capillary electrophoresis. Anal Chem. Jun. 1, 2010;82(11):4613-20.
Jiang, Y.; Fang, X.; Bai, a. C. Analytical Chemistry 2004, 5230.

* cited by examiner

*Primary Examiner* — Kimberly Chong
(74) *Attorney, Agent, or Firm* — Stradley Ronon Stevens & Young, LLP

(57) ABSTRACT

The disclosure relates to a switchable aptamer having a high affinity for a selected target such as a virus, cell or antibody when in the presence of a binding ion and a low affinity for said target in the absence of said binding ion. The switchable aptamer may be isolated from a pool comprising a mixture of aptamers by incubating the pool with the target ligand and a binding ion to form target-aptamer complexes; separating unbound aptamer molecules from the target-aptamer complexes; contacting the target-aptamer complexes with a chelating agent having affinity for the binding ion wherein a switchable aptamer specific to said target is released from the target-aptamer complexes; and isolating the switchable aptamer released in the preceding step.

14 Claims, 71 Drawing Sheets

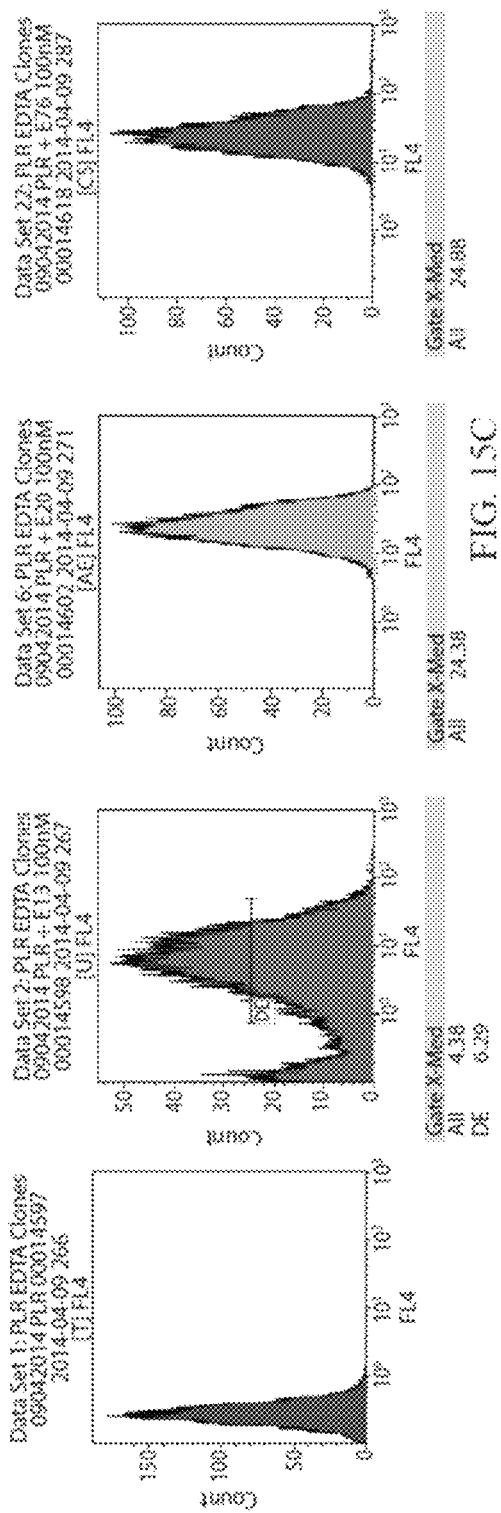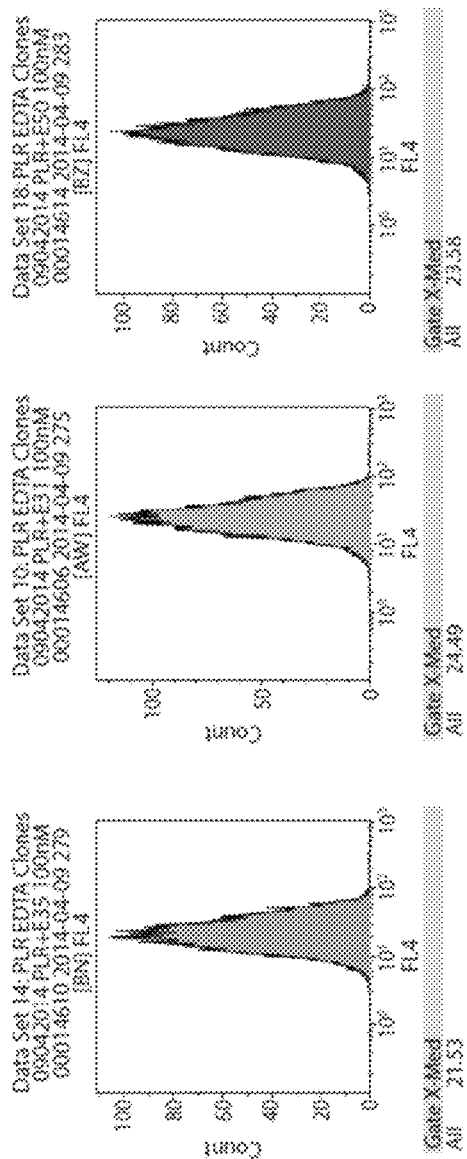
FIG. 15C

SWITCHABLE APTAMERS

FIELD

The present disclosure is in the field of chemical processes, namely affinity purification of target ligands capable of binding to switchable aptamers. The disclosure further relates to the isolation of switchable aptamers for targeting cells, viruses and antibodies.

BACKGROUND

The Systematic Evolution of Ligands by EXponential enrichment method, or SELEX, is a combinatorial chemistry technique for producing oligonucleotides of either single-stranded DNA or RNA that specifically bind to one or more target ligands. The method involves selection from a mixture of candidate oligonucleotides and step-wise iterations of binding, partitioning and amplification, using the same general selection scheme, to achieve a desired level of binding affinity and selectivity. SELEX has been used to evolve nucleic acid aptamers of extremely high binding affinity to a variety of targets. Some of these targets include, for example, lysozyme (Potty et al.), thrombin (Long et al.), human immunodeficiency virus trans-acting responsive element (HIV TAR) (Darfeuille et al.), hemin (Liu et al.), interferon gamma (Min et al.), vascular endothelial growth factor (VEGF) (Ng et al.), prostate specific antigen (PSA) (Savory et al.; Jeong et al.).

Aptamers have found applications in many areas, such as biotechnology, medicine, pharmacology, microbiology, and analytical chemistry, including chromatographic separation and biosensors.

Interestingly, structure-switching aptamers or SwAps have also found multiple applications. A review of SwAps as biosensors was published in 2009 by Sefah et al. Changes in fluorescence intensities between free and bound aptmamer complexes have been described to detect cocaine by aptamer-based capillary zone electrophoresis (Deng et al.). Multiple small molecule analytes have been detected by a similar method (Zhu et al.) High surface area, solid phase sol-gel-derived macroporous silica films have also been shown to be suitable platforms for high-density affinity-based immobilization of functional single stranded-aptamer molecules, allowing for binding of both large and small target ligands through SwAps with robust signal development (Carrasquilla et al.)

Aptamers have further been used for protein and small molecule purification using affinity chromatography. Indeed, aptamer affinity chromatography has been applied to protein purification (Romig et al.) and in the separation of mature dendritic cells from immature dendritic cells (Berezovski et al.). However, aptamer affinity chromatography has not to the inventors' knowledge been shown in the prior art to apply to the purification of cells, viruses or antibodies.

A major problem encountered when dealing with aptamer-based affinity chromatography to purify target ligands such as viruses, cells and certain other biological materials is the need for elevated temperatures or the addition of detergents to alter the conformation of the SwAp and to subsequently allow the release of the captured biomolecular target ligand from the solid medium or chromatography column. These harsh regeneration techniques decrease significantly the viability of cells and viruses, denature proteins and irreversibly change the structure of biomolecules. Furthermore, the lack of an efficient regeneration technique that can be generalized to other target-specific aptamers has been a challenge to the widespread use of aptamers for purification. Concerns have also been raised with regard to the possible cross-reaction between aptamers and other contaminants that might exist in the mixture containing the biomolecule to be purified. As such, until now, these problems have made the utilization of aptamers for the purification and recovery of purified targets such as viruses and cells very difficult to achieve.

The methods currently available for purification of viruses include: differential centrifugation, size exclusion chromatography (SEC) and heparin affinity column chromatography. These techniques are not without challenges. Sucrose differential gradient centrifugation is conventional for virus isolation in small quantities, but it is difficult to scale-up, is labour-intensive and requires long processing times, which may decrease the infectivity of viruses (Diallo et al.) SEC does not separate well from cell debris or large molecular aggregates with similar sized viruses, and is followed with additional concentration steps such as ultrafiltration or polyethylene glycol-6000 precipitation. The heparin column purification utilizes sepharose beads conjugated to linear anionic heparin molecules. This technique is used to purify proteins containing a heparin-binding domain as well as retroviruses. Although, this heparin method yields a purer product than the density gradient method, it still requires additional SEC purification from cationic proteins and salt.

SUMMARY

The present disclosure is directed to the purification of a target ligand of interest using aptamer molecules which exhibit a switchable affinity for the target in the presence or absence of a binding ion. According to various embodiments, the target can be a virus, a eukaryotic cell which may be receptor-positive for a selected receptor, a prokaryotic cell or an antibody.

According to one aspect, the disclosure relates to a method of isolating a switchable aptamer having affinity for a selected target ligand from a pool comprising a mixture of aptamers. The mixture may consist of a randomized pool of aptamers. According to this aspect, the method comprises the steps of:

a) incubating said pool with said target and a binding ion to form target-aptamer complexes comprising said target and aptamers specific to said target;

b) separating unbound aptamer molecules from the target-aptamer complexes;

c) contacting the target-aptamer complexes with a chelating agent having affinity for said binding ion wherein a switchable aptamer specific to said target is released from the target-aptamer complex; and d) isolating the switchable aptamer released in step c.

At least steps a through c may be performed at room temperature, for example a maximum temperature of 25° C.

The method may comprise the further step of amplifying the switchable aptamer isolated in step d.

The method may comprise the further step of measuring the affinity of said switchable aptamer for the target in the presence and absence of the binding ion.

Another aspect relates to an iterative process wherein two or more switchable aptamers are isolated and steps a through d are repeated using the two or more switchable aptamers in place of the mixture of aptamers in said pool wherein a switchable aptamer is isolated which has an increased affinity for the target relative to others of said switchable aptamers. From about 5 to about 20 such iterations or rounds (or between 5 and 20) may be performed for sequentially achieving higher purification levels, or from about 7 to about 15 (or between 7 and 15) rounds, or about 10 rounds.

Suitable targets for the method include a virus such as Vesicular Stomatis Virus (VSV) or a cell. Cellular targets include a receptor positive cell for a selected receptor such as a Neuropilin 1 (NRP) receptor, a Leukemia inhibitory factor (LIF) receptor, a Patched 1 (PTCH1) receptor, a Delta-Like Ligand 4 (DLL4) receptor or a plasminogen activator/urokinase receptor (PLAUR). A prokaryotic cell such as a bacteria may also comprise a target.

The binding ion may be a monovalent or divalent ion. Suitable divalent ions include calcium or magnesium or a combination thereof.

Suitable chelating agents include ethylenediaminetetraacetic acid (EDTA) or ethylene glycol tetraacetic acid (EGTA) or a combination thereof.

The target-aptamer complexes and the unbound aptamer molecules may be separated by centrifugation or by immobilizing the target-aptamer complexes and washing away unbound aptamer.

Suitable aptamers comprise nucleotides. The aptamers in said pool may comprise a random region of between 20 and 60 (or from about 20 to about 60) nucleotides, for example about 40 nucleotides.

According to a further aspect, the disclosure relates to a switchable aptamer having a high affinity for a selected target in the presence of a binding ion and a low affinity for said target in the absence of said binding ion. The switchable aptamer may be obtained through the method described herein. The switchable aptamer may comprise the nucleotide sequence represented in any one of SEQ ID NOS: 3 through 17 or 21 through 89, or a nucleotide sequence with at least 70%, 75%, 80%, 85%, 90%, 95% or 99% identity with any one of SEQ ID NOS: 3 through 17 or 21 through 89. The aptamer may have a target as described above.

According to a further aspect, the disclosure relates to a method for purifying a selected target from a complex mixture. According to this aspect, the method comprises the steps of:
  a) providing a switchable aptamer having affinity for said target wherein the switchable aptamer has a high affinity for the target when a binding ion is present and a low affinity for the target when the binding ion is absent;
  b) incubating said switchable aptamer with the complex mixture in the presence of said binding ion to produce target-aptamer complexes;
  c) separating the target-aptamer complexes from unbound components of the complex mixture;
  d) adding a chelating agent having affinity for the binding ion to the target-aptamer complexes to release the target from the target-aptamer complexes; and
  e) separating the released target from said switchable aptamer.

Suitable conditions and targets for said method may be the same as described herein for the method of isolating the switchable aptamer. The method may be performed at room temperature (maximum of 25° C.).

The method may comprise the further step of re-using the separated switchable aptamer to repeat said steps a through e on the same or a different complex mixture.

The switchable aptamer used in said method may comprise the switchable aptamer isolated according to the method described herein.

In the present specification, the following definitions apply, unless the context clearly requires otherwise:

"SwAps" or "switchable aptamers" means an aptamer with switchable affinity for one or more target ligands, wherein the affinity may be selectively increased or decreased by changing the environment of the aptamer such as contacting the aptamer with one or more ions.

"Target ligand" or "target" means a virus, a prokaryotic cell, a eukaryotic cell an antibody or a biomolecule whether synthetic or naturally produced which is capable of being bound to an aptamer.

"Biomolecule" means any molecule that is produced by a living organism or which is a synthetic analogue of such a molecule, including large macromolecules such as proteins, protein antibodies, peptides polysaccharides, lipids, and nucleic acids, as well as small molecules such as primary metabolites, secondary metabolites, and natural products.

"Aptamer" means a molecule that has an affinity for and binds to a specific target molecule via an interaction between the nucleic acid sequence of the aptamer and the target. This base pairing creates secondary structures such as short helical arms and single stranded loops. Combinations of these secondary structures results in the formation of tertiary structures that allow aptamers to bind to targets via van der Waals forces, hydrogen bonding and electrostatic interaction—aligning with the same ways antibodies bind to antigens. When this tertiary structure forms, the entire aptamer folds into a stable complex with the target ligand.

An aptamer may constitute a nucleic acid, which may be RNA or DNA or a peptide for a peptide aptamer.

"Chelating agent" is a molecule which binds to a metal ion. Chelation involves the formation or presence of two or more separate coordinate bonds between a polydentate (multiple bonded) ligand and a single central atom. Usually these ligands are organic compounds, and are called chelants, chelators, chelating agents, or sequestering agents.

"Binding ion"—an ion participating in formation aptamer-target complex

"Complex mixture"—a mixture of a target and non-target molecules, viruses, cells, and particles.

The objects and advantages of the present disclosure will become more apparent upon reading the following non-restrictive description of the preferred embodiments thereof, given for the purpose of exemplification only, with reference to the accompanying drawings.

In some embodiments, the steps of incubating the pool, separating the complexes, chelating the complexes, and separating the released SwAps is conducted at room temperature. This is especially preferred where the target is temperature sensitive, such as where the target is a virus or a cell. Amplification can be conducted at higher temperatures, as dictated by the polymerase chain reaction (PCR) protocol used.

Optionally, the selection method may also include an assay of the binding affinity of the SwAp to the target in the presence or absence of the binding ion. Such assessments may be useful for the identification of SwAps of particular interest for purification of the target, particularly those which exhibit a large change in affinity in the presence or absence of the binding ion. Affinity measurements also permit the selection to be conducted in an iterative fashion until a SwAp having a desired affinity is obtained. In one embodiment, the affinity assay is performed using flow cytometry. In other embodiments, target affinity may be measured using electrochemical means, such as by impedimetric assays. Each of these affinity assays are described in further detail below. Affinity assays may also be carried out in a variety of other ways known to the person of skill in the art. Examples include use of a gel-shift assay, filter-binding assay, surface plasmon resonance, stopped-flow assay or isothermal calorimetry.

For example, as discussed further below, an aptamer isolated for the purification of VSV may comprise any one of the nucleotide sequences set out in SEQ ID NOs: 3 to 17, each of which were derived from the selection method according to the present disclosure. In another embodiment, the aptamer has a sequence which has at least 70%, 75%, 80%, 85%, 90%, 95% or 99% identity with any one of SEQ ID NOs: 3 through 17.

In one embodiment, SwAps that have been isolated in Step a) are labelled with a tag. This tag is, for example, biotin. Other tags such as fluorescent dyes and markers are also contemplated.

In further embodiments of the disclosure, SwAps isolated in Step a) are immobilized on a surface, such as the stationary phase of a chromatography column, on a magnetic bead, on a membrane or in an agar medium prior to being contacted with the target. For example, as discussed further below, one or more biotin labelled aptamers may be immobilized on streptavidin-coated magnetic beads. Various other means of immobilizing SwAps would be apparent to those of skill in the art. For example, SwAps may be immobilized on a glass substrate modified with organosilanes or other fixing agents. Gold surfaces may also be used in conjunction with thiol-modifications to immobilize SwAps. A variety of other physical adsorption, covalent bonding, affinity binding, and matrix entrapment techniques are known in the art.

Figure 1:
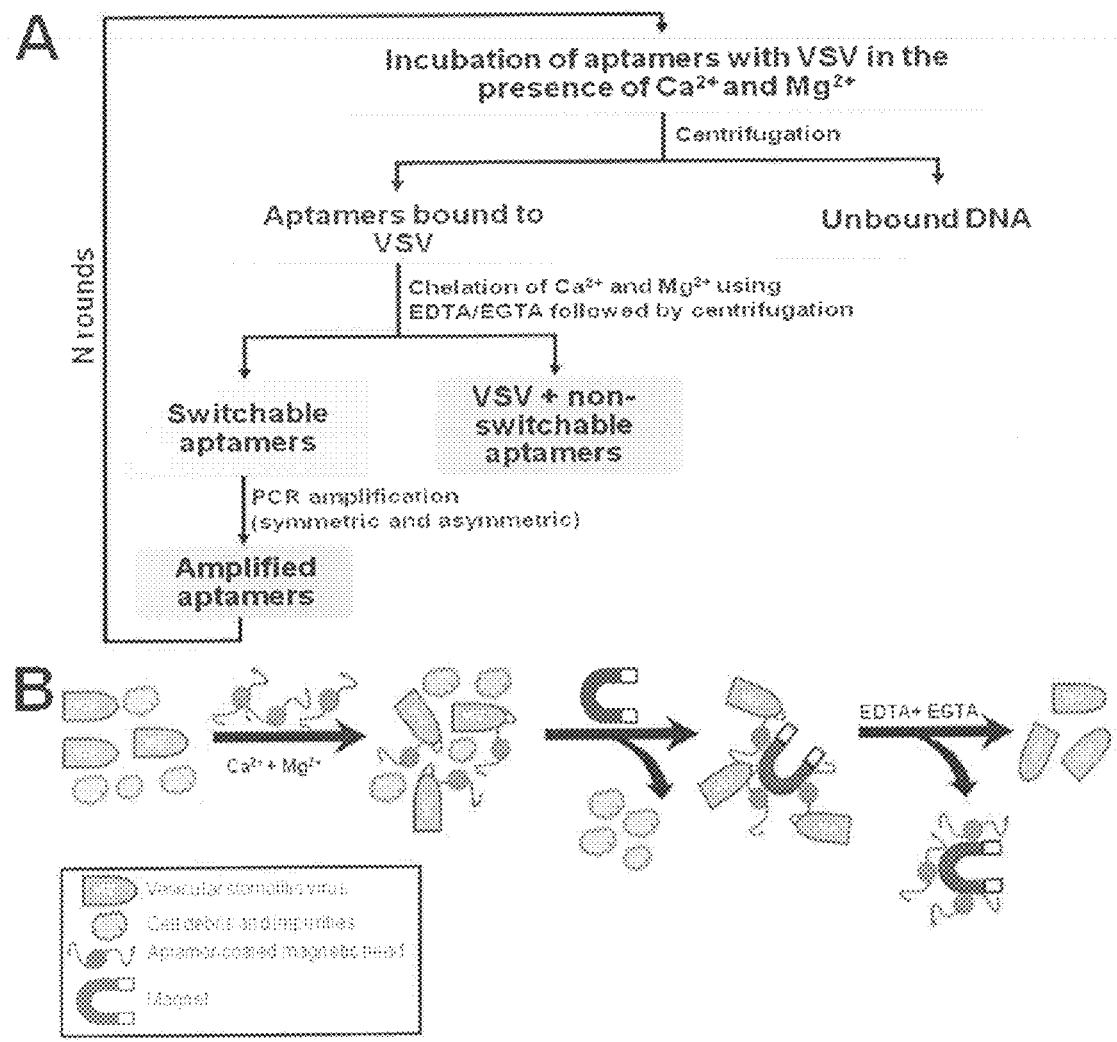
FIG. 1A shows a flow chart of the selection protocol for switchable aptamers through modified cell-SELEX.
FIG. 1B is a schematic representation of virus purification by switchable affinity aptamers.
Figure 2:
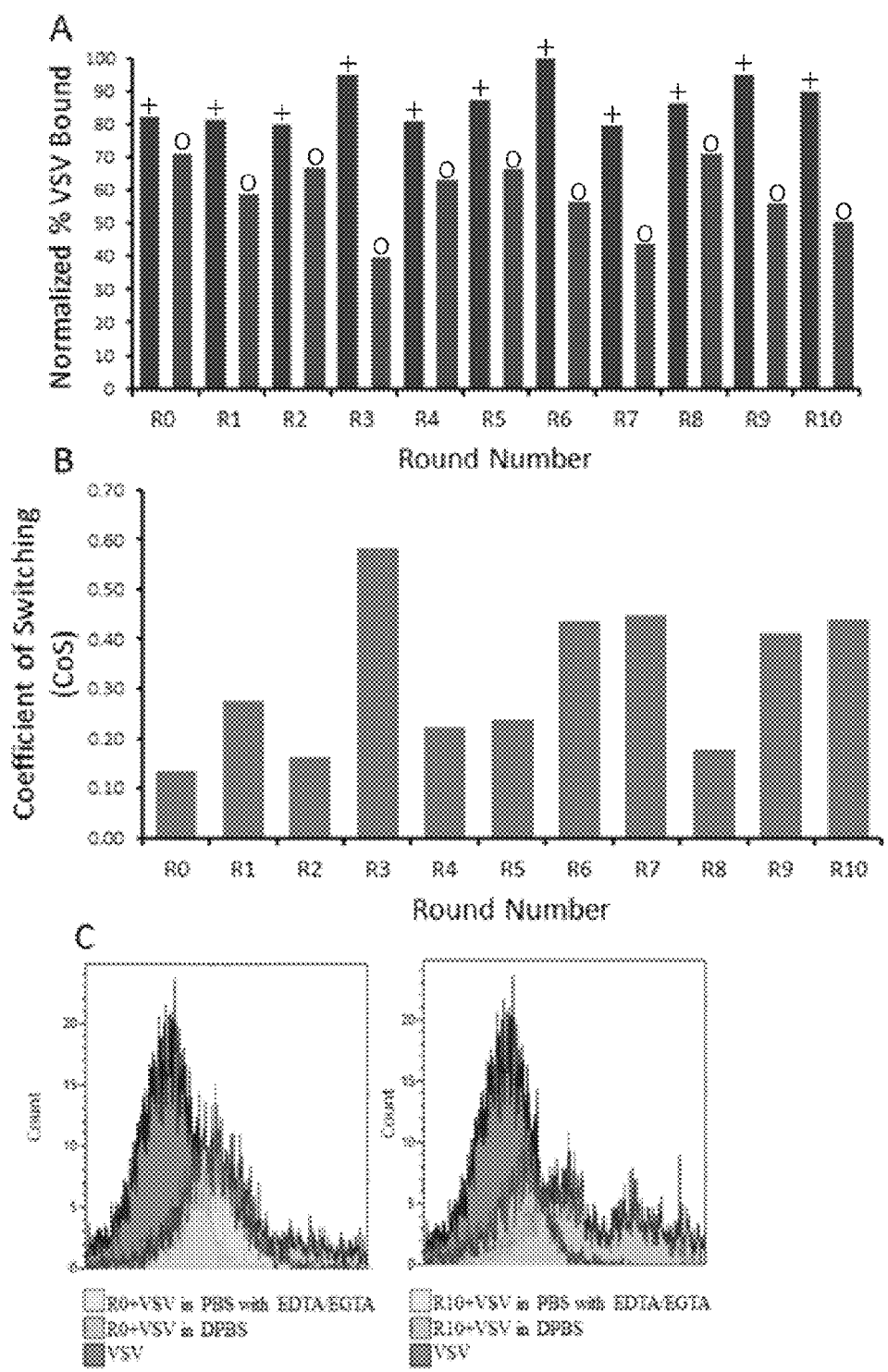
FIG. 2A shows a bar graph of the binding of the 10 pools and control aptamers to VSV in the presence of $Ca^{2+}$ and $Mg^{2+}$ (bars marked "+") and the amount of VSV remained bound to each pool after incubation with EDTA/EGTA mixture (bars marked "o").
FIG. 2B shows a bar graph of Coefficient of Switching (CoS) values calculated for each of the ten (10) aptamer pools by flow cytometry.
FIG. 2C shows flow cytometry histograms of aptamer pool 10 and Round 0. The left panel shows strong binding aptamer pool used to begin the experiment and the right panel shows aptamer pool 10 exhibiting switchable behaviour.
Figure 3:
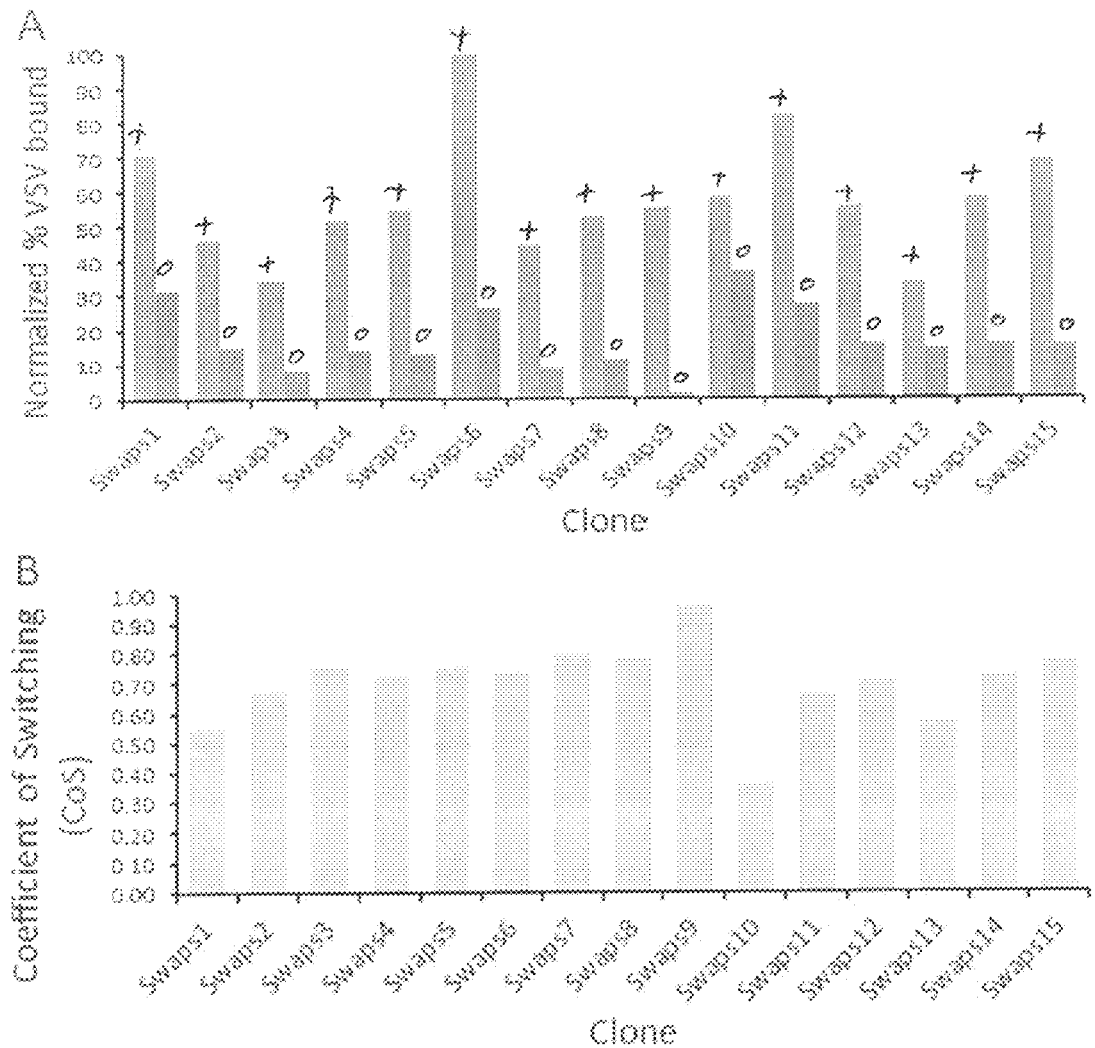
FIG. 3A shows a bar graph of the binding affinities of aptamer clones (50 nM) incubated with VSV (107 PFU) for 30 min prior to separation into 2 fractions one in DPBS ($MgCl_2$ and $CaCl_2$) (bars marked "+") and one containing 2.5 mM EDTA/EGTA (without $MgCl_2$ and $CaCl_2$) (bars marked "o").
FIG. 3B is a bar graph showing the Coefficient of Switching (CoS) of 15 aptamer clones obtained using flow cytometry.

Immobilization of the SwAps aids in the separation and washing steps during purification, particularly in respect of the separation of the aptamer-target complexes from the complex solution and the recovery and re-use of SwAps for further rounds of purification. For example, a SwAp immobilized on a magnetic bead may form aptamer-target complexes which can be separated from the complex solution as shown schematically in FIG. 1B. Similarly, as shown in FIG. 1B, magnetic beads may also be used to separate chelated SwAps from the target molecule. In other embodiments, immobilization of SwAps on the stationary phase of a chromatography column, in an agar medium, or on a membrane may be useful for separating aptamer-target complexes from the complex solution or chelated SwAps from the target by elution.

In Step b), the SwAps obtained through the isolation in Step a) are incubated with a binding ion. The binding ion can be, for example, a divalent ion like calcium or magnesium. Both calcium and magnesium together can also act as the binding ion. It will be understood that a monovalent or divalent cation can be used as the binding ion. Submillimolar levels of the binding ion (0.01-1 mM) induces conformational changes in the aptamer DNA and stabilize secondary and tertiary structures of the switchable aptamers. In the early folding stages, aptamers form secondary structures stabilized through the binding of monovalent cations or divalent cations in order to neutralize the polyanionic backbone. The later stages of this process involve the formation of DNA tertiary structure, which is stabilized almost largely through the binding of divalent ions such as magnesium and calcium with contributions from potassium binding. As such, the SwAps bind to their targets in the presence of $Mg^{2+}$ and $Ca^{2+}$ ions and release their targets once the ions are removed by the addition of the binding ion chelator in Step d).

Step c) calls for the separation of the target-aptamer complexes of Step b) from the complex mixture. Where the SwAps are immobilized, this typically involves washing the target-aptamer complexes with a washing agent to remove debris or impurities. For example, the washing agent can be Dulbecco's phosphate-buffered saline (DPBS), which is particularly useful where the binding ion is $Mg^{2+}$ or $Ca^{2+}$. If the aptamers are not immobilized, other means of separation known in the art may be employed, such as centrifugation or electrophoresis.

The above steps result in a highly purified aptamer/target complex, such that the subsequent separation of these components produces essentially a two-component mixture comprising an isolated target and an isolated switchable aptamer that is specific to this target.

Step d) describes the addition of a chelating agent to the mixture of target-aptamer complexes to chelate the binding ion. The chelating agent will be selected in accordance with the binding ion. For example, if the binding ion is $Ca^{2+}$, the binding ion chelator will be ethylenediaminetetraacetic acid (EDTA). Similarly, if the binding ion is $Mg^{2+}$, the binding ion chelator will be ethylene glycol tetraacetic acid (EGTA). It follows that if $Ca^{2+}$ and $Mg^{2+}$ are both used together as binding ions, both EDTA and EGTA will be used a chelators. The chelators remove the binding ion, and consequently allow for the release of the target by the SwAps.

Step e) describes the collection of the purified target released by chelation of the SwAps. In some embodiments, such as the embodiment show in FIG. 1B, this is accomplished by precipitating the SwAps out of solution using magnetic beads. In other embodiments, SwAps coupled to particulate surfaces may be drawn out of solution by centrifugation. In still other embodiments, SwAps are retained in the stationary phase of a chromatography column while the target is eluted using a washing agent. In still other embodiments, SwAps are retained on the surface of a substrate (such as, for example, agar, glass, or gold) and the released target is collected from solution. Optionally, the aptamer with switchable affinity is also collected or retained, thereby permitting the aptamer to be re-used a number of times for the purification of the same target.

In some embodiments, the purification process is performed in an iterative manner to achieve higher levels of purity, such that the purified target from the first round of purification acts as the complex solution in subsequent rounds of purification.

EXAMPLES

The following examples detail the use of SwAps with controlled affinity for the purification of Vesicular Stomatis Virus (VSV). As shown below, the virus captured with such SwAps can be recovered upon treatment with a simple eluent, containing a mixture of EDTA/EGTA at room temperature and neutral pH. Using the method described herein, a total of 15 sequences were obtained as a first pool of aptamers with varying affinity to VSV. Each sequence was assessed for affinity and switchability by both flow cytometry and impedimetric analysis. SwAps clones 5, 6, 7 and 9 were selected for further study. SwAps clone 6 was the candidate that demonstrated the best affinity and switchability for VSV. The aptamers switchability is a function of the divalent cations and the affinity of the SwAps to VSV can be terminated upon chelation of these cations. The resulting system provides an efficient and efficiency and simplicity of the SwAps-based purification technique described here above.

Example 1

Production and Purification of VSV

The protocol of VSV production and harvesting was previously described elsewhere (Diallo et al.). Briefly, 6 plates of Vero cells were grown until confluent and then were infected with VSV (approx. $10^6$ PFU/plate). After 24 hours, the supernatant was collected into 50-mL tubes and centrifuged to removed the cell debris. Subsequently, the supernatant was passed through a 0.2 μm filter (Pall Inc., USA) and the pellet containing the virus was then re-suspended in DPBS. Finally, it was aliquoted and stored at −80° C.

Example 2

DNA Library and Primers

N40 ssDNA library, with the sequence ($^{5'}$CTCCTCT-GACTGTAACCACG-($N_{40}$)-GCATAGGTAGTCCA-GAAGCC$^{3'}$) (SEQ ID NO:90) was used for all experiments. It consists of total of 80 nucleotides and contains two flanking primer regions of 20 nucleotides each, whereas the central region contains 40 random nucleotides. Fluorescently-labeled 5'-primer (6-FAM/$^{5'}$CTCCTCTGACTG-TAACCACG$^{3'}$) (SEQ ID NO:1) and the non labeled 3'-primer ($^{5'}$GGCTTCTGGACTACCTATGC$^{3'}$) (SEQ ID NO:20) and the library were all obtained from Integrated DNA Technologies, U.S.

After the selection process described herein, some aptamers can be slightly longer or shorter due to mutations happened in PCR steps or original synthesis of the DNA library.

The larger the size of this region, the more combinations of nucleotides will result and the greater the chance of an exact "hit" with a target. In some embodiments, practical limits for are about 20-60 nucleotides for the central region.

Example 3

Selection of Aptamers with Switchable Affinity

Submillimolar levels of calcium and magnesium (0.01-1 mM) induce conformational changes of DNA and stabilize secondary and tertiary structures. In the early folding stages, aptamers form secondary structures stabilized through the binding of monovalent cations or divalent cations in order to neutralize the polyanionic backbone. The later stages of this process involve the formation of DNA tertiary structure, which is stabilized almost largely through the binding of divalent ions such as magnesium and calcium with contributions from potassium binding. Here the use of these cations through a modified cell-SELEX technique to create aptamers with switchable affinity has been exploited. These aptamers have a switchable functionality allowing them to bind to their targets in the presence of $Mg^{2+}$ and $Ca^{2+}$ ions and to release their targets once the ions are removed. To allow for this functionality, an additional step in the cell-SELEX process was added using two strong chelating agents, namely 2.5 mM EDTA and EGTA in PBS. The SwAps selection scheme through modified cell-SELEX is presented in FIG. 1A.

The process for the selection of SwAps involves 5 steps: 1) Incubation of aptamers with $2.5\times10^9$ pfu $mL^{-1}$ of VSV in DPBS for 30 minutes; 2) Washing VSV to remove unbound aptamers by centrifugation; 3) Treatment with EGTA & EDTA to remove $Mg^{2+}$ and $Ca^{2+}$ and release VSV; 4) Collection of unbound switchable aptamers through centrifugation; and 5) PCR amplification (symmetric+asymmetric).

In more ample details, the selection of the switchable aptamers begins with adding VSV to a pool of aptamers in DPBS, along with $Ca^{2+}$ and $Mg^{2+}$, followed by incubation for 30 min at room temperature. This allowed for binding between aptamers and VSV to reach equilibrium.

Centrifugation allowed for the removal of unbound DNA aptamers, where the aptamers bound to VSV became a part of the pellet after the centrifugation step, whereas the non-bound DNA remained in the supernatant and was discarded. Addition of EGTA & EDTA to remove $Ca^{2+}$ and $Mg^{2+}$ allowed for the collection of aptamers exhibiting switchable affinity. These aptamers were collected and amplified by symmetric and asymmetric PCR.

The selection scheme involved 5 steps and was repeated for 10 rounds. The scheme involved (1) incubation of aptamer pool with VSV, (2) separation of bound aptamers, (3) addition of EDTA and EGTA, (4) collection of unbound aptamers, and (5) PCR to amplify the desired aptamer pool. Each aptamer pool was denatured by heating at 95° C. for 5 min in Dulbecco's phosphate buffered saline (DPBS), containing 0.901 mM $CaCl_2$, 0.493 mM $MgCl_2$, 2.67 mM KCl, 137.93 mM NaCl, 1.47 mM $KH_2PO_4$, and 8.06 mM $Na_2HPO_4$ (D8662, Sigma-Aldrich, U.S.) and was allowed to re-fold on ice for 10 min. Prior to each round of selection, $2.5\times10^9$ PFU $mL^{-1}$ of VSV was incubated with 100 nM of FAM-labeled aptamer pool in a total volume of 50 μL (DPBS) for 30 min on a shaking incubator at 25° C. and 400 r.p.m. The mixture was then centrifuged at 17 200 r.c.f. for 15 min. Next, the supernatant was discarded and 50 μL DPBS was added and the mixture was centrifuged again. This washing step was repeated 3 times for rounds 1-5 and increased to 5 times for rounds 6-10. Upon completion of the last washing step, the pellet was re-suspended in 50 μL of an equimolar mixture of 2.5 mM EDTA (EMD Chemicals, U.S.)/EGTA (Bio Basic Inc., Canada) in PBS (2.67 mM KCl, 1.47 mM $KH_2PO_4$, 8.06 mM $Na_2HPO_4$ and 137.93 mM NaCl) for 30 min. Afterward, the mixture was centrifuged for 15 min at 17 200 r.c.f. and the supernatant was transferred to a separate tube for storage at −20° C. Finally, aptamers were amplified by PCR and the cycle was repeated.

Aptamer pools were amplified using bundled symmetric and asymmetric PCR after each subsequent round of selection. Symmetric PCR amplifies and produces dsDNA, where 5 μL of the supernatant collected during selection and containing the bound aptamers were mixed with 45 μL of symmetric PCR master mix. The master mix contained the following reagents in final concentrations: 1×PCR buffer (Promega Corporation, U.S.), 2.5 mM $MgCl_2$, 0.028 U $\mu L^{-1}$ GoTaq Hot Start Polymerase (Promega Corporation, U.S.), 220 μM dNTPs, 500 nM forward primer (5'CTCCTCT-GACTGTAACCACG3') (SEQ ID NO:1), and 500 nM reverse primer (5'GGCTTCTGGACTACCTATGC3') (SEQ ID NO:20) (Integrated DNA Technology, U.S.). Upon completion, 5 μL of the symmetric master mix were added to the asymmetric PCR master mix containing the same reagents as the symmetric master mix but with 1 μM forward FAM-labeled primer (FAM-5'CTCCTCTGACTGTAAC-CACG3') (SEQ ID NO:1) and 50 nM reverse primer. Asymmetric PCR has low amplification power but it produces ssDNA. Both symmetric and asymmetric PCR used the following program: preheating for 2 min at 95° C., 15 cycles for symmetric PCR or 10-15 cycles for asymmetric PCR of 30 sec at 95° C., 15 s at 56.3° C., 15 s at 72° C., and hold at 4° C.

A total of 10 rounds of SwAps selection were performed, and the selected aptamers were analyzed by flow cytometry.

Example 4

Flow Cytometric Affinity Analysis of Aptamer Pools and Clones

For affinity testing, pools were purified by loading the mixture onto 30 kDa cut-off filter (Nanosep, U.S.). This was followed by centrifugation at 3 800 r.c.f. for 13 min at 16° C. Subsequently, an equal volume DPBS was added for two additional washing steps for 10 min each. The purity was tested by running the raw and purified samples on 3% agar gel (Sigma-Aldrich, U.S.) at 150V. Finally, concentration of sample was measured using NanoDrop-2000 UV-Vis spectrophotometer, U.S.

Aptamer pool/clone affinity to VSV and switchability were measured using a FC-500 Flow Cytometer (Beckman Coulter Inc., U.S.). All samples, contained 100 nM of purified FAM-labeled aptamer, were incubated with $2.5 \times 10^7$ PFU $mL^{-1}$ at room temperature for 30 min in DPBS. The samples were then divided into two portions; the first portion had DPBS added to it the second had 10 mM EDTA/EGTA 30 min at room temperature. All samples were made to 250 μL prior to flow analysis. Control experiments were performed using the aptamer pool 8 and a sample of VSV was stained using TOTO-3 dye (Invitrogen, U.S.) to allow for identification on flow cytometry.

Ten selected pools of aptamers were examined for two criteria; the affinity of the aptamer pool to VSV and the ability of this pool to release VSV upon treatment with the EDTA/EGTA mixture which is denoted here by the Coefficient of Switching (CoS). Rather than using the N40 DNA library as a standard, it was decided to compare the aptamer pools to the initial pool which was used to start selection. This was decided as a better representation because unlike with typical SELEX protocols where the DNA library would represent "round 0", here our starting pool was pre-selected to bind to VSV. Thus, comparing to the native library would not have provided us with information as to whether the selection scheme was truly creating switchable aptamers. All pools were FAM-labeled, purified and made to a total volume of 100 μL in DPBS with 50 nM aptamer pool and $10^7$ PFU $mL^{-1}$ VSV. Flow cytometry results were analyzed by Kaluza software; one can see two trends in FIG. 2 referring to a weakly and strongly switchable aptamer pool. FIG. 2A shows the binding of the 10 pools and control to VSV in the presence of $Ca^{2+}$ and $Mg^{2+}$ (in blue) and amount of VSV remained bound to each pool after incubation with EDTA/EGTA mixture (in red). Pools 3, 6, 9, and 10 exhibited strong affinity to VSV and are thus promising candidates.

a. FIG. 2B shows the CoS values calculated for each respective pool, where a CoS of 1 indicates an aptamer exhibiting the highest switchability, whereas 0 refers to an aptamer completely unable to switch. Using equation 1:

$$CoS = 1 - \left(\frac{\%\ \text{Bound Aptamers to } VSV \text{ in } DPBS}{\%\ \text{Bound Aptamer to } VSV \text{ with } EDTA + EGTA}\right) \quad (1)$$

How effectively the aptamers can switch from their bound and unbound form can be compared. Round 0 is the lowest, followed by rounds 2, and 8, all showing a CoS of <0.20. The CoS was small, which indicates that the binding of the pool to VSV was largely unaffected by the presence or absence of $Ca^{2+}$ and $Mg^{2+}$. Large CoS values was exhibited by pools 3, 7 and 10. Since rounds 1 and 2 represent the beginning of selection, it was expected that they would not show a good switching functionality. One would think that as the number of rounds of selection increases, the binding and switchability characters would also increase linearly. This is seldom the case in aptamer selection as after each round, mutations were introduced during PCR, which may be beneficial or detrimental to binding. Pool 10 showing the highest affinity and switchability was thus selected for cloning. More washing steps were employed during the later rounds which resulted in more specificity. Flow cytometry histograms of round 10 are demonstrated in FIG. 2C where the switchable nature of the aptamer pool is clear. When virus is bound by an aptamer, the fluorescence of the virus particle increases resulting in a shift to the right as seen in the histogram. Similarly, when the VSV-aptamer complex dissociates in the presence of EDTA/EGTA, the overall fluorescence decreases and the histogram shifts to the left side.

Aptamer pool 10 was cloned and a total of 15 SwAps sequences were obtained. All clones were tested for their respective affinities to VSV and the switchability as was described above. FIG. 3 shows the data obtained for the clones using a Beckman FC600 flow cytometer. SwAps clones 1, 6, 11, and 15 exhibited good affinity and high CoS values. In order to confirm the data obtained using flow cytometry, an electrochemical aptamer-based sensor was developed to estimate the affinity between each aptamer and VSV as well as the switchability of each aptamer upon elution. This method had the added benefit of having the aptamers fixed on the surface of the gold sensor. This would likely mimic the behavior of aptamers when they would be covalently attached to an affinity chromatography matrix or streptavidin coated beads as in this work, and allow for selection of aptamers that would show the best performance in the course of VSV purification.

Example 5

Cloning and Sequencing of High Affinity SwAps

Aptamer pool 10 (SEQ ID NO: 18) which showed both high affinity and switchability was selected for cloning to obtain individual aptamer sequences. The resulting sequences are provided in SEQ ID NOs: 3 through 17, also reproduced below at Table 3.

Briefly, the pool was amplified using symmetric PCR to obtain dsDNA and then was purified using a DNA gel extraction kit (AxyGen Biosciences, U.S.). Cloning was performed according to the protocol obtained with the M13mp18 perfectly blunt cloning kit (Novagen, U.S.). White colonies identifying the presence of the insert were then grown in LB+ Ampicillin overnight in a shaking incubator. PCR was then performed to ensure the presence of the insert with the following master mix. For each PCR reaction, 2 μL of the cell suspension was mixed with 18 μL of the PCR Master Mix containing: 1×PCR GC buffer, 2.5 mM $MgCl_2$ (Mallinckrodt Baker, Inc., U.S.), 0.01 U $\mu L^{-1}$ KAPA 2G Robust Hot Start DNA polymerase (Kapa Biosystems, U.S.), 220 μM dNTPs, 0.5 μM forward FAM-labeled primer, and 0.5 μM reverse primer. Amplification was performed using a PCR program (preheating for 5 min at 95° C., 30 cycles of 30 s each at 95° C., 15 s at 56.3° C., 15 s at 72° C., and hold at 4° C.). Upon identifying the clones with the plasmid containing the insert, amplification was performed. This was carried out using the same aforementioned master mix but with the M13 forward primer ($^{5'}$GTAAAACGACGGCCAGT$^{3'}$) (SEQ ID NO:91) and M13 reverse primer ($^{5'}$AGCGGATAACAATTTCACACAGG$^{3'}$) (SEQ ID NO:92). The unpurified PCR product obtained was sent to McGill University and Genome Québec Innovation Centre, Canada for sequencing.

Example 6

Impedimetric Analysis of the Affinity and Switching Properties of SwAps

Electrochemical studies, including cyclic voltammetry (CV) and electrochemical impedance spectroscopy (EIS) were carried out with an electrochemical analyzer (CH Instruments 660D, TX, U.S.) connected to a personal computer. All measurements were performed at room temperature in an enclosed and grounded Faraday cage. A conventional three-electrode configuration printed on a ceramic substrate; including a GNPs-SPCE electrode as the working electrode, carbon counter electrode, and a silver pseudo-reference electrode. A three-electric contacts edge connector was used to connect the screen-printed electrode with the potentiostat (Dropsens, Spain). The open-circuit or rest-potential of the system was measured prior to all electrochemical experiments to prevent sudden potential-related changes in the self-assembled monolayer (SAM). CV experiments were performed at a scan rate of 100 mV $s^{-1}$ in the potential range from −600 to 800 mV. EIS measurements were conducted in the frequency range of 100 kHz to 0.1 Hz, at a formal potential of 250 mV and AC amplitude of 5 mV. The measured EIS spectra were analyzed with the help of equivalent circuit using ZSimpWin 3.22 (Princeton Applied Research, U.S.) and the data were presented in Nyquist plots. Electrochemical measurements were performed in 25 mM sodium phosphate buffer (pH 7), containing 2.5 mM $K_4Fe(CN)_6$ and 2.5 mM $K_3Fe(CN)_6$.

Prior to experiments, the gold nanoparticles modified screen-printed carbon electrode (GNPs-SPCE) (L33×W10×H0.5, Dropsens, Spain) was washed thoroughly with deionized water then dried with pure $N_2$. Subsequently, the electrode was incubated with equimolar amounts (1 μM) of the selected aptamer and an HPLC purified, Thiol-spacer-$^{5'}$GGCTTCTGGACTACCTATGC$^{3'}$ (SEQ ID NO:20) modified at the 5' position with a 6-hydroxyhexyl disulfide group, detection probe (Integrated DNA Technologies, U.S.) in 25 mM sodium phosphate buffer, pH 7, for 5 days at 4° C. Finally, the electrode was incubated with 1 mM 2-mercaptoethanol in ethanol for 5 min to back-fill the empty spots of the electrode surface, thus reducing the non-specific adsorption onto the surface.

Figure 5:
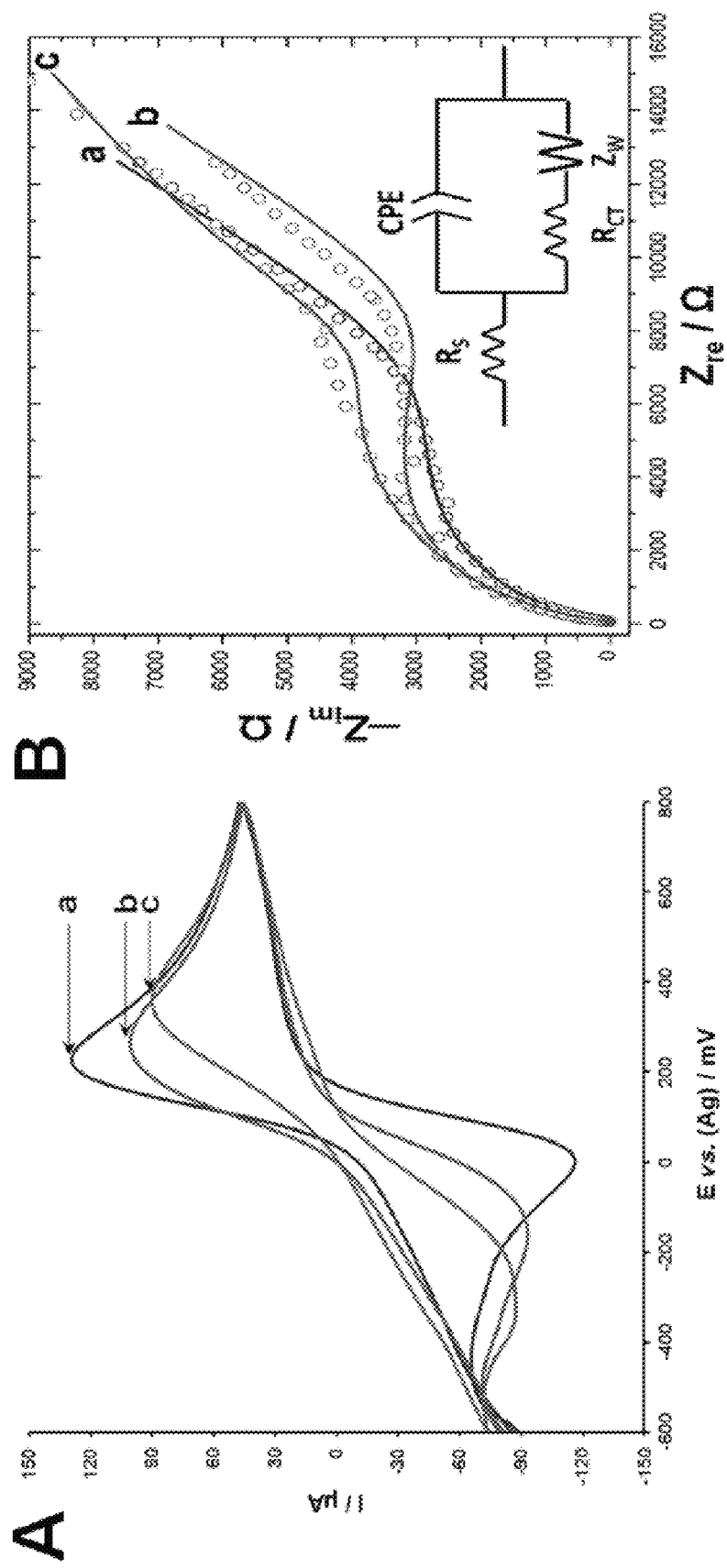
Figure 6A:
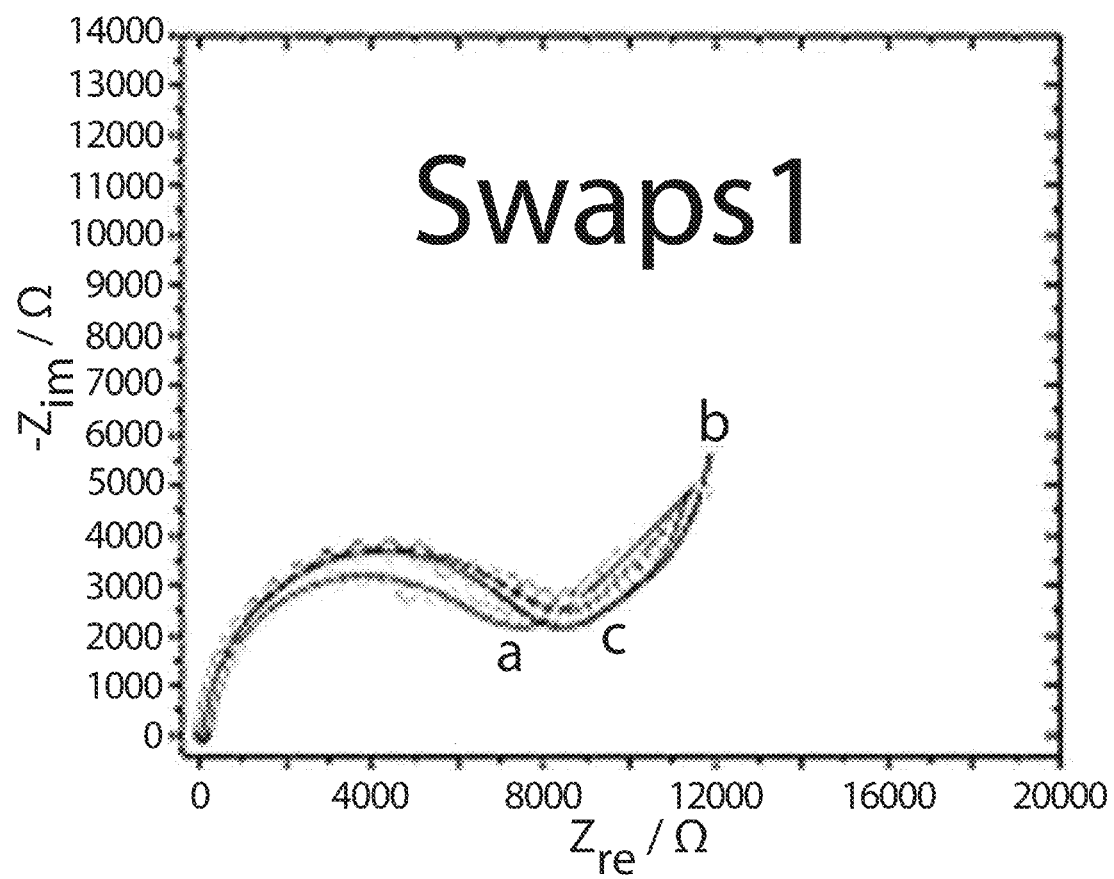
Figure 6B:
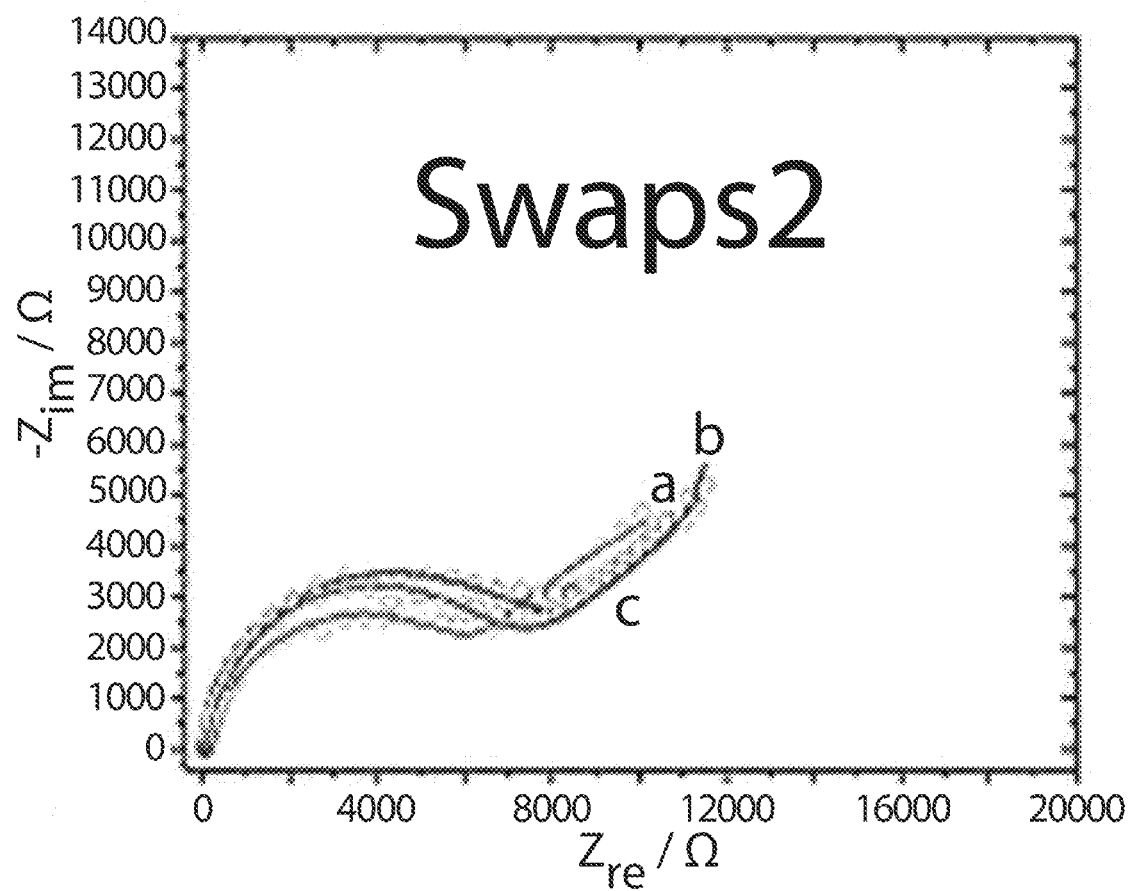
Figure 6C:
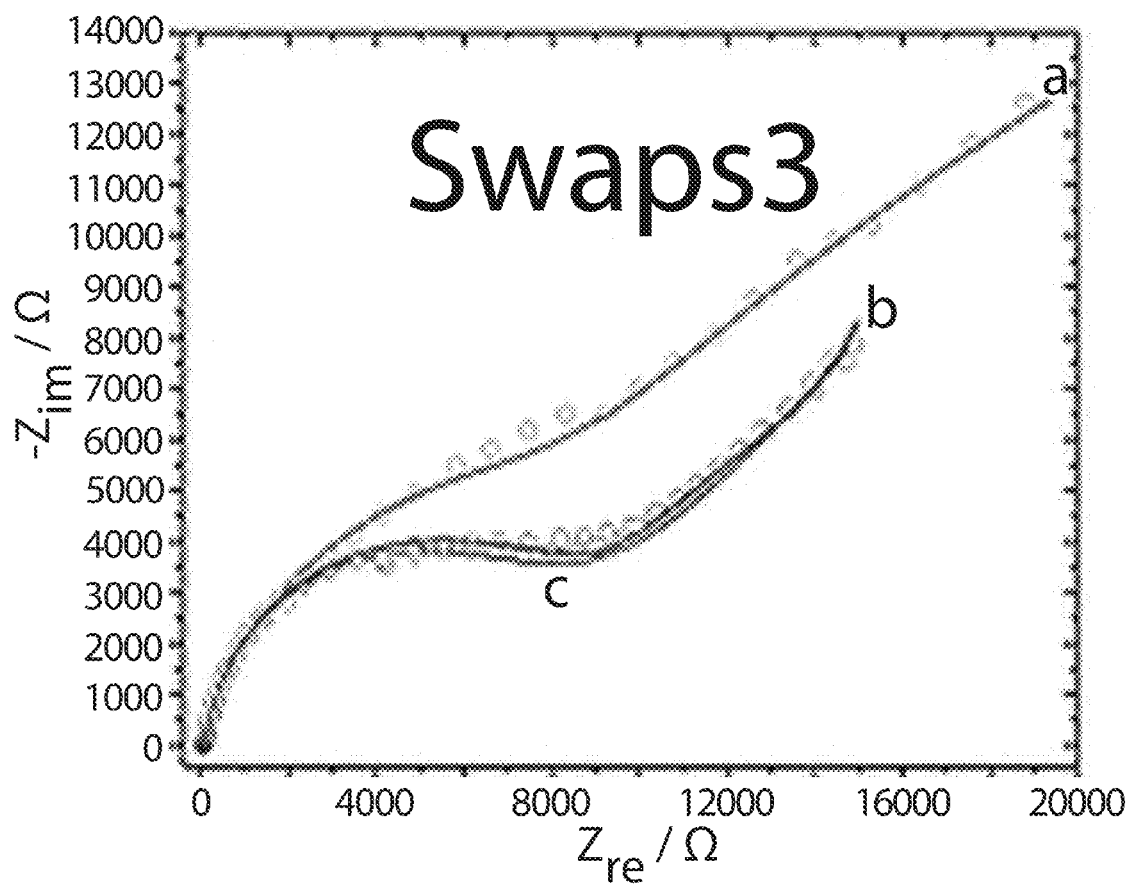
Figure 6D:
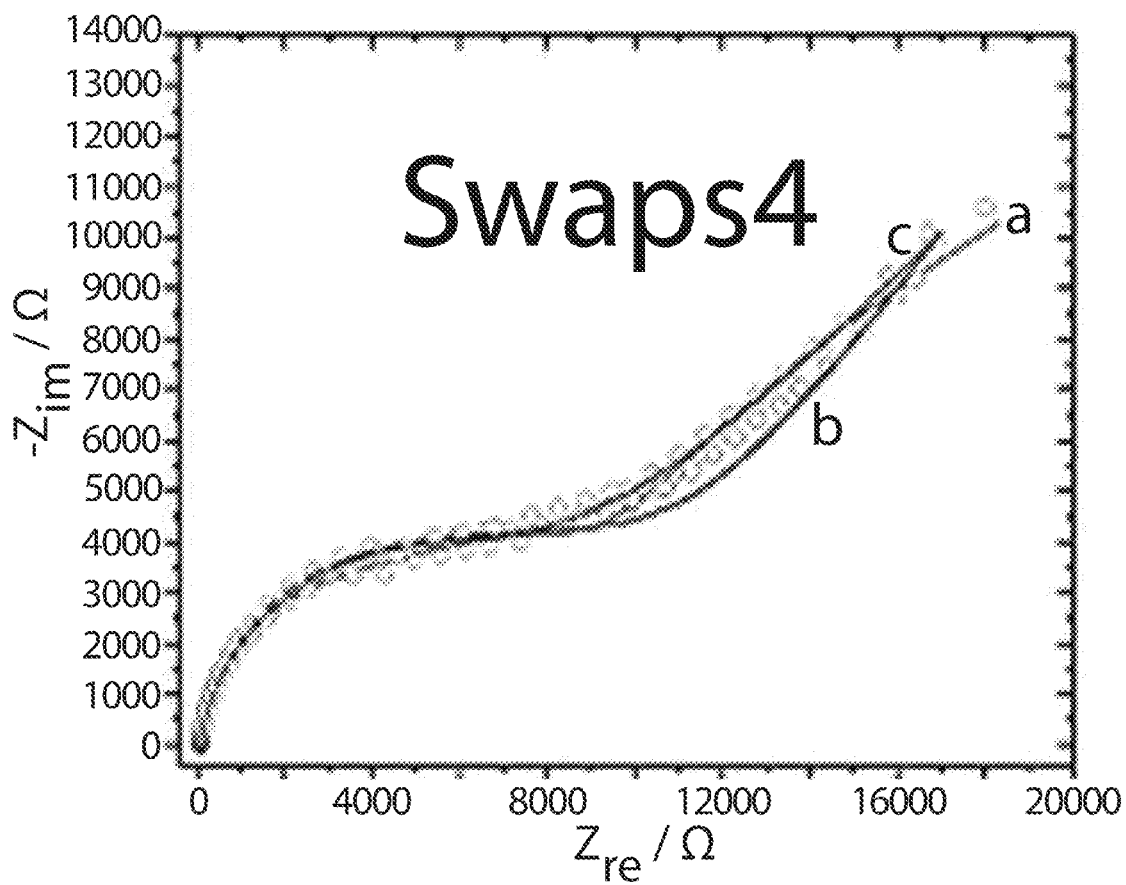
Figure 6E:
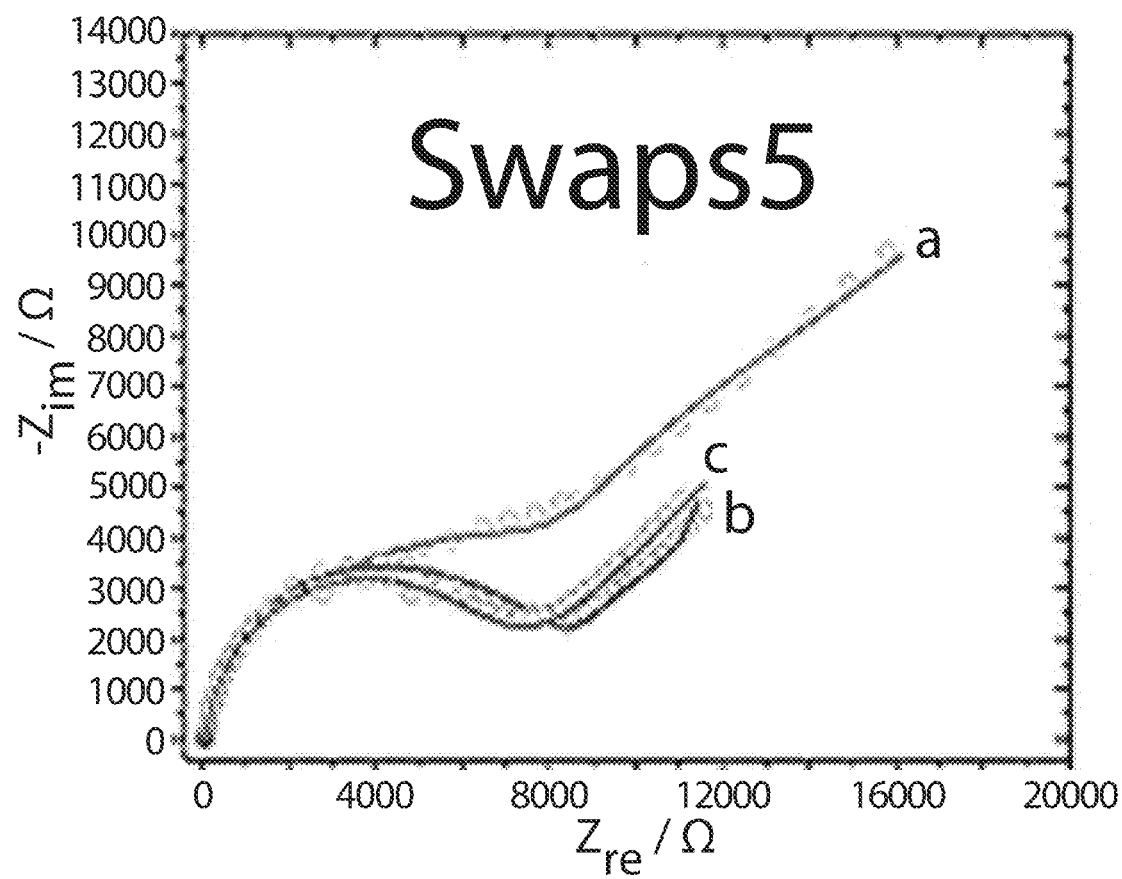
Figure 6F:
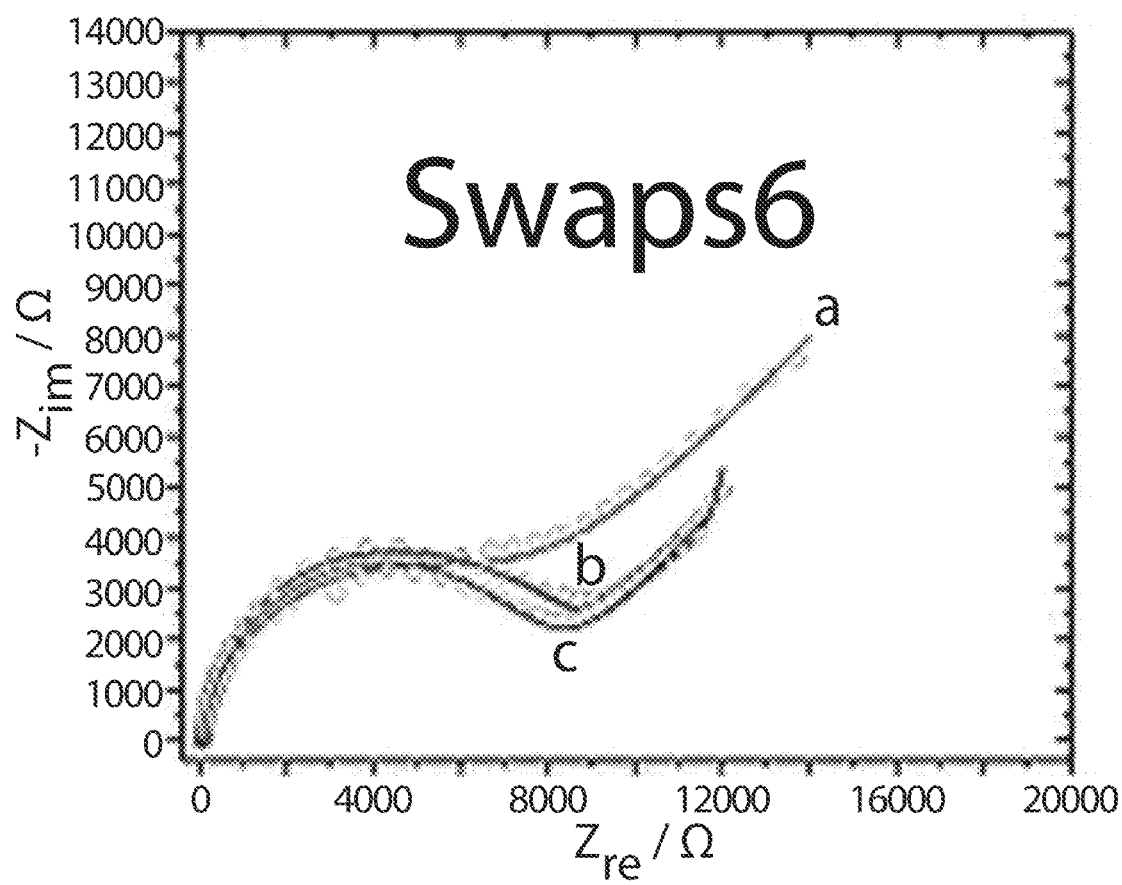
Figure 6G:
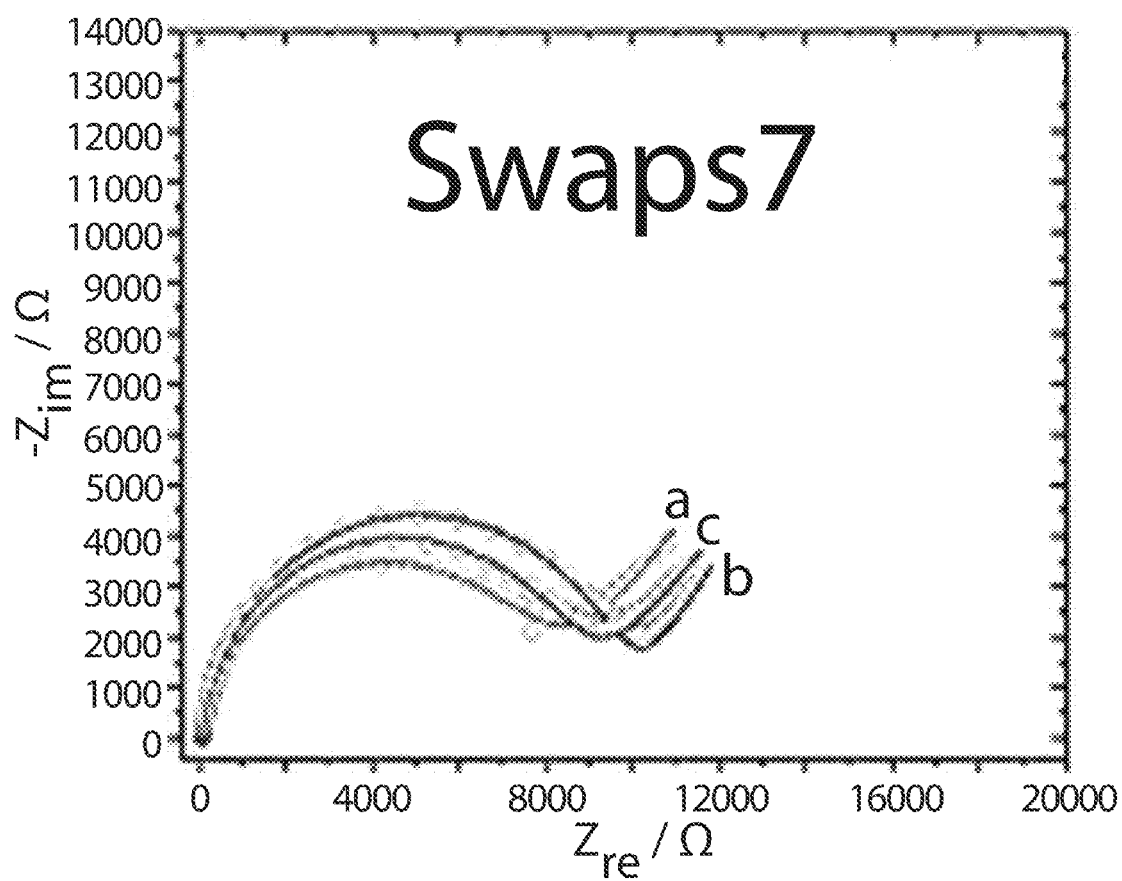
Figure 6H:
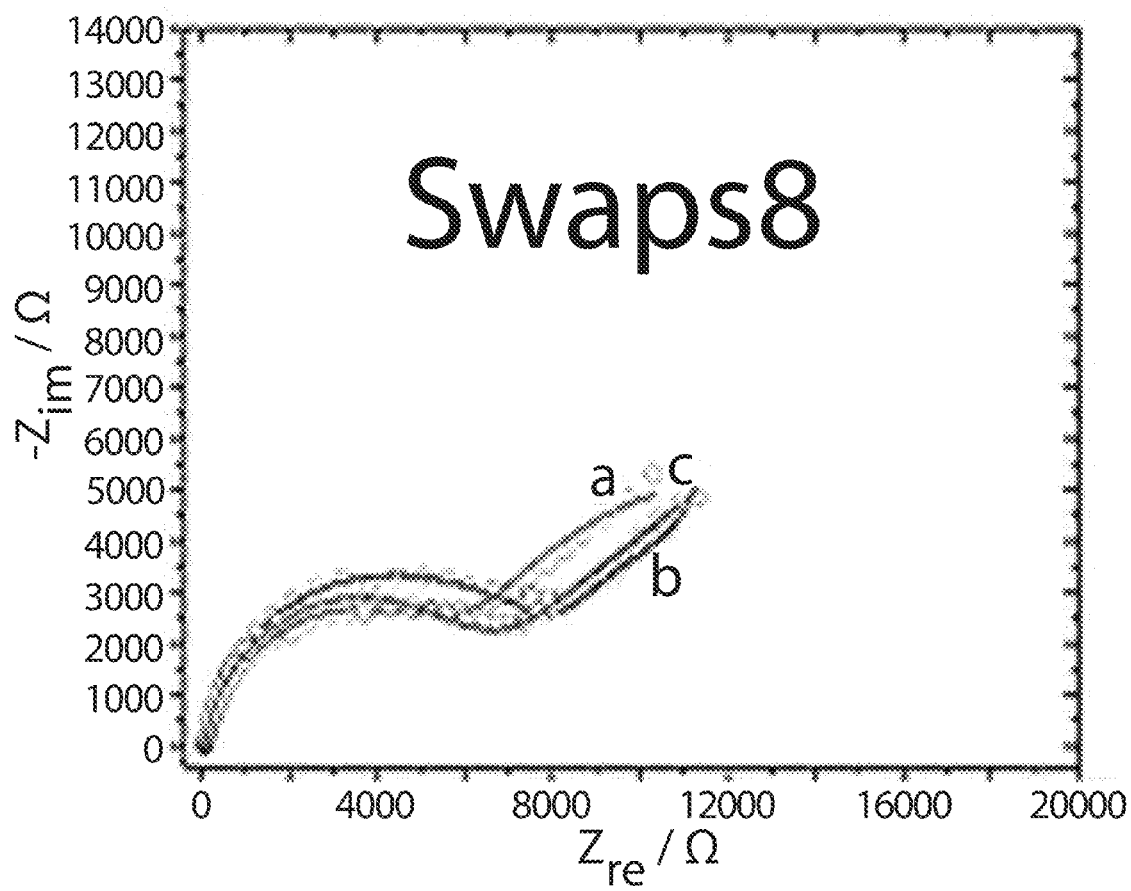
Figure 6I:
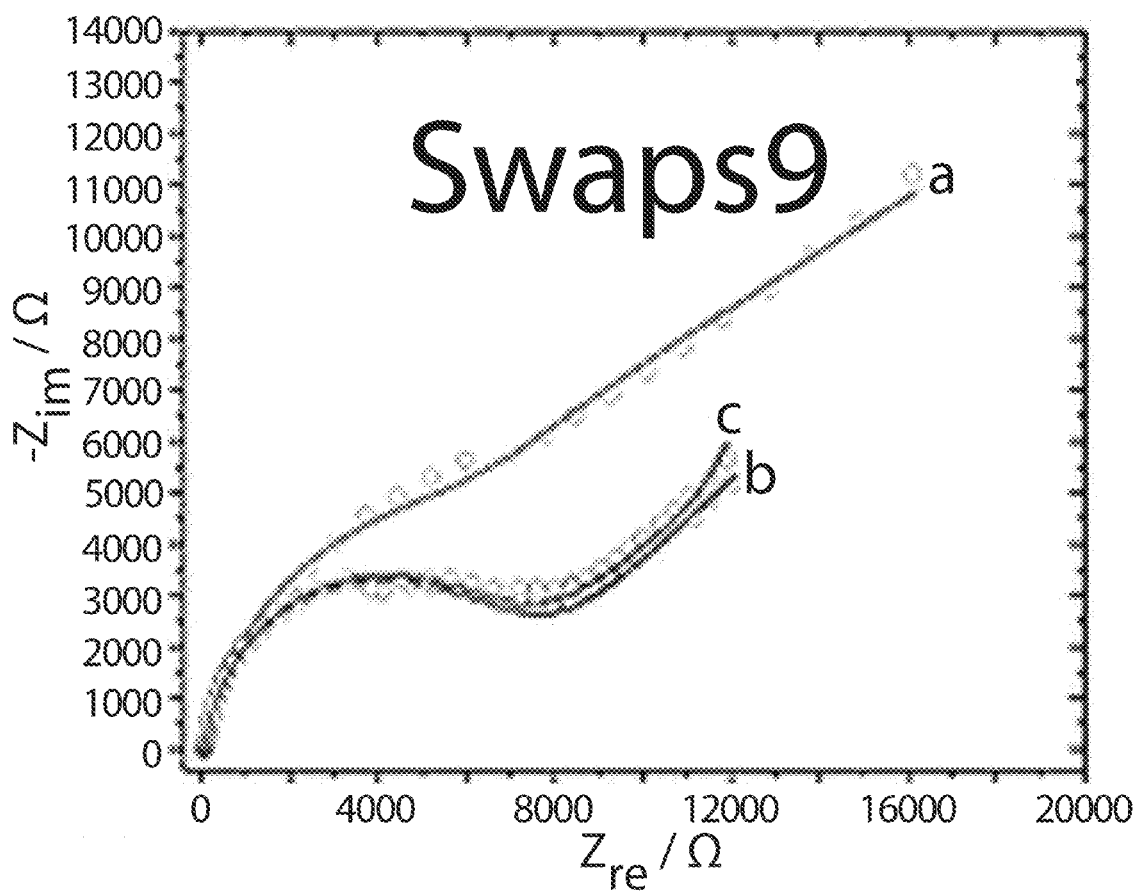
Figure 6J:
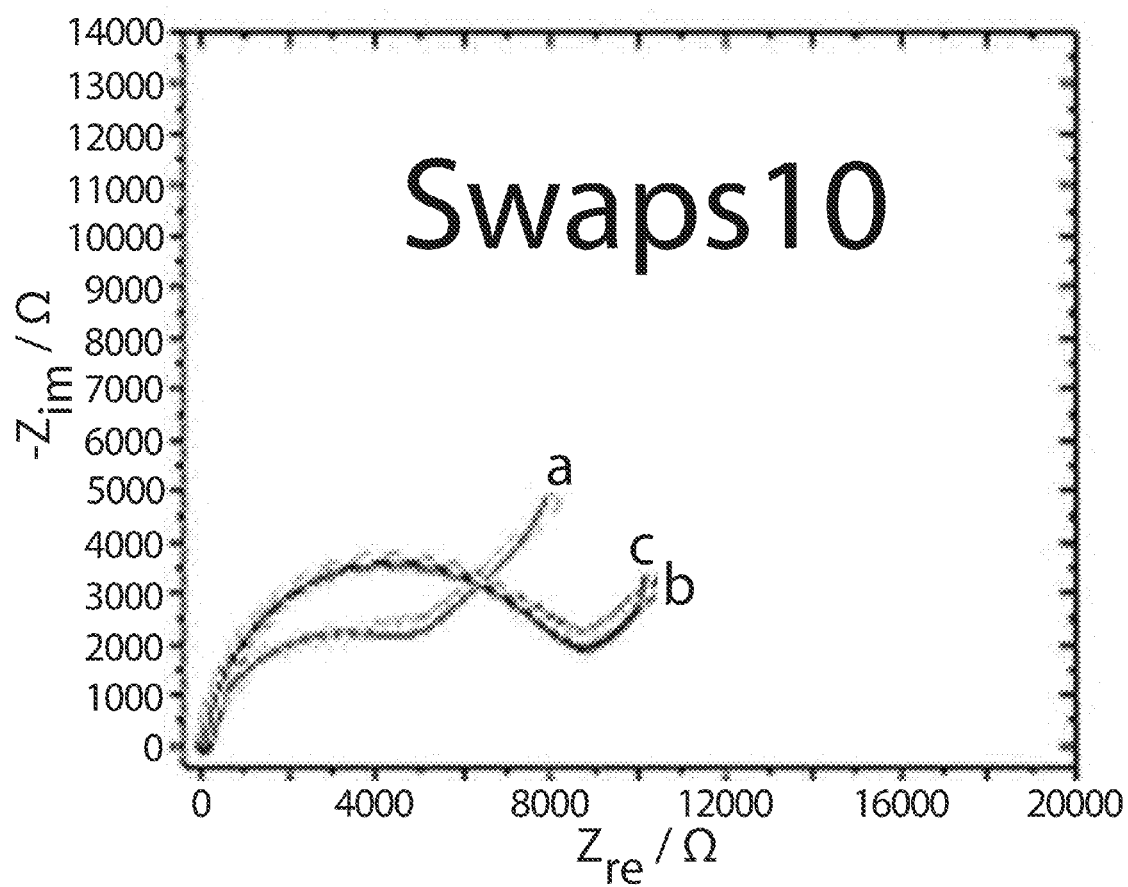
Figure 6K:
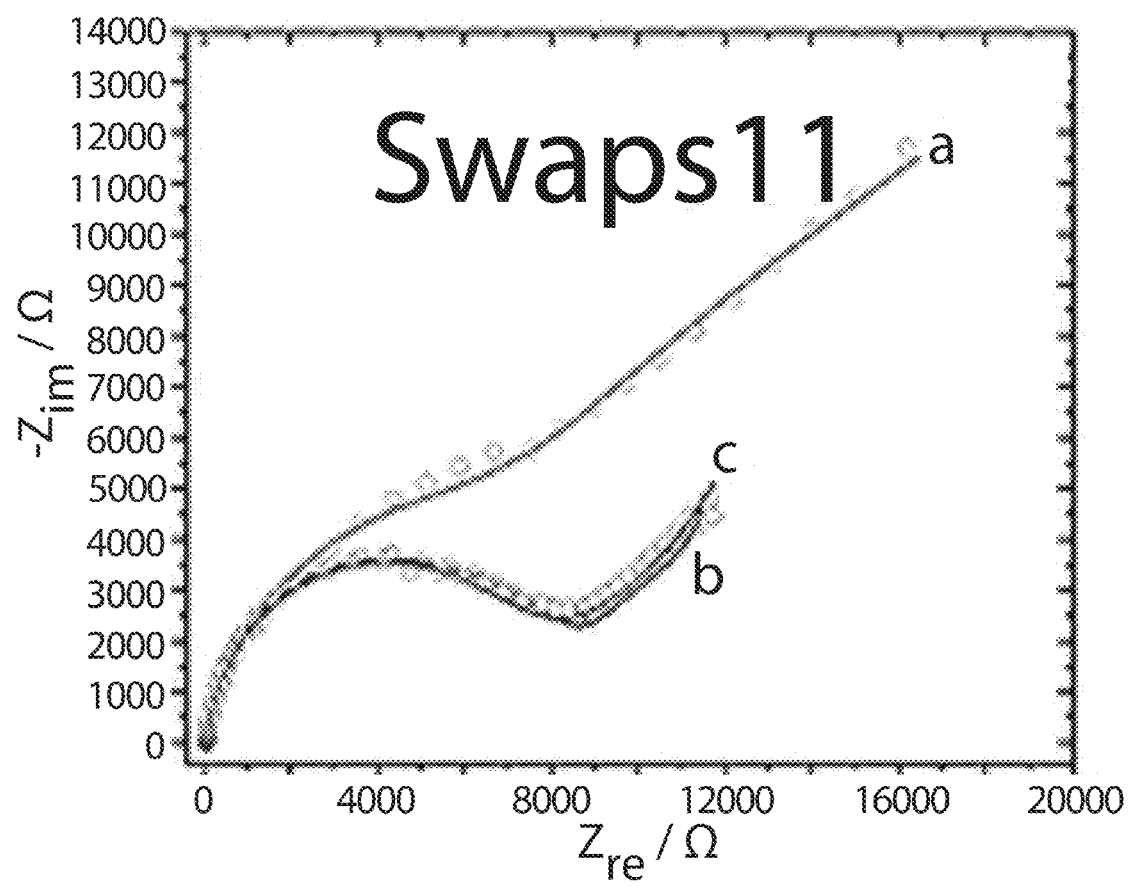
Figure 6L:
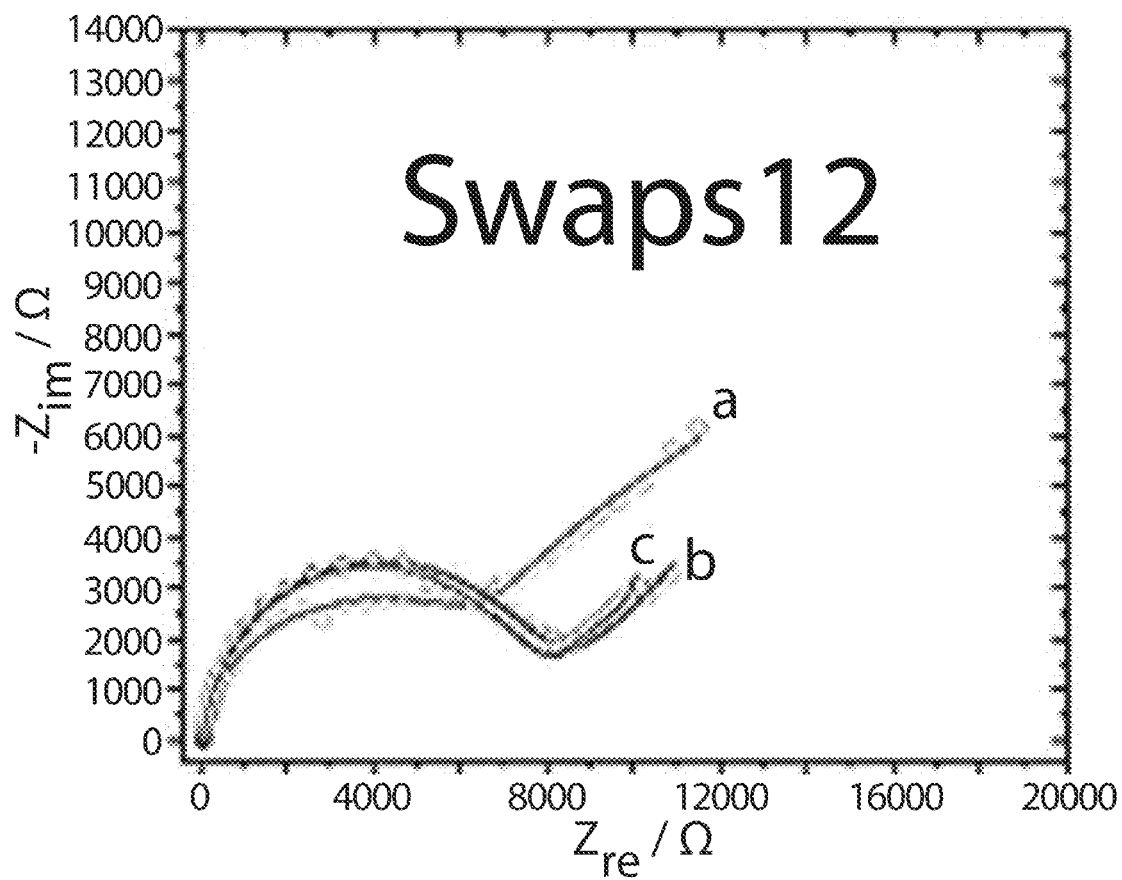
Figure 6M:
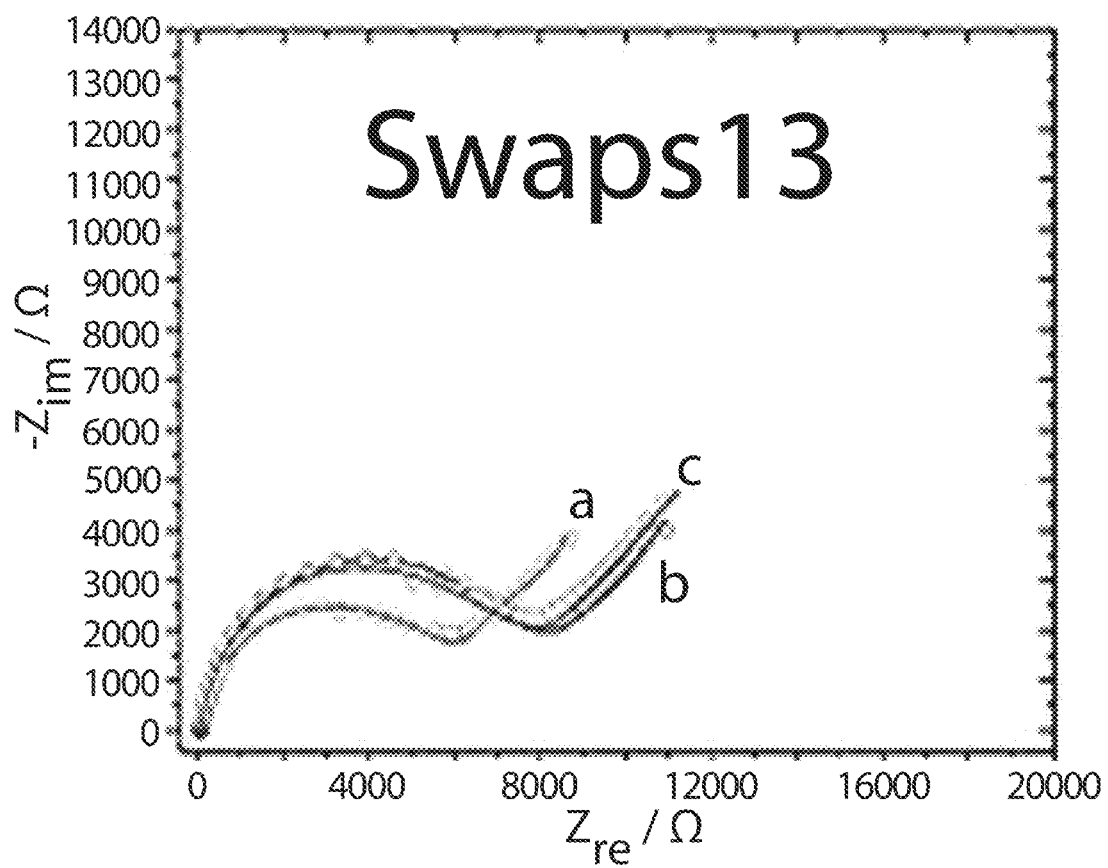
Figure 6N:
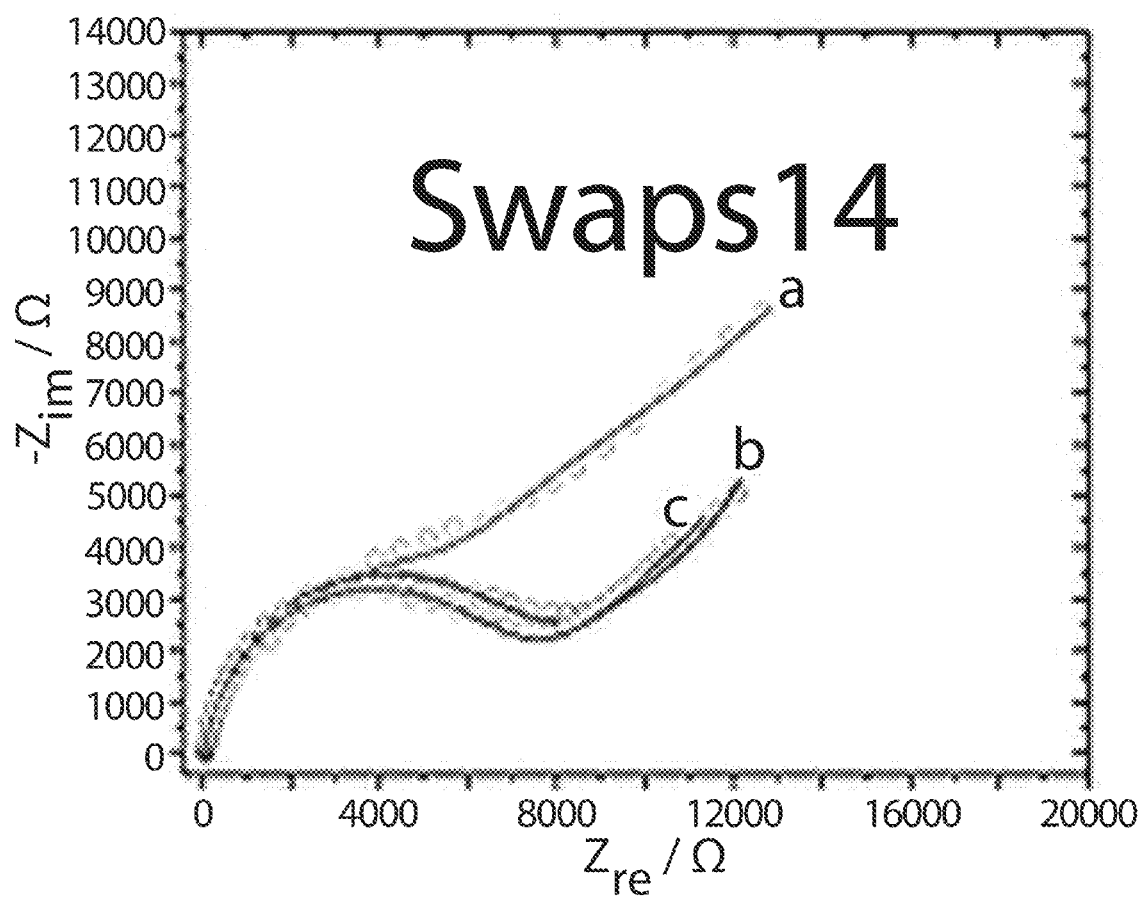
Figure 6O:
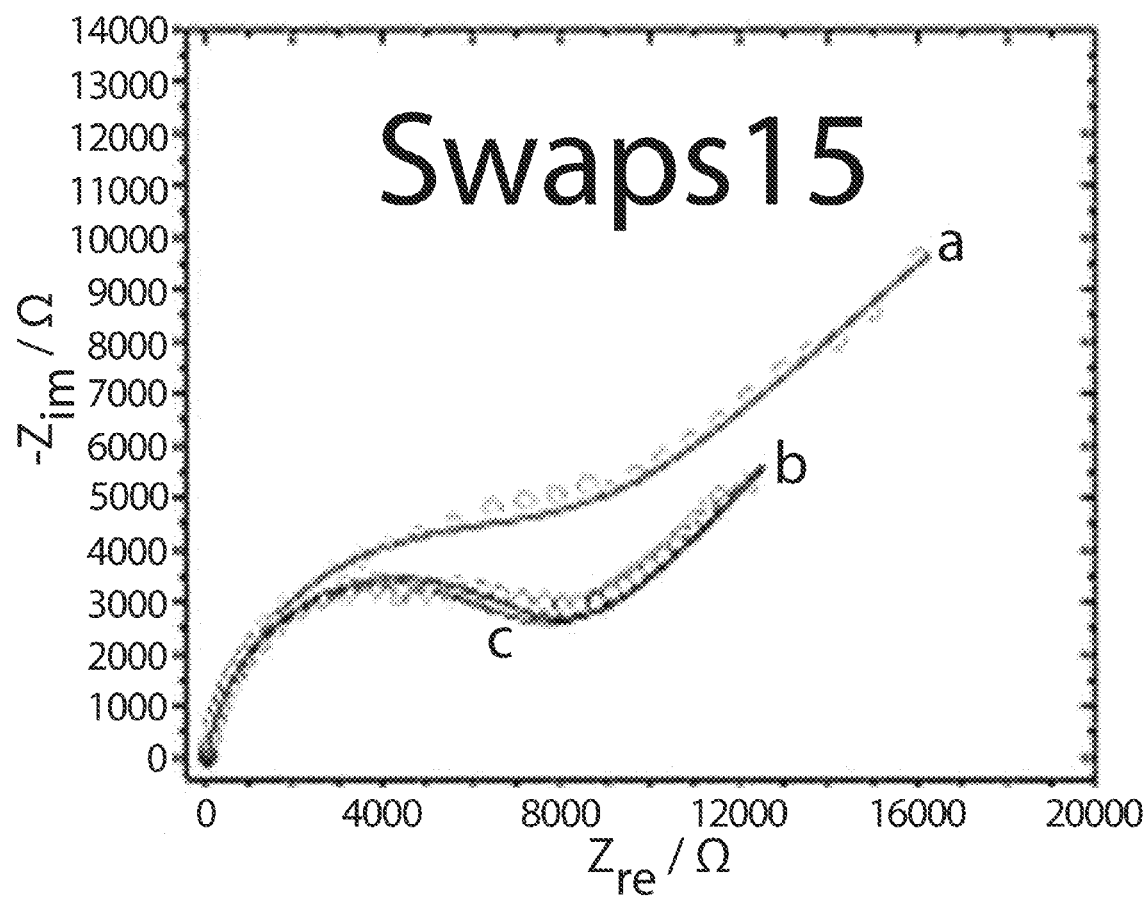
Figure 6P:
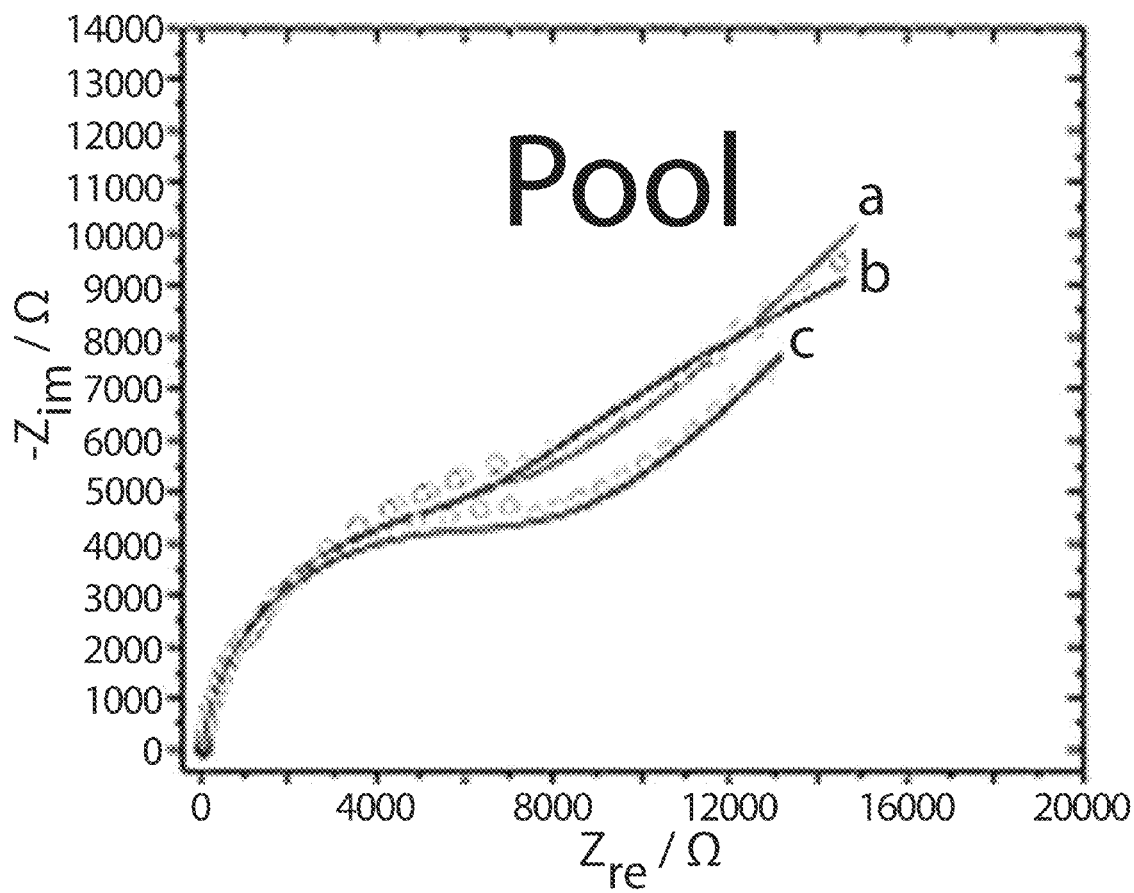

The electrochemical characteristics of the developed impedimetric sensor is provided in FIG. 5 and Table 1.

TABLE 1

Equivalent circuit element values for the developed aptasensor after each modification step

| | Rs (Ω) | CPE (μF) | n | $R_{CT}$ (Ω) | W ($\mu F^{0.5}$) |
|---|---|---|---|---|---|
| Bare electrode | 74.17 | 4.95 | 0.85 | 5710 | 118 |
| After formation of the thiolated hybrid | 73.7 | 2.56 | 0.91 | 6710 | 125 |
| After surface backfilling with 2-mercaptoethanol | 70.18 | 3.04 | 0.92 | 7631 | 170 |

The rationale behind this electrochemical approach is that the binding between the virus and the respective aptamer, will further block the charge transfer from the solution-based redox probe to the electrode surface. Consequently, $R_{CT}$ will become increasingly high and can be used to monitor the binding event (Ayyar et al.; Wei et al.). A schematic representation of the sensor preparation and performance is provided in FIG. 4A. A hybrid of a thiol-modified primer and the SwAp was self-assembled onto a gold nanoparticles-modified screen-printed carbon electrode. Binding of VSV to the immobilized SwAp, in the presence of $Ca^{2+}$ and $Mg^{2+}$, causing an increase in the interfacial resistance from the baseline value $R_{CTB}$ to $R_{CTV}$. Incubation with a mixture of EDTA and EGTA causes a switch in the aptamer conformation with a subsequent release of VSV and a shift-back in the interfacial resistance to $R_{CTS}$.

More specifically, incubation of $1\times10^6$ PFU of VSV in Dulbecco's phosphate buffered saline (DPBS) with the respective SwAp immobilized onto the electrode surface for 1 hour at room temperature, caused an increase in the interfacial resistance and consequently in the value of $R_{CT}$. Fifteen aptamer sequences were tested and the affinity between the virus and each sequence was expressed as the change in $R_{CT}$ value, which is calculated from the difference between $R_{CT}$ after incubation with the virus ($R_{CTV}$) and the baseline resistance obtained after the preparation of the aptasensor, $R_{CTB}$. Afterward, each aptasensor was incubated with an equimolar mixture of EDTA and EGTA (50 mM) for 30 min at room temperature. As can be seen in FIG. 4B and FIG. 6, treatment with the EDTA/EGTA mixture caused a decrease in impedance. This could be ascribed to the chelation of the $Ca^{2+}$ and $Mg^{2+}$ ions, which in turn caused a change in the conformation of the SwAp and consequently forced the virus to dissociate from its complex with the immobilized SwAp leading to a parallel shift-back in impedance. FIG. 6 shows Nyquist plots ($-Z_{im}$, vs. $Z_{re}$) of impedance spectra of VSV aptasensors based on 15 aptamer clones (Swaps1→Swaps15) obtained (a) after aptasensor preparation (b) after binding of 1×10⁶ PFU of VSV in Dulbecco's phosphate buffered saline (DPBS), and (c) after treatment with an equimolar mixture of EDTA and EGTA (50 mM). A control experiment was performed, under the same conditions, using the original aptamer pool utilized in selection. The impedance spectra were recorded from 100 kHz to 0.1 Hz and the amplitude was 0.25 V vs. Ag pseudo-reference in 25 mM sodium phosphate buffer (pH 7), containing 2.5 mM $K_4[Fe(CN)_6]$ and 2.5 mM $K_3[Fe(CN)_6]$.

Figure 4:
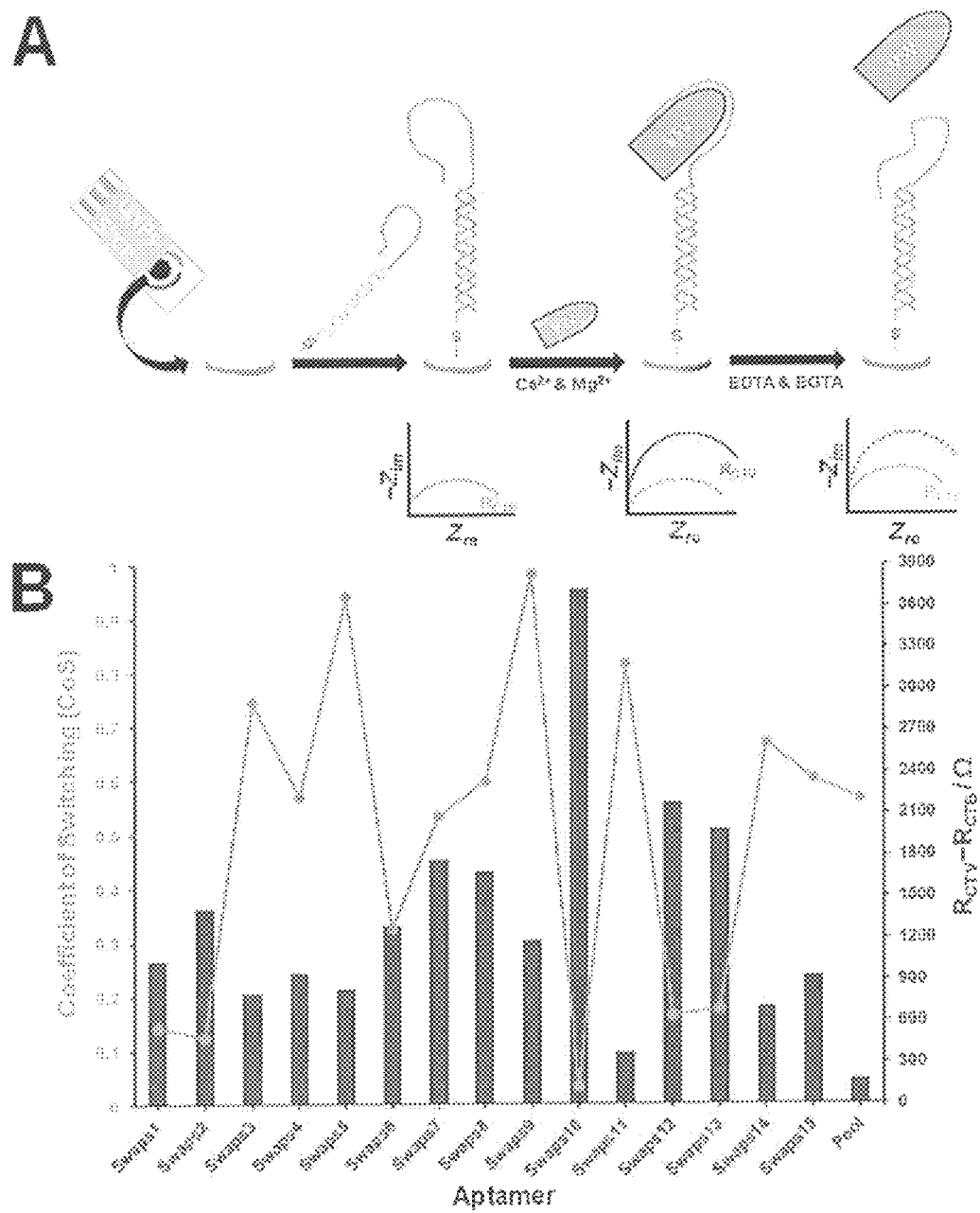
FIG. 4A is a schematic diagram of the electrochemical sensor developed to measure the affinities of the developed SwAps to VSV and the coefficient of switching.
FIG. 4B is a plot of the change of resistance to charge transfer (RCT) after VSV binding (aff target. In other embodiments, the unbound SwAps are separated by washing or elution from target and target-aptamer complexes immobilized on a surface. The SwAps are then amplified, for example by polymerase chain reaction (PCR), thereby enriching the SwAps within the aptamer pool. These amplified SwAps can then be re-isolated any number of times to further enrich the aptamer pool for SwAps with switchable affinity to the target.

The switching ability of each SwAp can be expressed as the Coefficient of Switching (CoS), which can be calculated from the formula 2:

$$CoS = 1 - \left(\frac{RCTS - RCTB}{RCTV - RCTB}\right) \quad (2)$$

Where $R_{CTS}$ represents the resistance to charge transfer after aptamer switching due to EDTA/EGTA treatment. A control experiment was performed, under the same conditions, using the original aptamer pool employed in selection. The circuit elements calculated for each SwAp are provided in Table 2. In FIG. 4B, the control experiment was performed under the same conditions, using the original aptamer pool utilized in selection.

TABLE 2

Equivalent circuit element values for the developed aptasensors using different SwAps, where $SwAp_B$, $SwAp_V$, and $SwAp_S$ represents the circuit elements before VSV binding, after incubation with 1 × 10⁶ PFU of VSV, and after regeneration using EDTA/EGTA, respectively.

| | $R_s$ (Ω) | CPE (µF) | n | $R_{CT}$ (Ω) | W (µF^0.5) |
|---|---|---|---|---|---|
| SwAp$_B$1 | 74.02 | 2.26 | 0.92 | 6691 | 185 |
| SwAp$_V$1 | 72.6 | 1.8 | 0.94 | 7729 | 173 |
| SwAp$_S$1 | 73.49 | 1.78 | 0.94 | 7581 | 200.5 |
| SwAp$_B$2 | 71.81 | 6.14 | 0.86 | 5731 | 202.6 |
| SwAp$_V$2 | 70.58 | 3.43 | 0.91 | 7149 | 168.8 |
| SwAp$_S$2 | 71.54 | 2.9 | 0.91 | 6794 | 181.4 |
| SwAp$_B$3 | 75.45 | 3.32 | 0.9 | 7822 | 117.4 |
| SwAp$_V$3 | 74.85 | 7.76 | 0.87 | 8625 | 7.067 |
| SwAp$_S$3 | 72.27 | 3.34 | 0.9 | 8027 | 110.1 |
| SwAp$_B$4 | 70.87 | 2.69 | 0.91 | 7016 | 80.35 |
| SwAp$_V$4 | 71.78 | 2.68 | 0.91 | 7971 | 90.02 |
| SwAp$_S$4 | 70.03 | 3.82 | 0.9 | 7427 | 88.04 |
| SwAp$_B$5 | 73.6 | 4.72 | 0.91 | 6551 | 91.37 |

TABLE 2-continued

Equivalent circuit element values for the developed aptasensors using different SwAps, where $SwAp_B$, $SwAp_V$, and $SwAp_S$ represents the circuit elements before VSV binding, after incubation with 1 × 10⁶ PFU of VSV, and after regeneration using EDTA/EGTA, respectively.

| | $R_s$ (Ω) | CPE (µF) | n | $R_{CT}$ (Ω) | W (µF^0.5) |
|---|---|---|---|---|---|
| SwAp$_V$5 | 75.18 | 2.05 | 0.93 | 7389 | 191.5 |
| SwAp$_S$5 | 72.59 | 2.14 | 0.93 | 6601 | 176.8 |
| SwAp$_B$6 | 71.96 | 4.4 | 0.9 | 6625 | 113.1 |
| SwAp$_V$6 | 72.36 | 2.22 | 0.93 | 7917 | 177.6 |
| SwAp$_S$6 | 74.45 | 2.47 | 0.92 | 7497 | 213 |
| SwAp$_B$7 | 74.93 | 3.42 | 0.9 | 7574 | 241.8 |
| SwAp$_V$7 | 73.99 | 2.05 | 0.93 | 9346 | 319.6 |
| SwAp$_S$7 | 73.21 | 2.34 | 0.93 | 8400 | 268.7 |
| SwAp$_B$8 | 70.15 | 8.07 | 0.87 | 5454 | 184.3 |
| SwAp$_V$8 | 68.52 | 3.74 | 0.9 | 7132 | 185.6 |
| SwAp$_S$8 | 69.52 | 3.54 | 0.9 | 6128 | 188.1 |
| SwAp$_B$9 | 71.12 | 3.12 | 0.91 | 6931 | 168.8 |
| SwAp$_V$9 | 71.24 | 12.48 | 0.9 | 8111 | 87.31 |
| SwAp$_S$9 | 67.6 | 3.39 | 0.91 | 6952 | 156 |
| SwAp$_B$10 | 73.83 | 8.77 | 0.87 | 4321 | 202.8 |
| SwAp$_V$10 | 73.21 | 3.46 | 0.9 | 8043 | 325.5 |
| SwAp$_S$10 | 72.16 | 3.15 | 0.91 | 7923 | 309.3 |
| SwAp$_B$11 | 73.09 | 9.43 | 0.92 | 7269 | 81.4 |
| SwAp$_V$11 | 73.47 | 2.31 | 0.93 | 7642 | 200 |
| SwAp$_S$11 | 71.8 | 2.41 | 0.93 | 7338 | 185.5 |
| SwAp$_B$12 | 70.73 | 4.88 | 0.9 | 5495 | 147.9 |
| SwAp$_V$12 | 74.75 | 2.22 | 0.92 | 7670 | 272.9 |
| SwAp$_S$12 | 72.96 | 2.11 | 0.93 | 7314 | 289.8 |
| SwAp$_B$13 | 72.1 | 3.9 | 0.91 | 5269 | 243.2 |
| SwAp$_V$13 | 73.61 | 2.19 | 0.93 | 7253 | 228.5 |
| SwAp$_S$13 | 72.38 | 2.12 | 0.93 | 6905 | 200.5 |
| SwAp$_B$14 | 73.6 | 13.11 | 0.86 | 6590 | 111.7 |
| SwAp$_V$14 | 71.41 | 2.29 | 0.93 | 7299 | 168 |
| SwAp$_S$14 | 72.33 | 2.48 | 0.92 | 6825 | 197.3 |
| SwAp$_B$15 | 71.67 | 2.91 | 0.9 | 6940 | 165.8 |
| SwAp$_V$15 | 72.75 | 5.89 | 0.9 | 7870 | 95.6 |
| SwAp$_S$15 | 70.65 | 2.89 | 0.91 | 7310 | 164.9 |
| Pool$_B$ | 70.28 | 9.05 | 0.93 | 7248 | 95.31 |
| Pool$_V$ | 72.35 | 12.12 | 0.92 | 7430 | 103.4 |
| Pool$_S$ | 72.12 | 8.26 | 0.93 | 7327 | 129.3 |

As can be seen in Table 3, the values of $R_{CTV}$-$R_{CTB}$ and CoS were determined for each aptamer sequence and both parameters were employed to assess the efficiency of each SwAp for VSV purification. In other words, SwAps exhibiting high virus affinity and switching ability, including SwAps clones 9, 5, 7 and 3, have the potential to be further integrated into affinity chromatography units involved in VSV purification. A slight variation of the results obtained using the impedimetric sensor was observed when compared to the flow cytometry data. This could be ascribed to the different forms of aptamers used in each method where free aptamers were used in flow cytometry, whereas immobilized aptamers were used to develop the sensors. Thus, they may adopt different tertiary structures and alter their binding capabilities.

TABLE 3

Sequences of switchable aptamers, their affinities to VSV expressed as the change in charge transfer resistance after binding to the virus ($R_{CTV}$-$R_{CTB}$), and coefficient of switching (CoS) where F: 5'CTCCTCTGACTGTAACCACG3' (SEQ ID NO: 1) and R: 5'GCATAGGTAGTCCAGAAGCC3' (SEQ ID NO: 2)

| Clone | Sequence | ($R_{CTV}$-$R_{CTB}$) (Ω) | Coefficient of Switching (CoS) |
|---|---|---|---|
| SwAp1 SEQ ID NO: 3 | F-CGC CCT CAG AAC TTT TGT ATC CGA ACA CCT GCA TCG TCC G-R | 1038 | 0.14 |

TABLE 3 -continued

Sequences of switchable aptamers, their affinities to VSV expressed as the change in charge transfer resistance after binding to the virus ($R_{CTV}$-$R_{CTB}$), and coefficient of switching (CoS) where F: $^{5'}$CTCCTCTGACTGTAACCACG$^{3'}$ (SEQ ID NO: 1) and R: $^{5'}$GCATAGGTAGTCCAGAAGCC$^{3'}$ (SEQ ID NO: 2)

| Clone | Sequence | ($R_{CTV}$-$R_{CTB}$) ($\Omega$) | Coefficient of Switching (CoS) |
|---|---|---|---|
| SwAp2 SEQ ID NO: 4 | F-TAC CAC CCG TGA CGC GCA CAT CCC TCC TCT GTT CTC CGC G-R | 1418 | 0.12 |
| SwAp3 SEQ ID NO: 5 | F-TGC CCC CTC CAT CCC GAG TAA CCT ACG TCC ATG TCT CGC T-R | 803 | 0.74 |
| SwAp4 SEQ ID NO: 6 | F-TGC CCC CTC CAT CCC GAG TAA CCT ACG TCC ATG TCT CGC T-R | 955 | 0.57 |
| SwAp5 SEQ ID NO: 7 | F-TAC CAC CCG TGA CCC TCA CAT CCC TCC TCT GTT CTC CGC G-R | 838 | 0.94 |
| SwAp6 SEQ ID NO: 8 | F-TGG CAC TGT TGT CAT CAC TGT CCC CCC CTA ACT CGT CCG T-R | 1292 | 0.33 |
| SwAp7 SEQ ID NO: 9 | F-TAC CAC CCG TGG CCC TCA CAT CCC TCC TCT GTT CTC CGC G-R | 1772 | 0.53 |
| SwAp8 SEQ ID NO: 10 | F-TAC CAC CCG TGA CCC TCA CAT CCC TCC TCT GAC GTA ACC ACG CG-R | 1678 | 0.6 |
| SwAp9 SEQ ID NO: 11 | F-TAC CAC CCG TGGCCC TCA CAT CCC TCC TCT GTT CTC CGC G-R | 1180 | 0.98 |
| SwAp10 SEQ ID NO: 12 | F-TAC CGC CCG TGA CCC TCA CAT CCC TCC TCT GTT CTC CGC G-R | 3722 | 0.03 |
| SwAp11 SEQ ID NO: 13 | F-CAG CCA CCA TAC TGT CCC GTT TGC CCC CGC CGA TTC CGT C-R | 373 | 0.82 |
| SwAp12 SEQ ID NO: 14 | F-TAC CAC CCG TGA CCC TTA CAT CCC TCC TCT GTT CTC CGC G-R | 2175 | 0.16 |
| SwAp13 SEQ ID NO: 15 | F-TAC CAC CCG TGA CCC TCA CAT CCC TCC TCT GTT CTC CGC G-R | 1984 | 0.18 |
| SwAp14 SEQ ID NO: 16 | F-TAC CAC CCT TGA CCC TCA CAT CCC TCC TCT GTT CTC CGC G-R | 709 | 0.67 |
| SwAp15 SEQ ID NO: 17 | F-GCA CCC CGA GGC AAT TTC GCG CAT AGT TCA TCC TGT TTG G-R | 930 | 0.6 |
| Pool 10 SEQ ID NO: 18 | F-NNN NNN NNN NNN NNN NNN NNN NNN NNN NNN NNN NNN-R | 182 | 0.57 |

Example 7

Electrochemical Characterization of the Developed SwAps

The electrochemical characteristics of the developed aptasensor were investigated by both CV and EIS. As shown in FIG. 5A, the pretreated electrode presents a quasi-reversible voltammogram indicating that the redox reactions easily occurred on the bare electrode surface, evidenced by the large redox currents (curve a). Formation of SAM of the thiolated primer (capture probe) hybridized with the VSV-specific SwAp (detection probe) on the electrode surface significantly reduced the electrode current; also the sigmoidal behaviour observed in curve b could be indicative of limited charge transfer via tunnelling or diffusion through the defects in the formed layer. Moreover, the repulsion between the negatively charged DNA backbone and the redox probe, $[Fe(CN)_6]^{3-/4-}$, is responsible of the significant reduction of the redox currents. Final treatment with 2-mercaptoethanol greatly reduced the redox currents because they can penetrate down to the electrode surface, thereby blocking the direct access of the conducting ions (curve c). The Nyquist plots of the impedance spectra are shown in FIG. 5B and the circuit element values are presented in Table 1, which support the CV data. The complex impedance was presented as the sum of the real Z, $Z_{re}$, and imaginary Z, $Z_{im}$, components that originate mainly from the resistance and capacitance of the electrical cell, respectively. A suitable equivalent circuit, shown in the inset of FIG. 5B, was carefully selected to express the electrochemical process and to enable fit producing accurate values. A modified Randles circuit consists of the ohmic resistance; $R_S$, of the electrolyte solution, the electronic charge transfer resistance, $R_{CT}$, in series with the finite length Warburg W, and in parallel with a constant phase element, CPE, associated with the double layer and reflects the interface between the assembled film and the electrolyte solution. The solution resistance, $R_S$, is the resistance between the aptamer-modified electrode and the reference electrode. The high frequency semicircle of the Nyquist diagram corresponds to the charge transfer resistance, $R_{CT}$, in parallel with the CPE. The former represents the electron-transfer kinetics of the redox probe at the electrode surface, whereas the latter corresponds to a non-linear capacitor accounting for the inhomogeneity of the formed film (Fitzgerald et al.). The diameter of the semicircle corresponds to the interfacial resistance at the electrode surface, the value of which depends on the dielectric and insulating features of the surface layer. On the other hand, the Warburg impedance, $Z_W$, accounts for a diffusion-limited electrochemical process, presumably due to molecular motions within the film caused by conducting ions penetration (Yang et al.).

Example 8

Effects of Buffer on Binding

Figure 7:
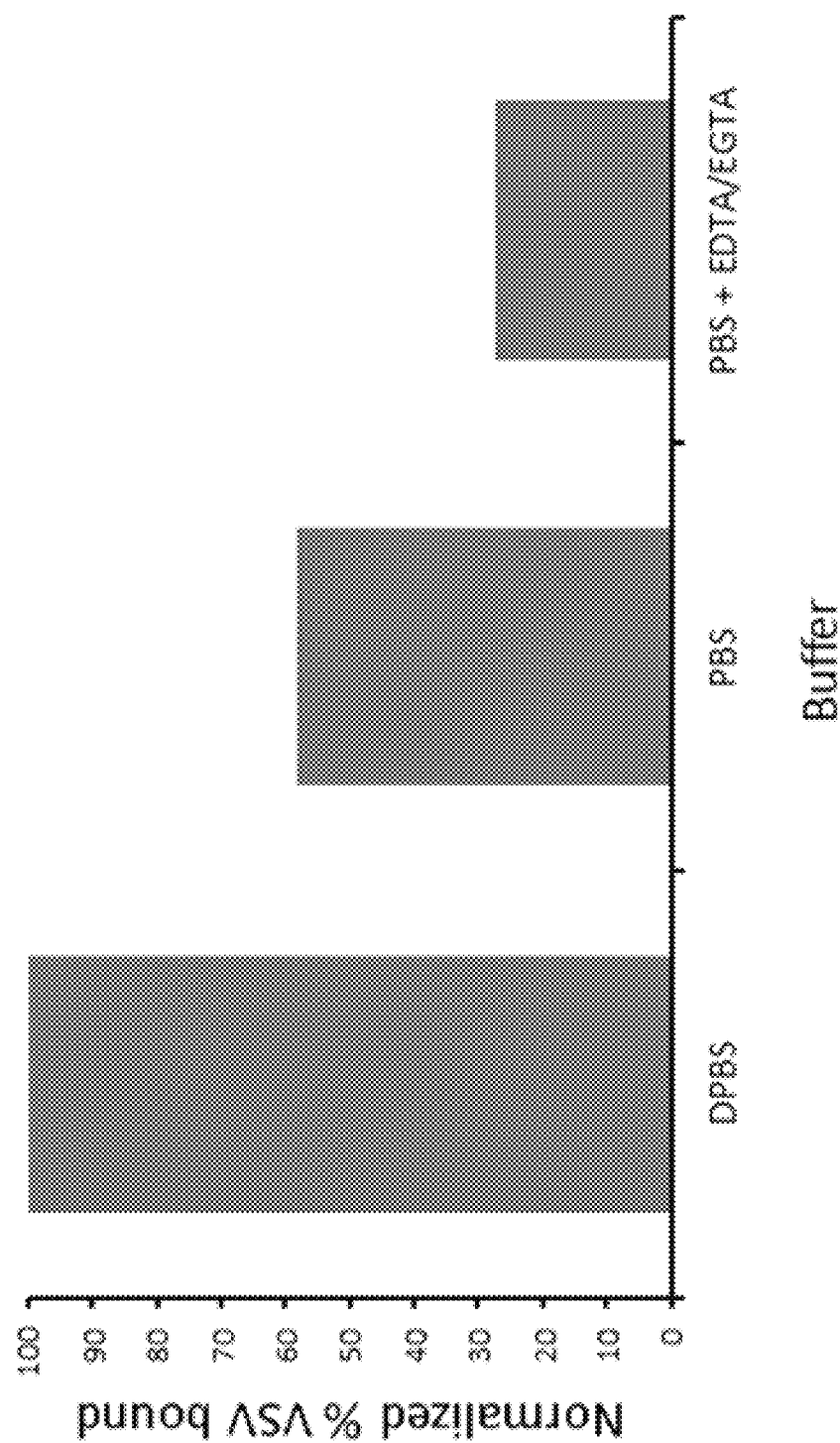

The switching ability of aptamer pools was hypothesized to stem from the removal of $Ca^{2+}$ and $Mg^{2+}$ which can bind to phosphate backbone of ssDNA. To confirm that this was indeed the case and not the result of a change in buffer ionic strength, a flow cytometric analysis was performed as shown in FIG. 7. More specifically, FIG. 7 is a bar chart of the binding affinity of SwAp6 clone in different buffers. Aptamers (50 nM) incubated with VSV ($10^7$ PFU) for 30 min prior to separation into 3 fractions. Each 50 µL fraction was mixed with 250 µL of DPBS ($MgCl_2$ and $CaCl_2$), PBS or PBS with 10 mM EDTA/EGTA. SwAps clone 6 was allowed to bind to VSV for 30 minutes and then separated and incubated in 3 different buffers. Results were obtained using flow cytometry and measuring fluorescence of the virus particles. It was observed that the amount of VSV bound to the SwAps has increased significantly in the presence of divalent cations. However, in instances when divalent cations were not present in the buffer such as in PBS, the amount of virus bound to aptamer decreases. Finally, in PBS containing 10 mM of EDTA/EGTA, the amount of bound VSV was the lowest due to the chelation of the divalent cations. This trend has been noted before by others, where the effects of ionic strength and pH were examined with respect to aptamer-protein binding (Jiang et al.).

Example 9

SwAps-Based Purification of VSV

Briefly, FIG. 1B shows a schematic representation of virus purification by SwAps in accordance with the method of the present disclosure.

In a low DNA binding tube, 200 nM of 5,6,7 and 9 clones were mixed together with either biotin-labeled forward ($^{5'}$CGTGGTTACAGTCAGAGGAG$^{3'}$/3Biotin) (SEQ ID NO: 19) or reverse (5Biosg/$^{5'}$GGCTTCTGGACTACCTATGC$^{3'}$) (SEQ ID NO: 20) complementary primers. An annealing protocol was used to hybridize the probes as follows; heat to 95° C. for 2 min and then gradually decrease the temperature to 20° C. by 1° C. every 3 sec. Streptavidin-coated magnetic beads (Cat#Z5482, Promega, U.S.) were used for the purification procedure. Briefly, 1 mL of beads was added to low DNA binding tube and the buffer was exchanged with penicillin-streptomycin (P4333, Sigma-Aldrich, U.S.) and incubated for 2 hrs at 37° C. The beads were then washed with sterile DPBS, followed by the addition of 200 nM aptamer clone mixture and incubation at 25° C. for 2 hrs (shaking every 10 min to resuspend beads). A magnetic stand (Z5331, Promega, U.S.) was used to separate the beads from the aptamer mixture and the beads were then washed 3 times with DPBS. A mixture of VSV and cell debris collected from the VSV harvesting procedure was mixed with aptamer-bead complex for 1 hr. Subsequently, the beads were washed 3 times with DPBS followed by the addition of 25 mM EDTA/EGTA and incubation for 30 min at 25° C. This allowed for the liberation of VSV which was examined using flow cytometry and viral plaque assays.

For the selection of SwAps with switchable affinity to VSV, the mixture of SwAps clones contained equal amount of 5, 6, 7, and 9 with either forward or reverse biotin primers. These clones were chosen because 5, 7 and 9 showed promising results when assessed using the developed aptasensors. The conjugation of SwAps to magnetic beads mimics the approach used for aptasensor analysis and thereby would suggest that the SwAps selected via electrochemical impedance spectroscopy would function well for purification. Although SwAps6 showed modest results in the aptasensor analysis, it was selected to be included among the best SwAps due to its superior performance in free form as indicated by the flow cytometry data.

Biotinylated aptamers (SwAps6) are conjugated to streptavidin coated magnetic beads and mixed with VSV and cell debris solution obtained from the virus harvesting protocol. SwAps bind to VSV. Debris is removed by washing the beads with DPBS. EDTA and EGTA are added to chelate the magnesium and calcium ions causing a conformational change which releases VSV. VSV is then collected.

Figure 8:
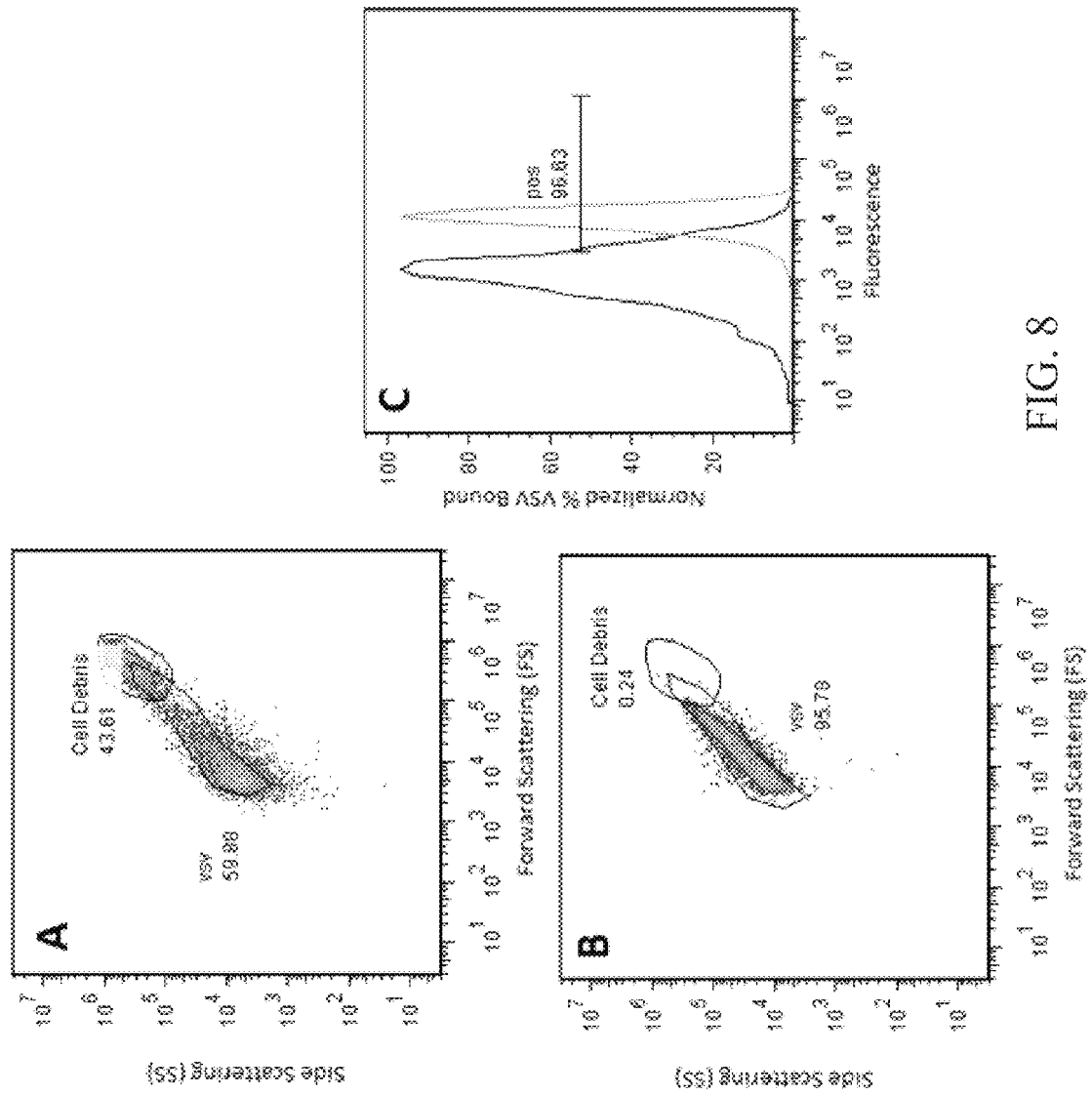

As shown in FIG. 8, flow cytometry was used to assess the ability of SwAps-coated magnetic beads to purify VSV from its mixture with cell debris. FIG. 8A shows the harvested VSV mixture which contained both the cell debris and VSV before purification. Upon incubation of the virus mixture with streptavidin-coated magnetic beads conjugated with a mixture of SwAps, one can see in FIG. 8B that pure VSV was obtained from the mixture. Finally, to ensure that the gate titled VSV did contain the virus, anti-VSV antibodies labeled with Alexa 547 was added and the fluorescence histogram of FIG. 8C clearly shows that VSV was collected. The SwAps clones have been selected so that they have an increased sensitivity to the loss of divalent cations, the switching property has been achieved with using 25 mM EDTA/EGTA. Thus, one limitation of this method is that the VSV collected is in a solution of EDTA/EGTA and may require an exchange of buffer for further use. Despite this limitation, the method has proven successful as a potential procedure to purify VSV from contaminating material and is re-usable as the aptamer can reform the tertiary structure when snap cooled (denatured and then cooled quickly to 4° C.) in DPBS.

Figure 9:
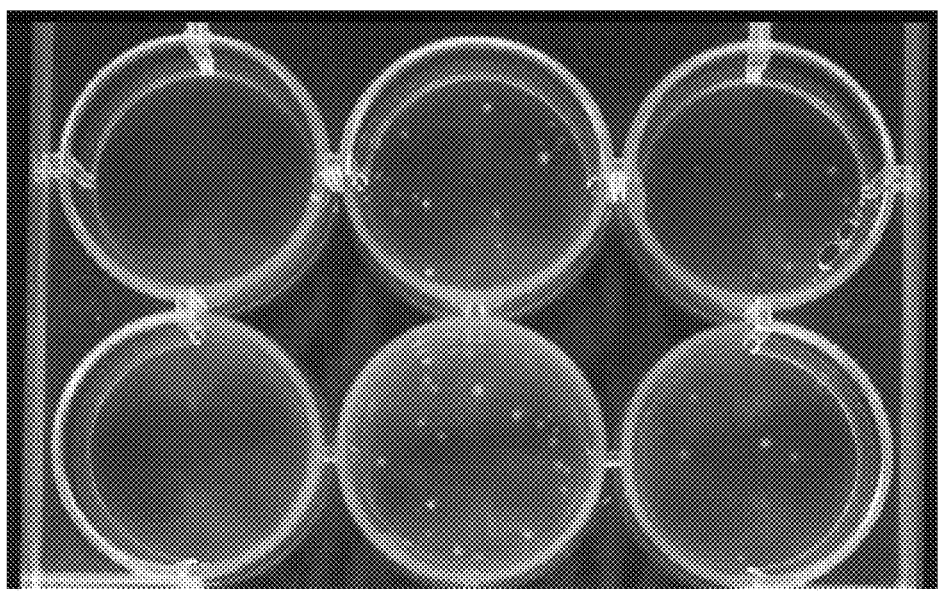
Figure 10A:
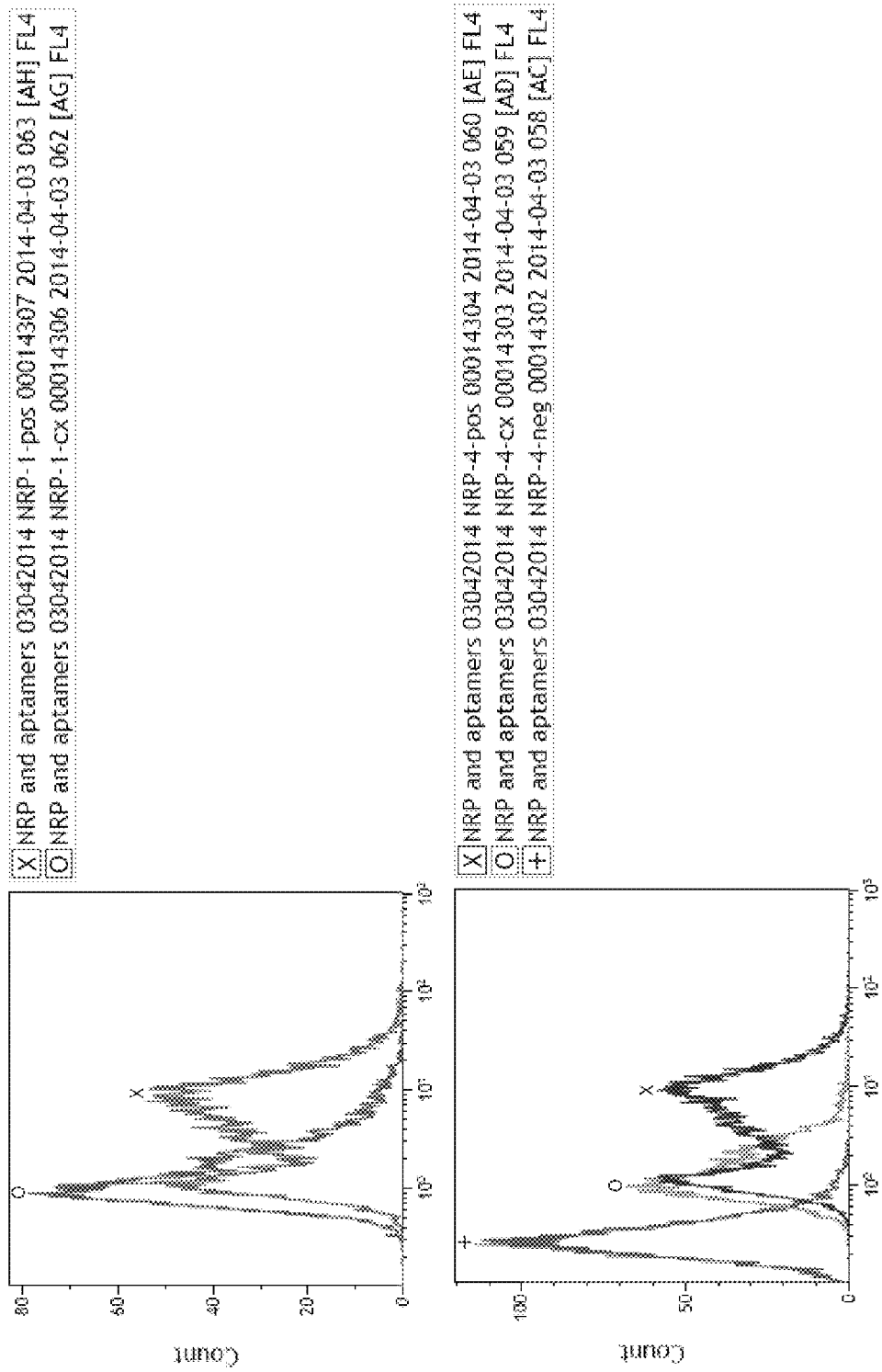
Figure 10B:
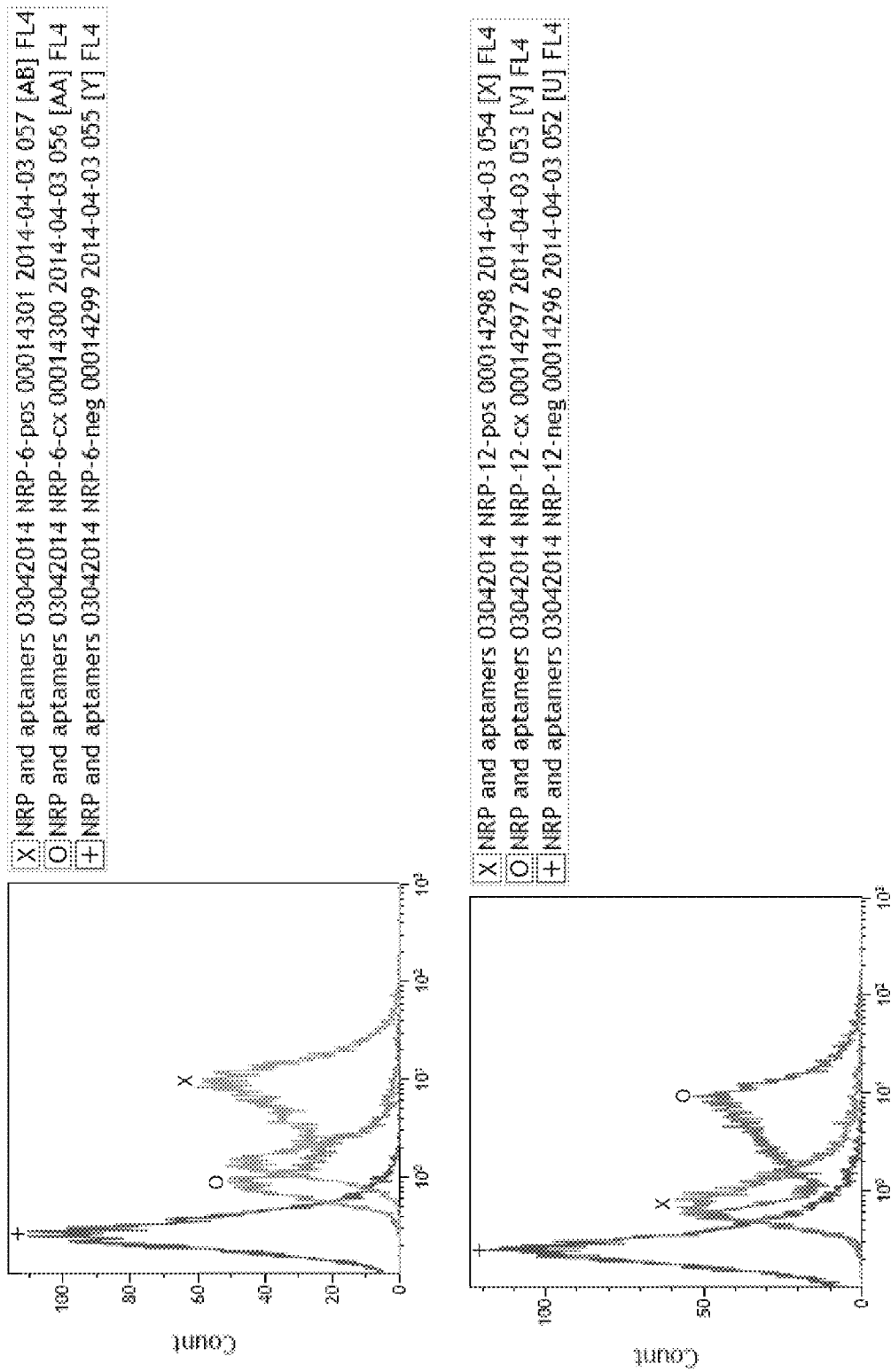
Figure 10C:
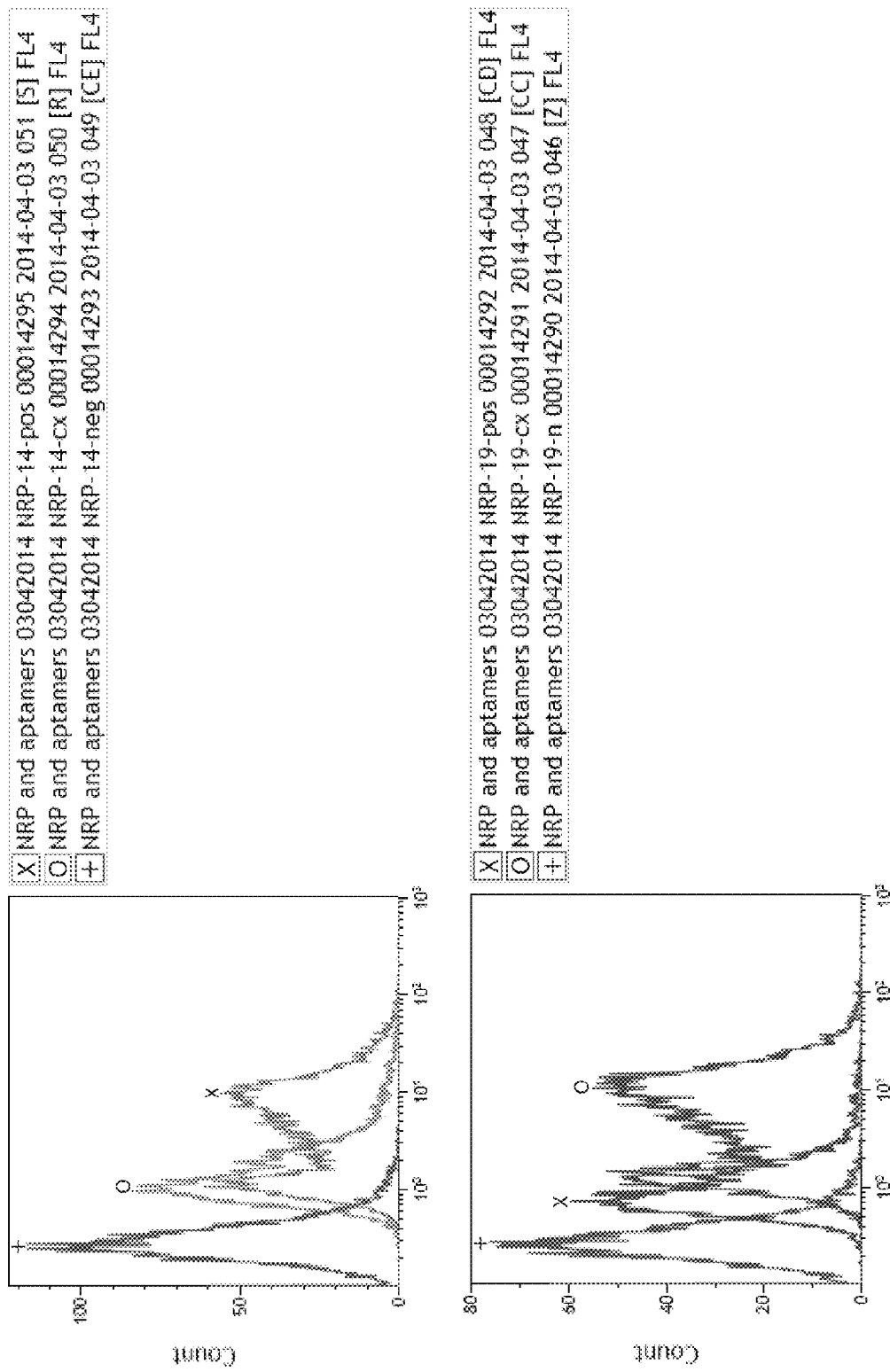
Figure 10D:
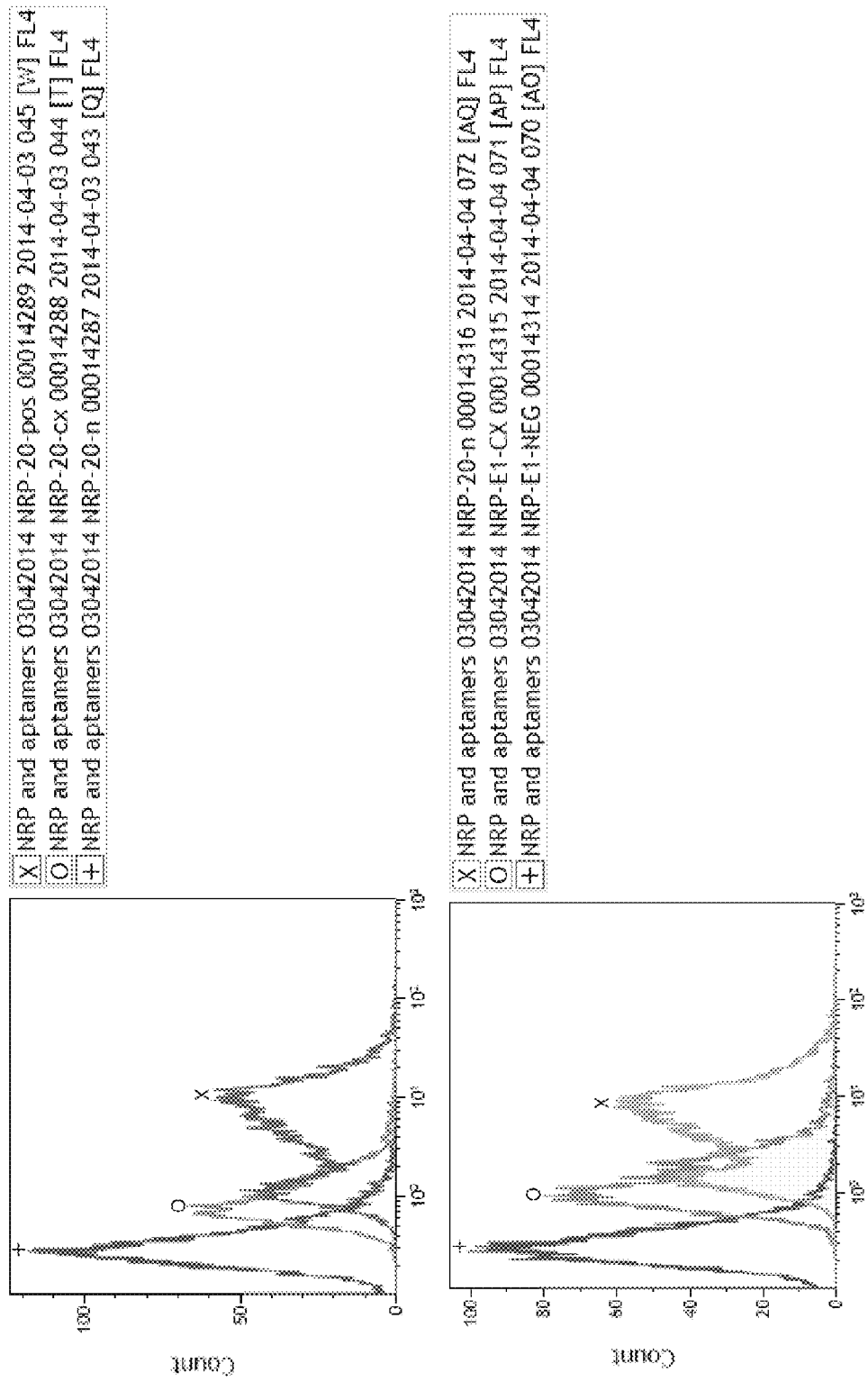
Figure 10E:
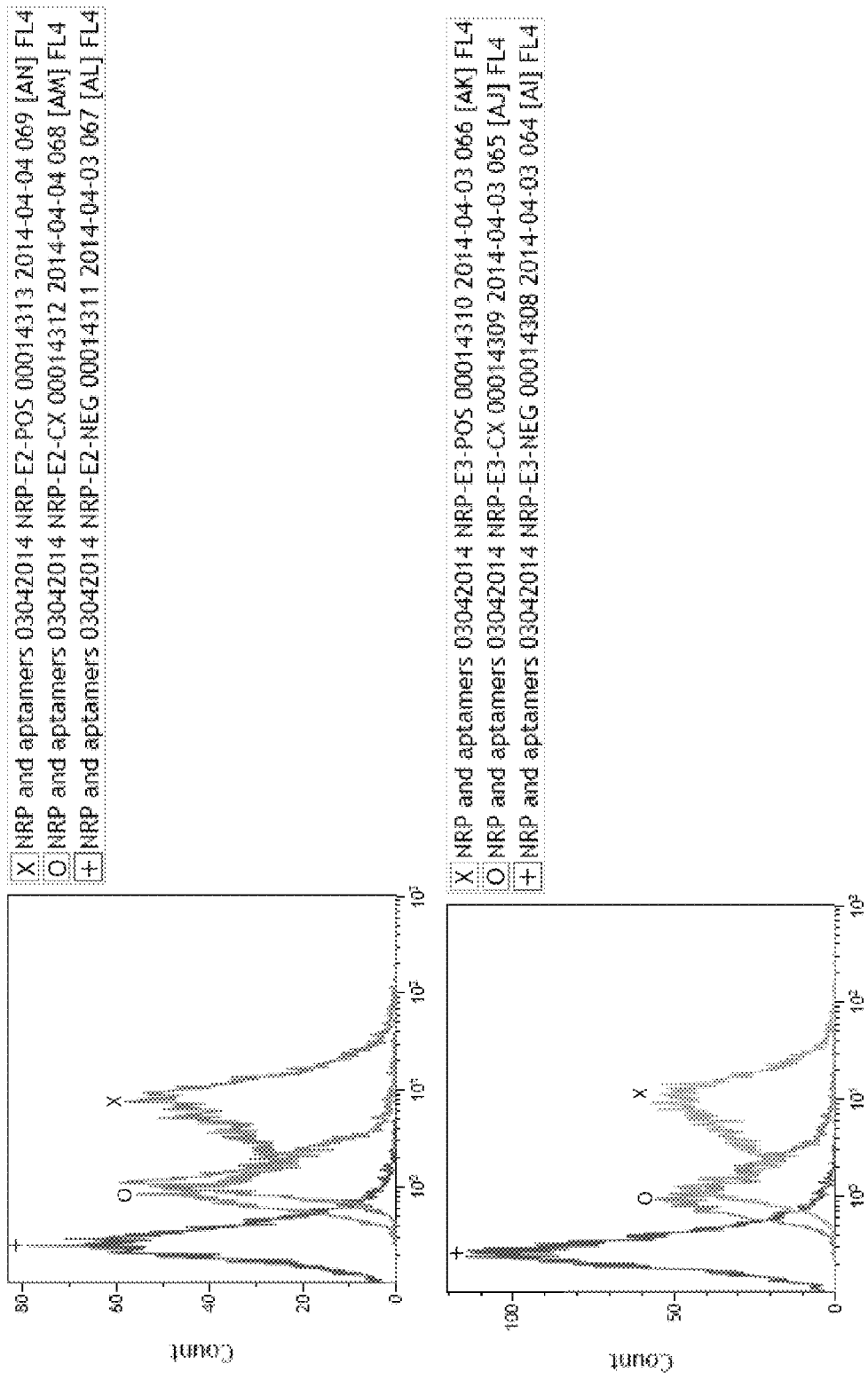
Figure 10F:
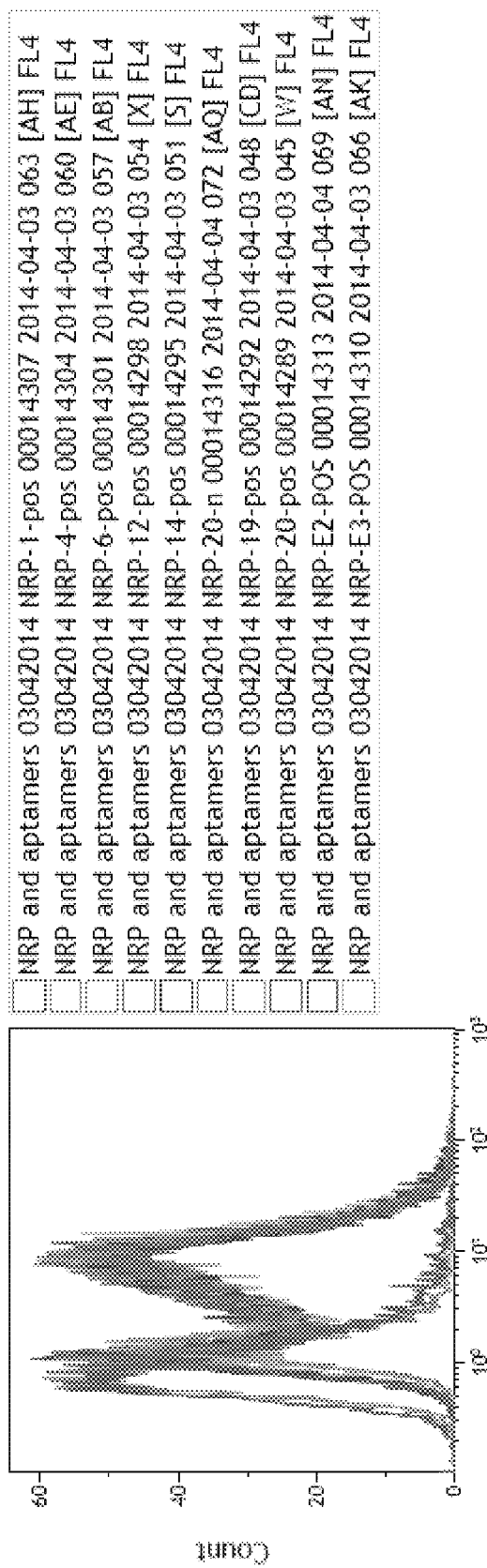
Figure 11A:
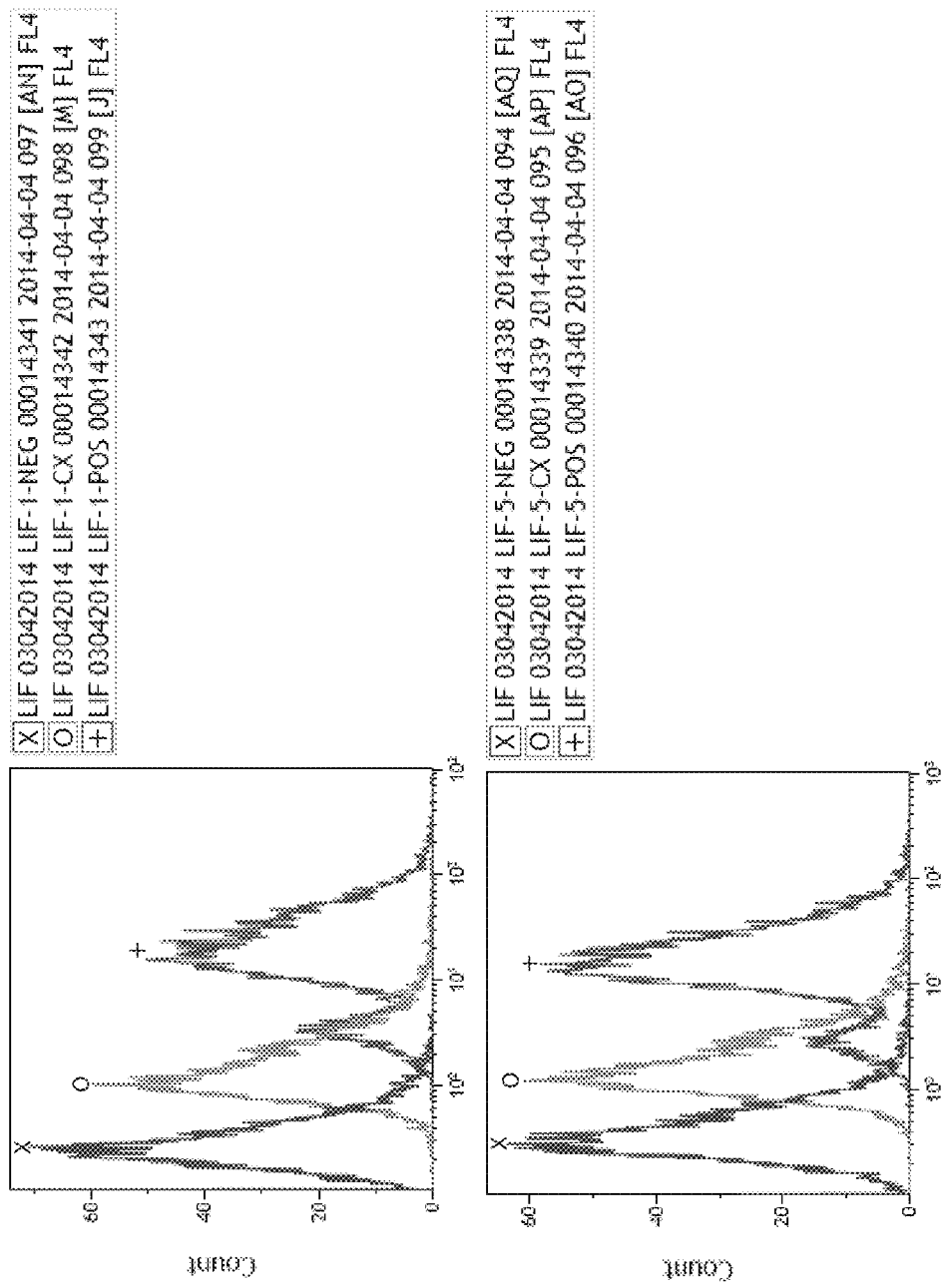
Figure 11B:
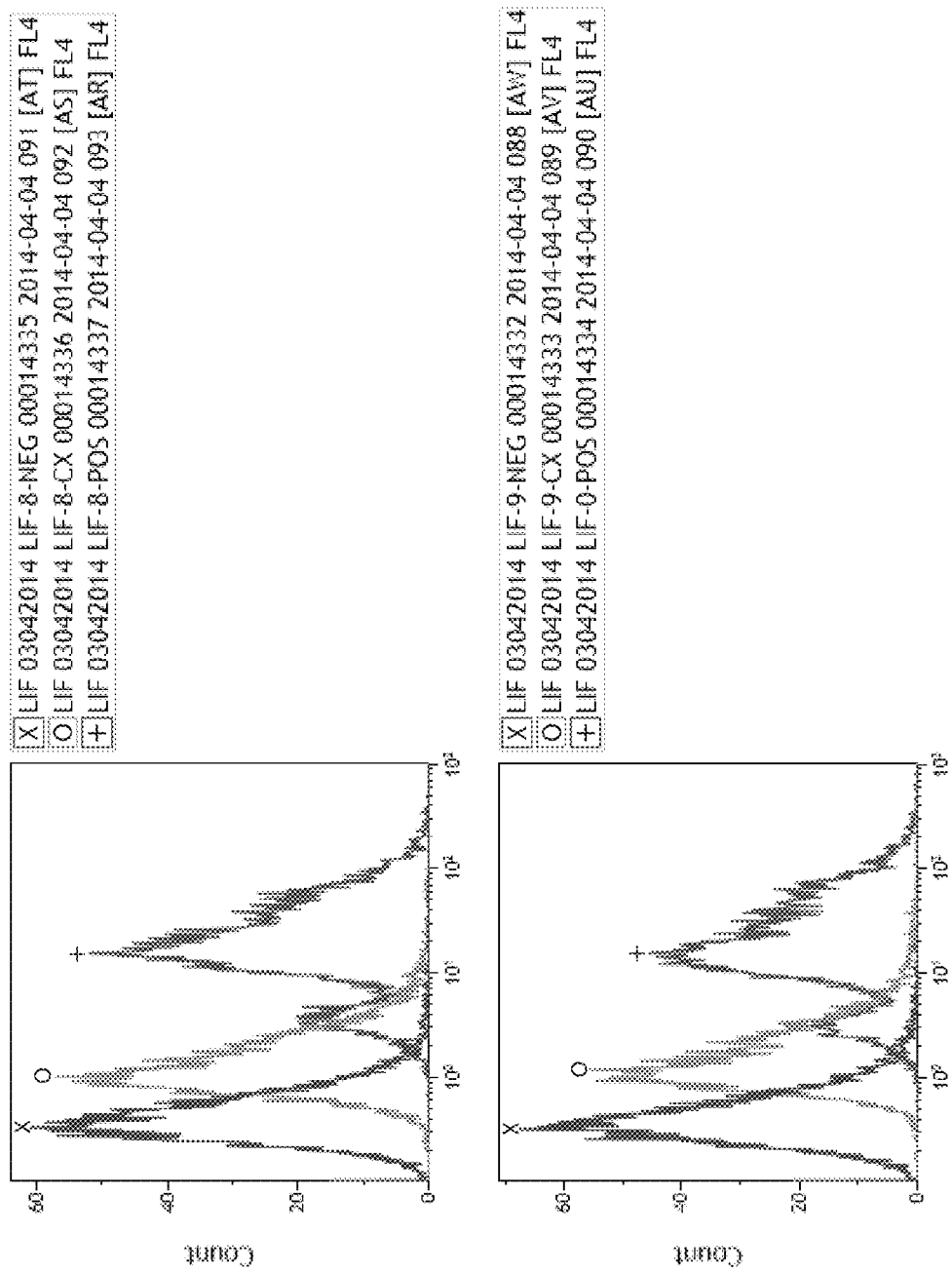
Figure 11C:
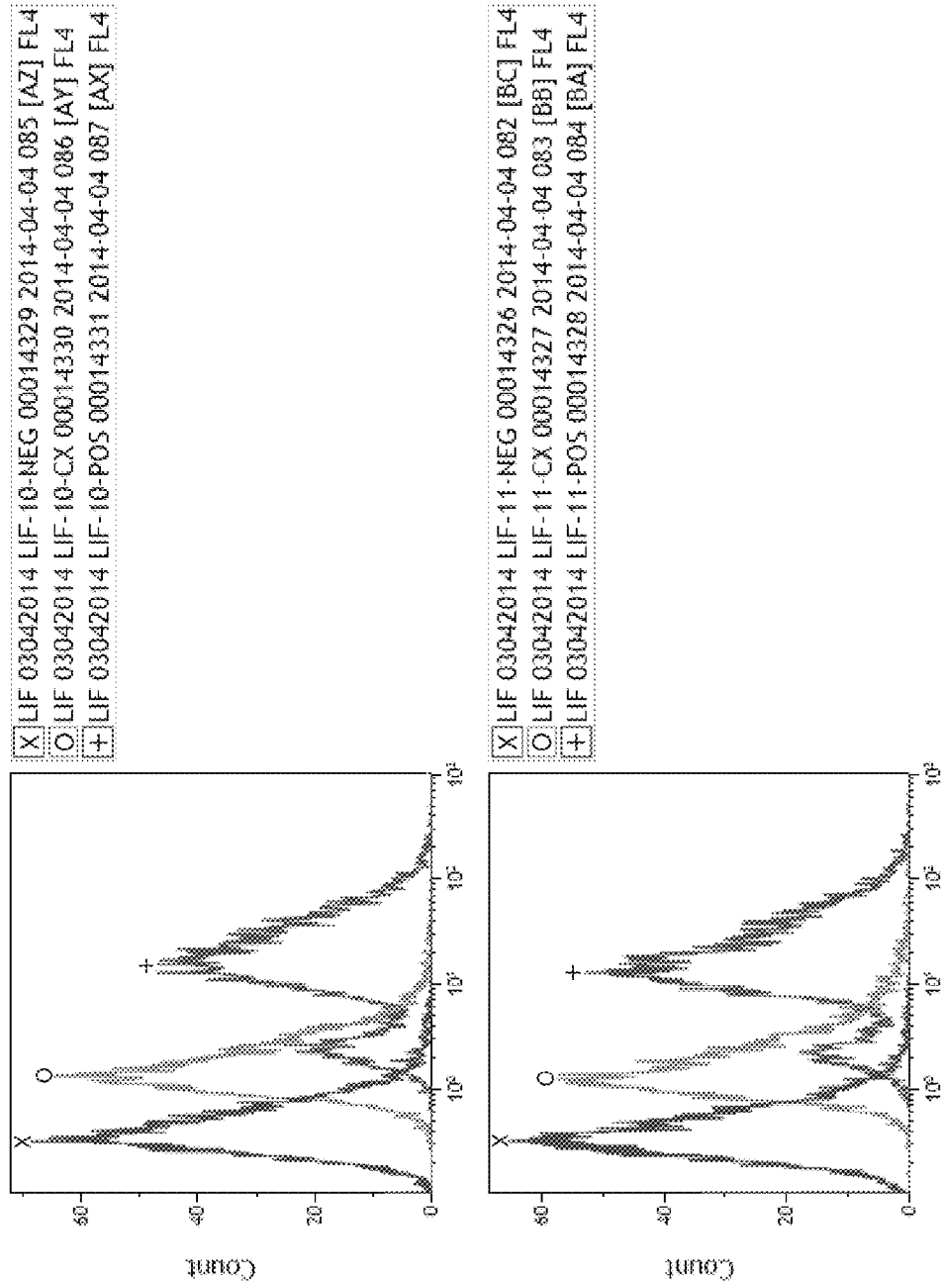
Figure 11D:
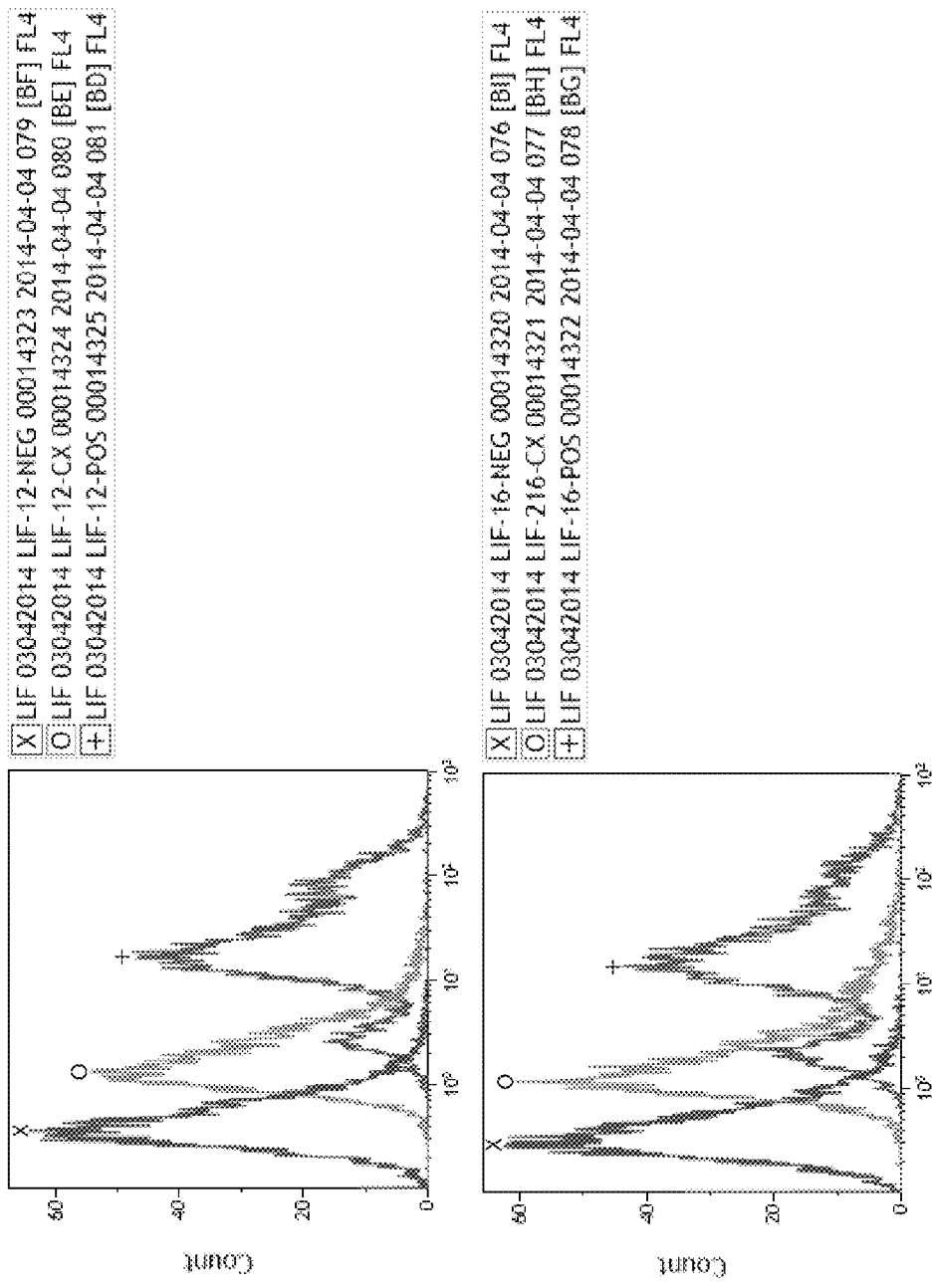
Figure 11E:
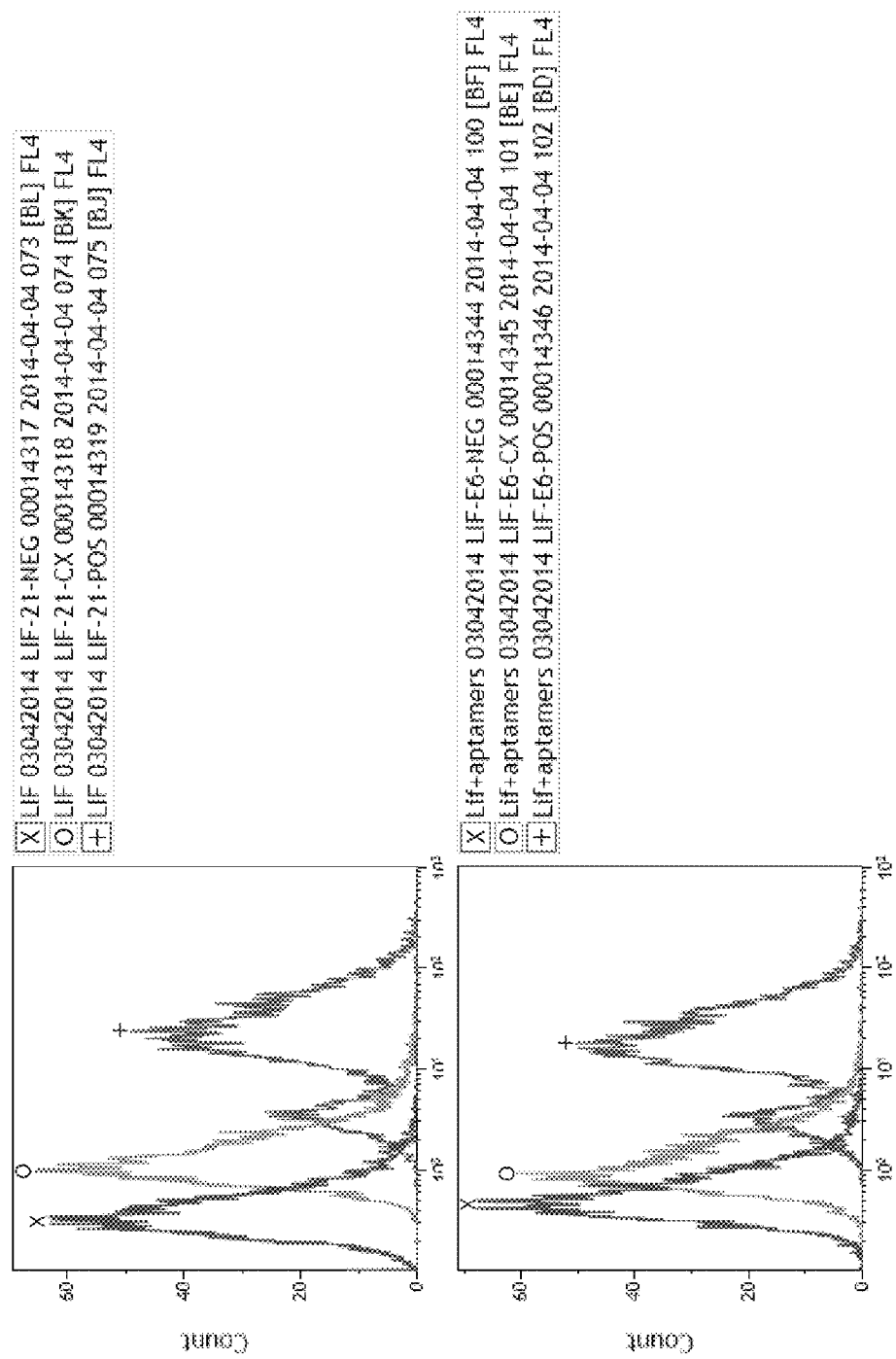
Figure 11F:
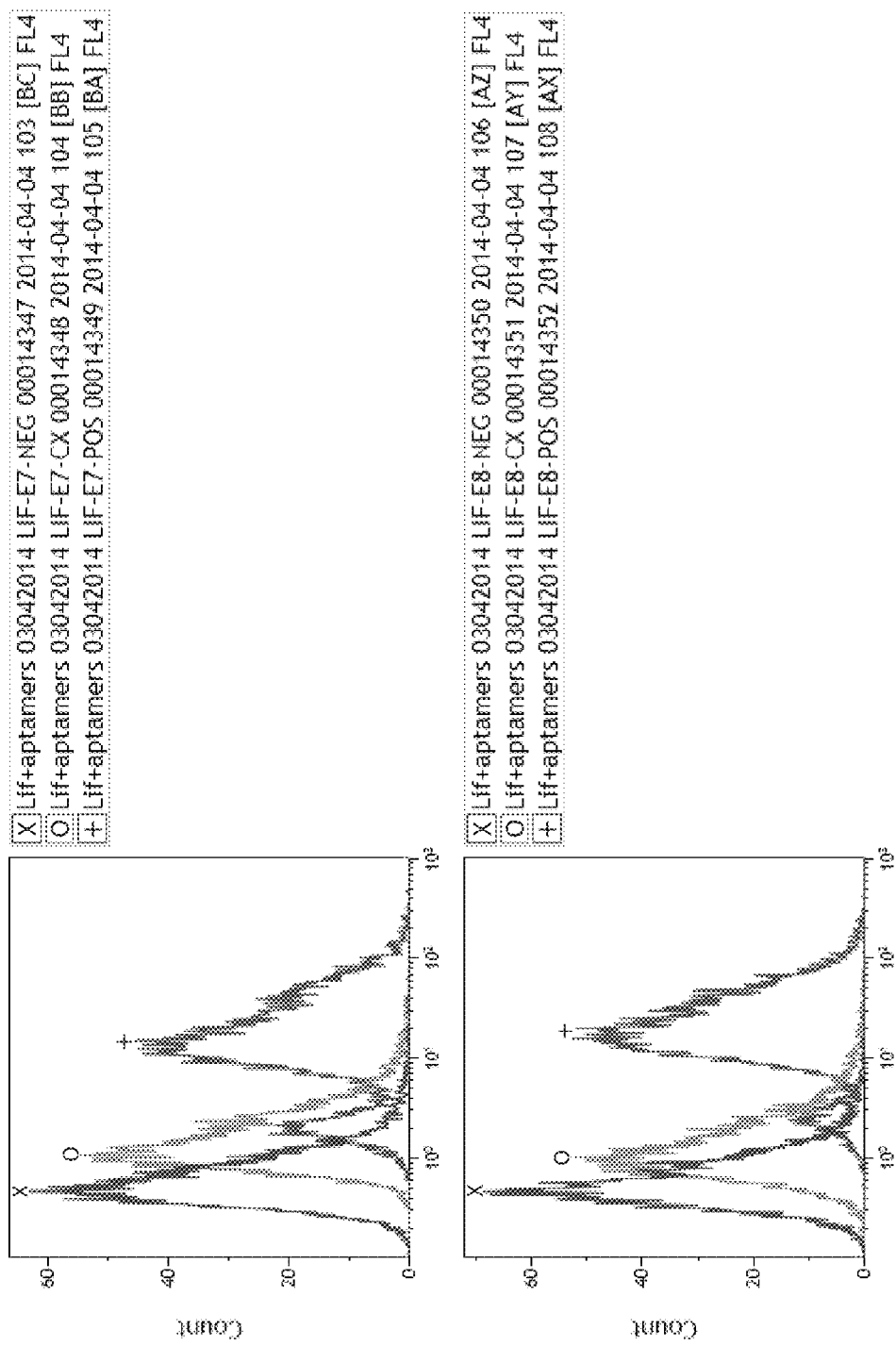
Figure 11G:
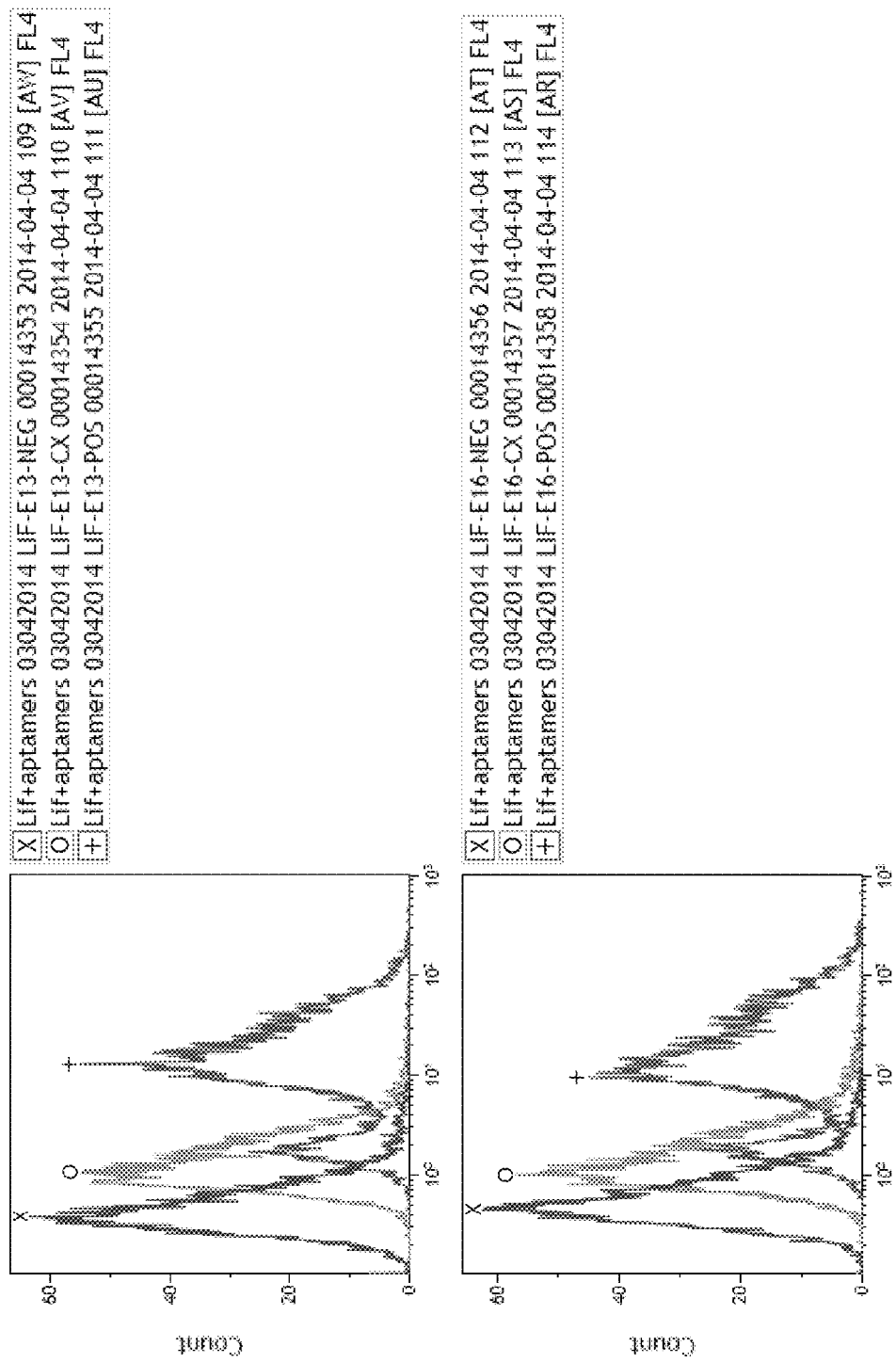
Figure 11H:
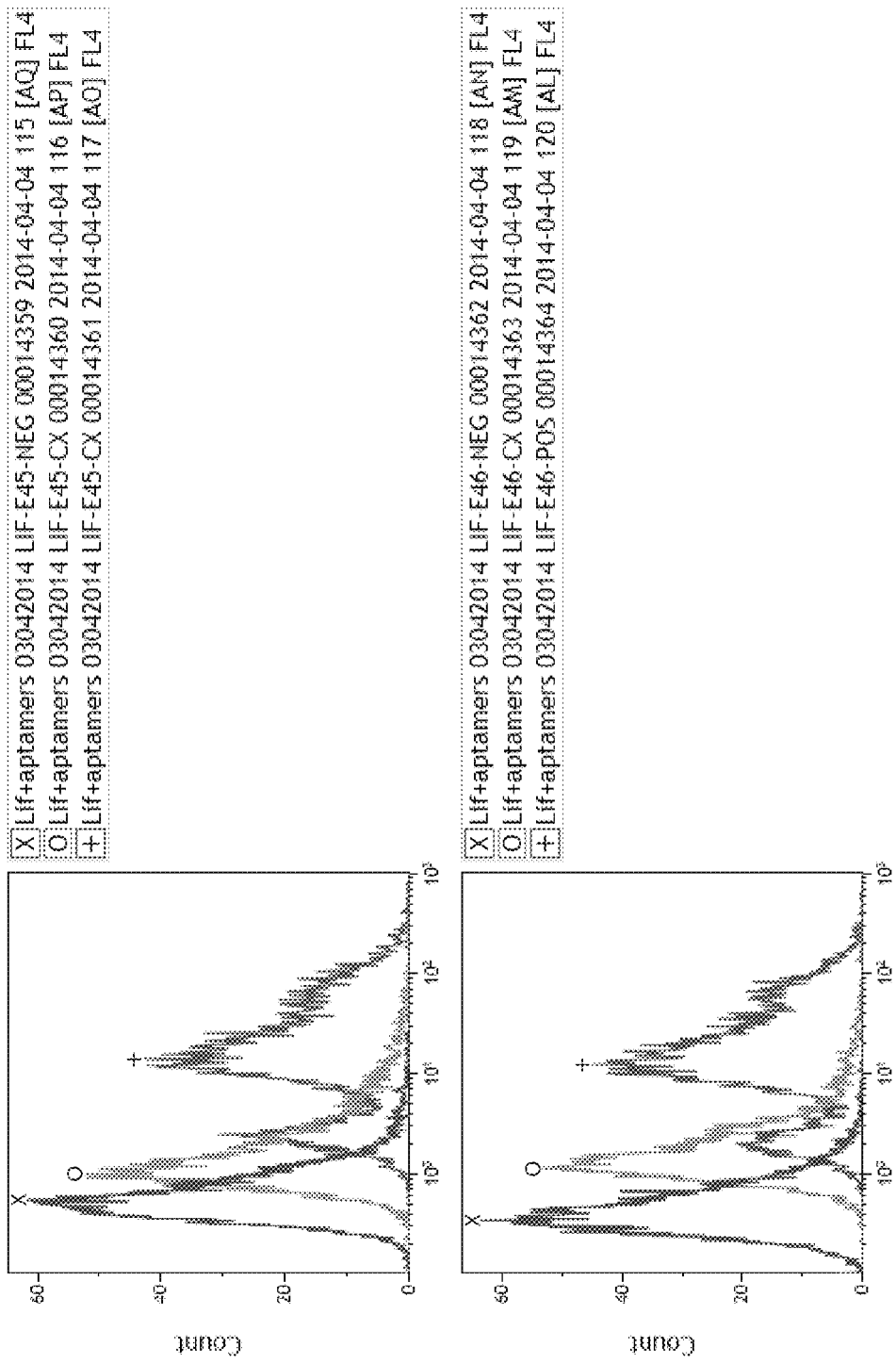
Figure 111:
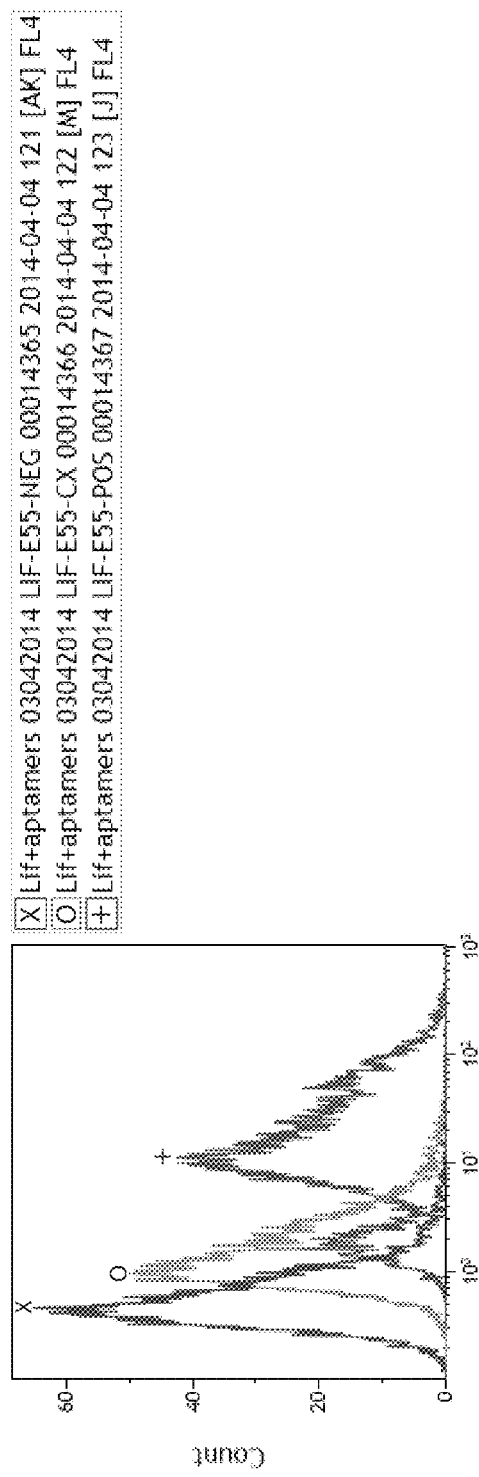
Figure 11J:
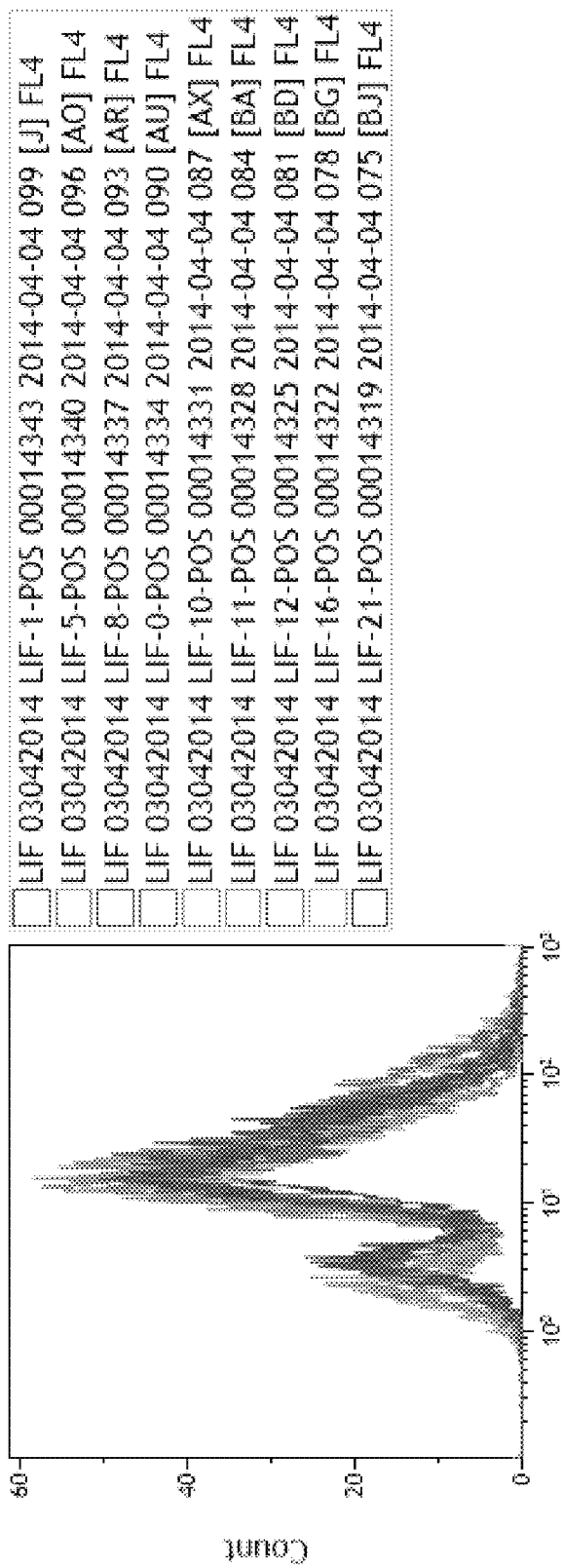
Figure 12A:
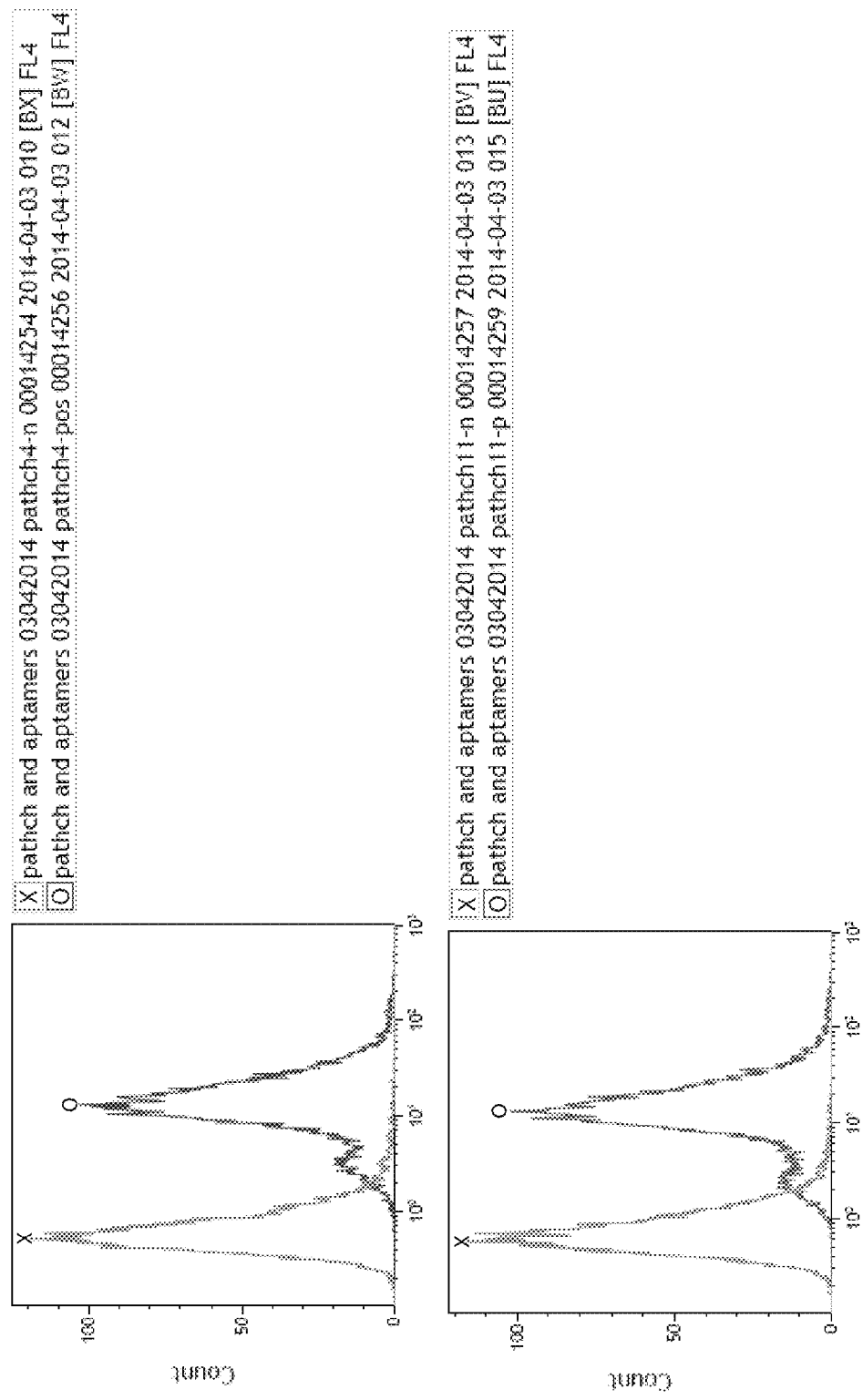
Figure 12B:
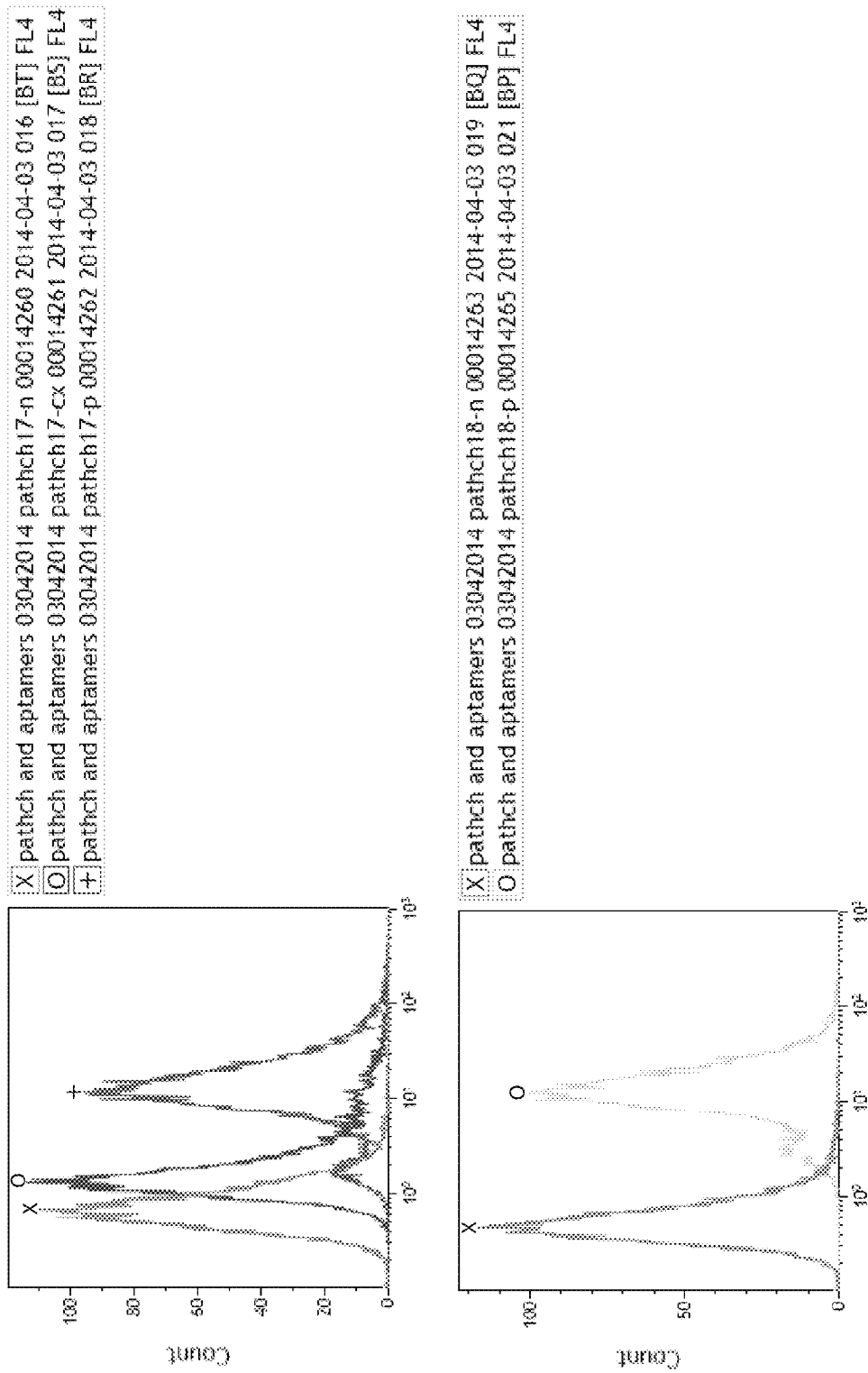
Figure 12C:
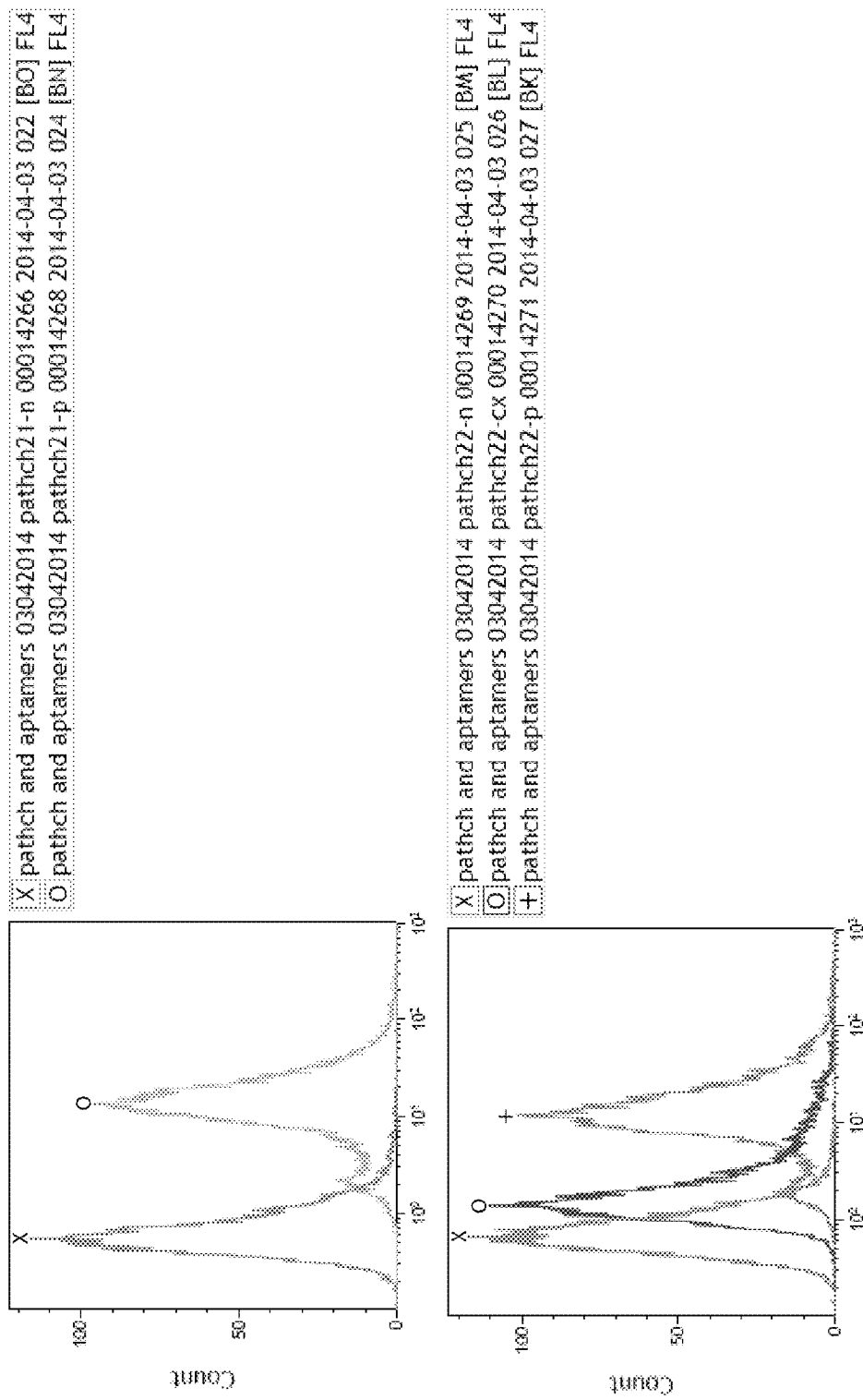
Figure 12D:
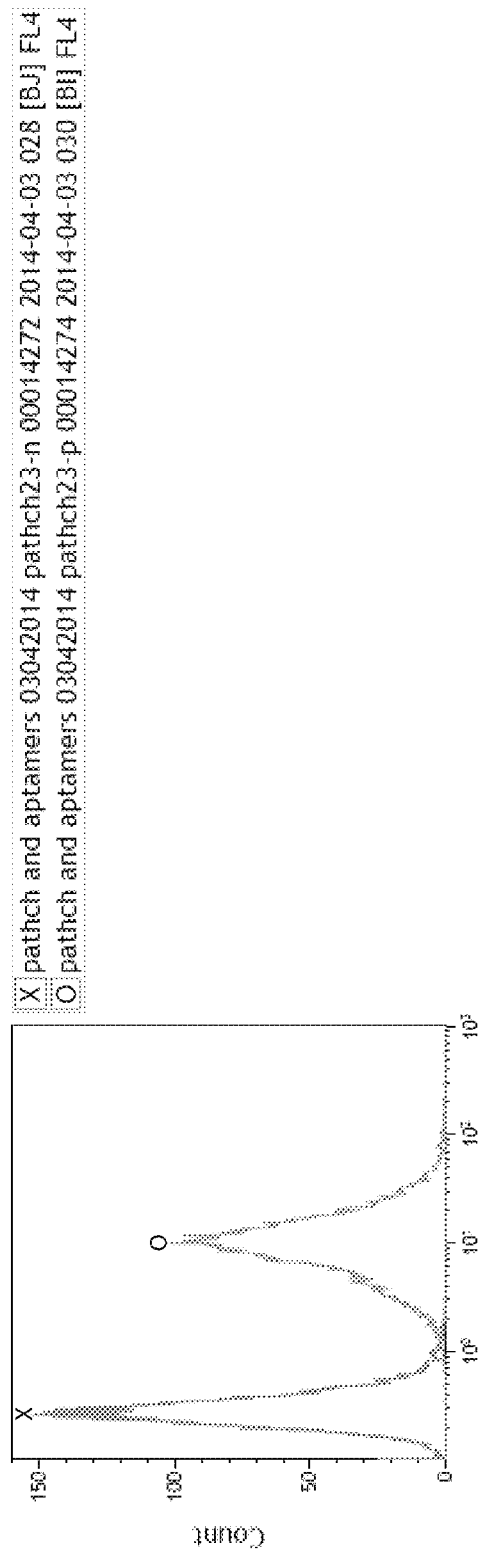
Figure 12E:
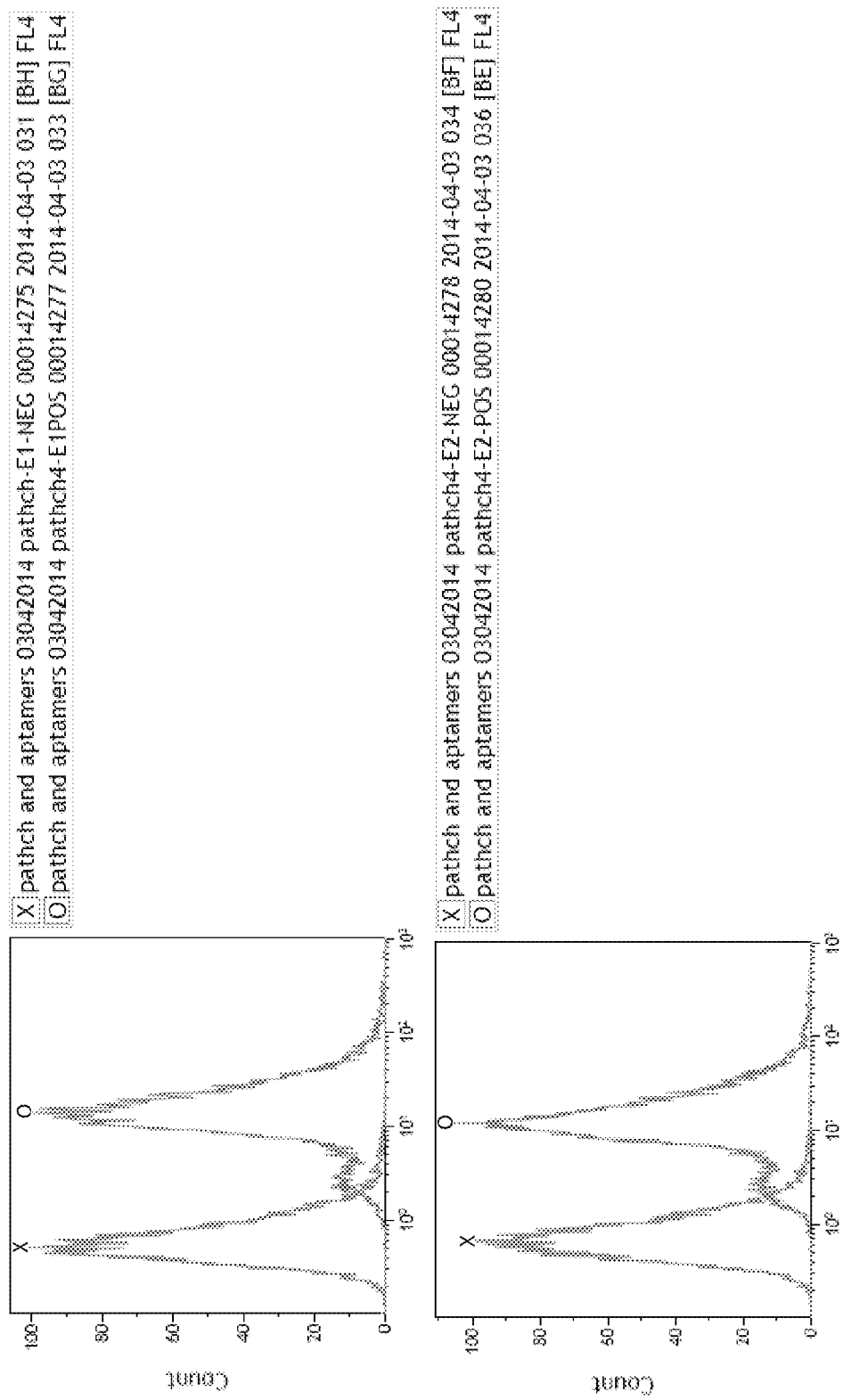
Figure 12F:
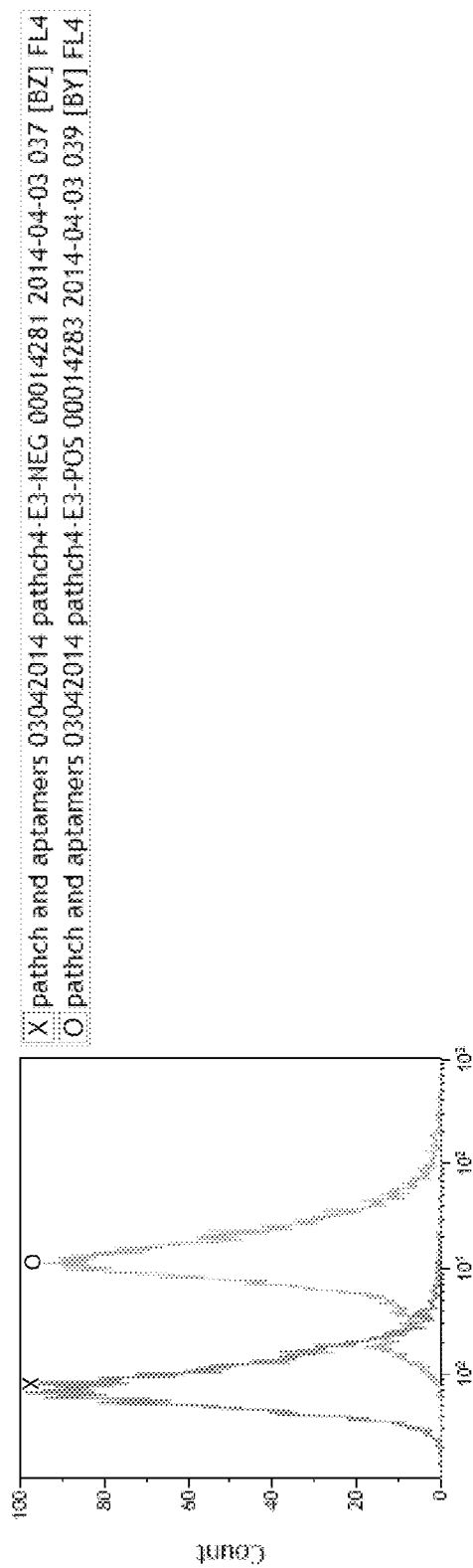
Figure 12G:
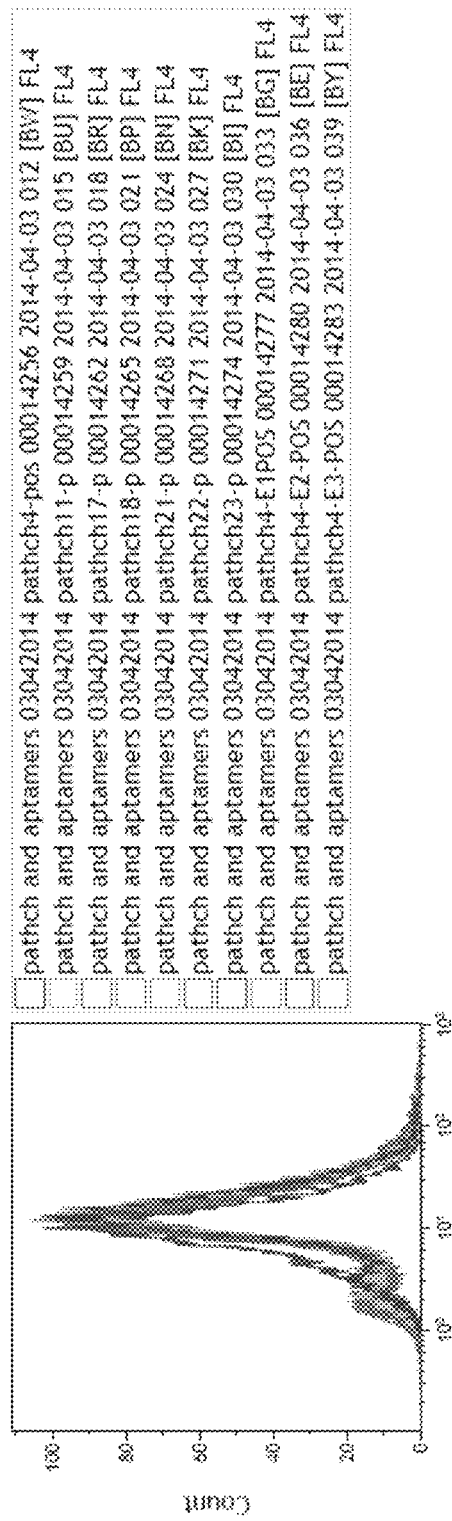
Figure 13A:
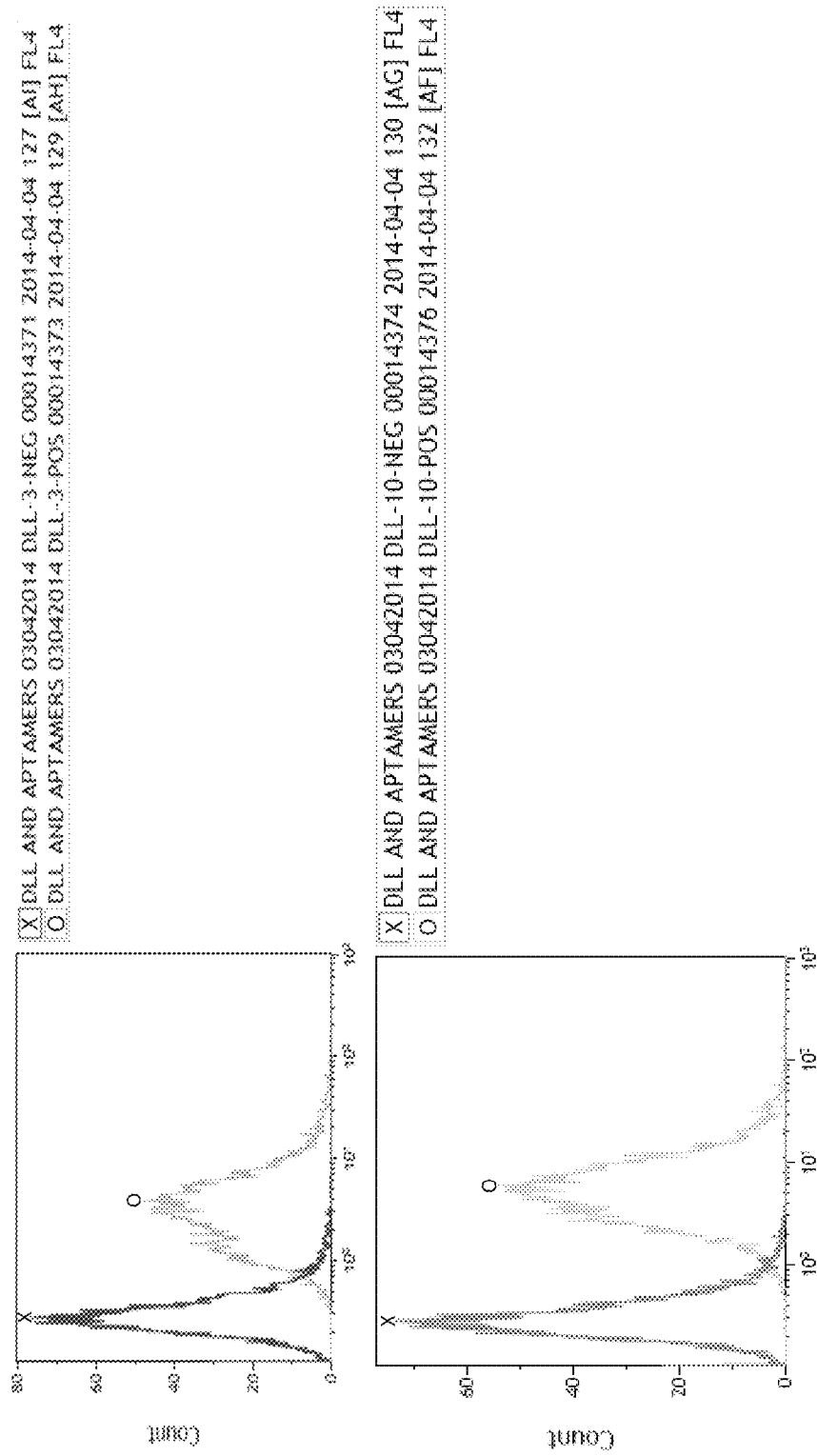
Figure 13B:
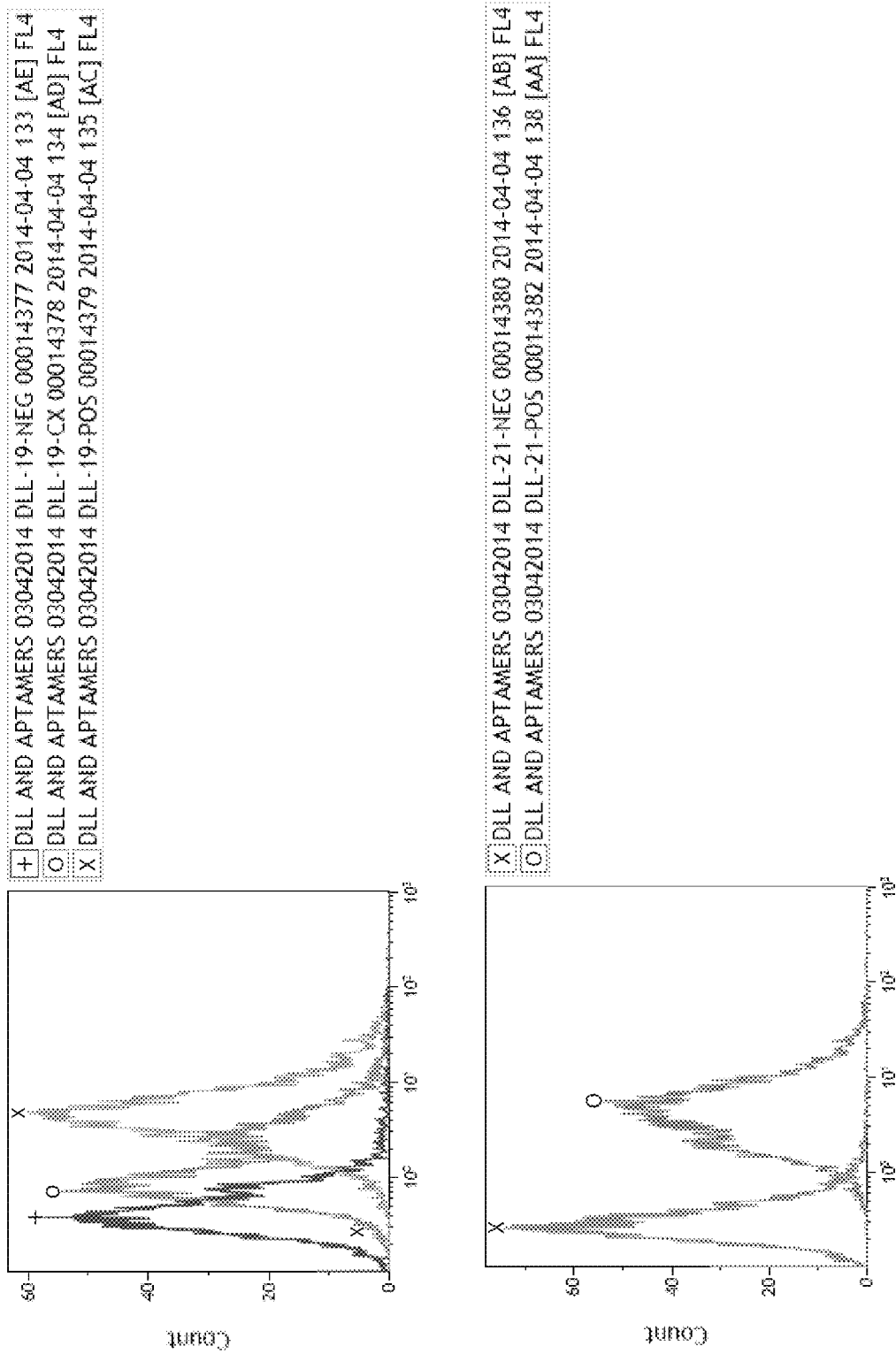
Figure 13C:
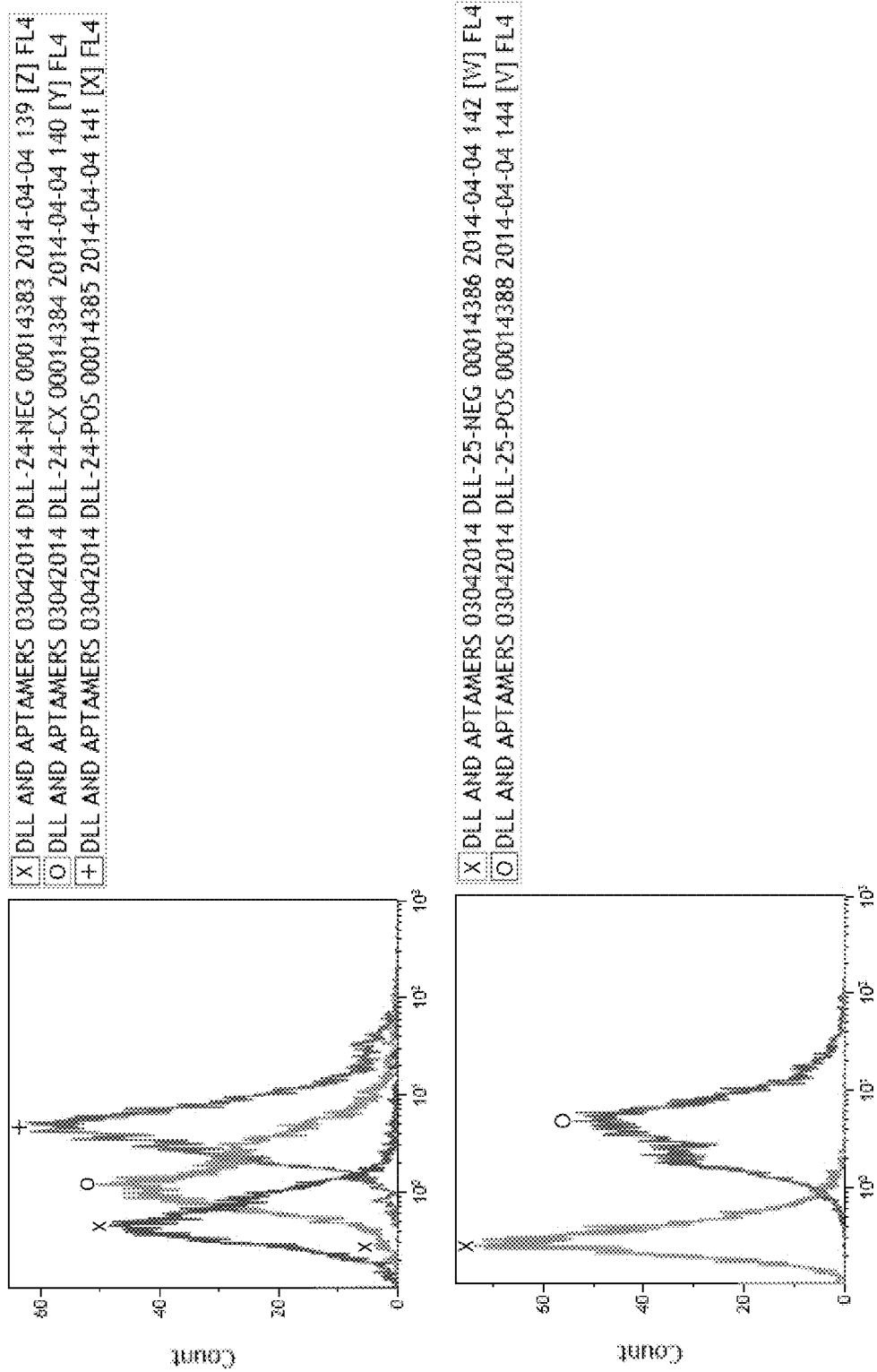
Figure 13D:
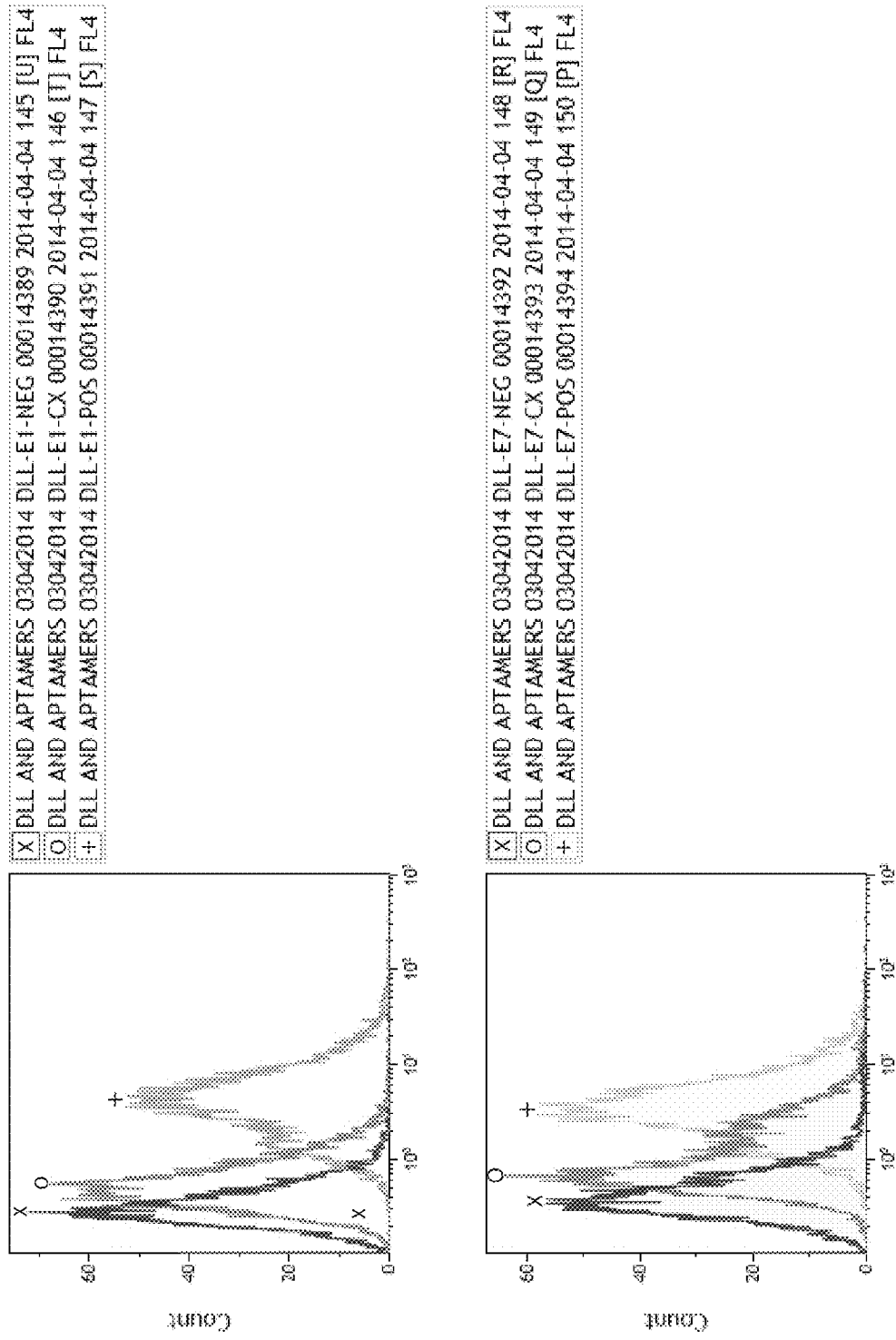
Figure 13E:
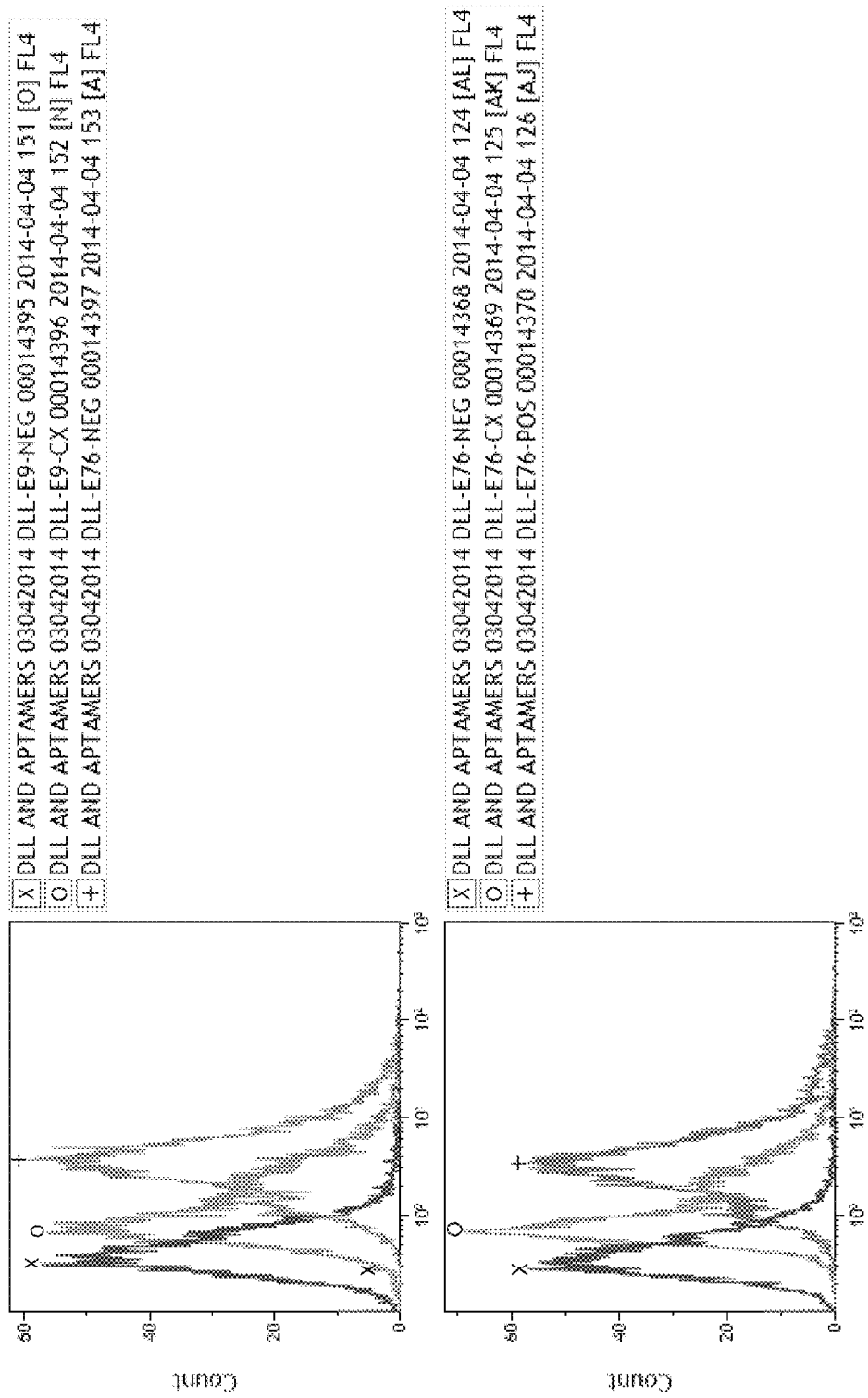
Figure 13F:
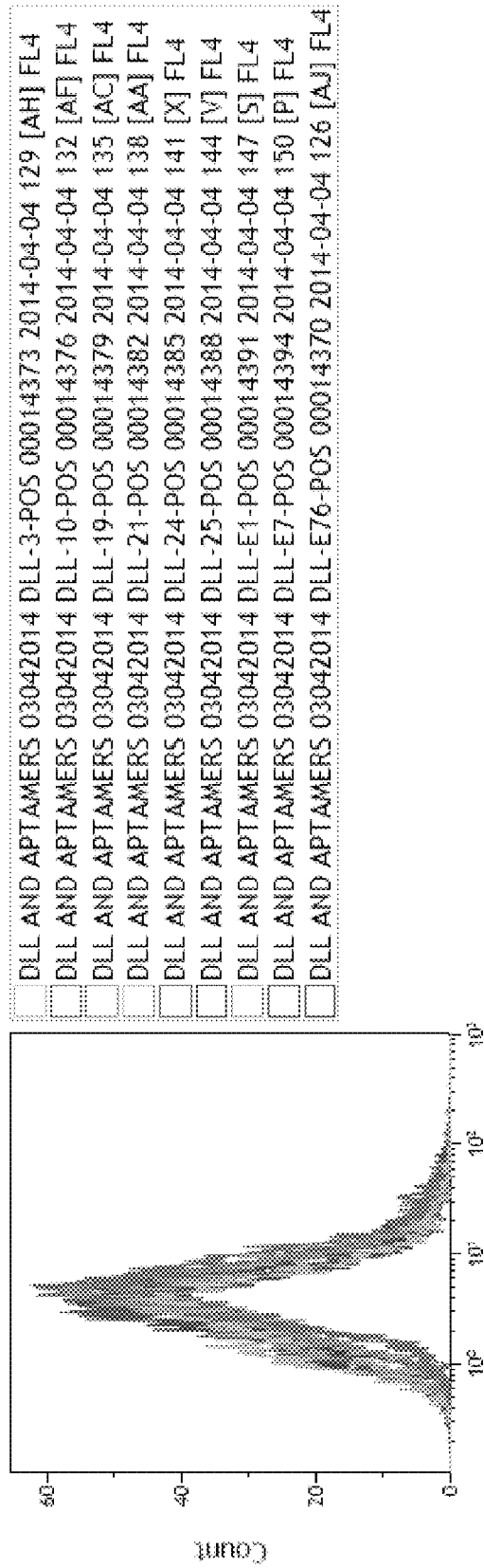
Figure 14A:
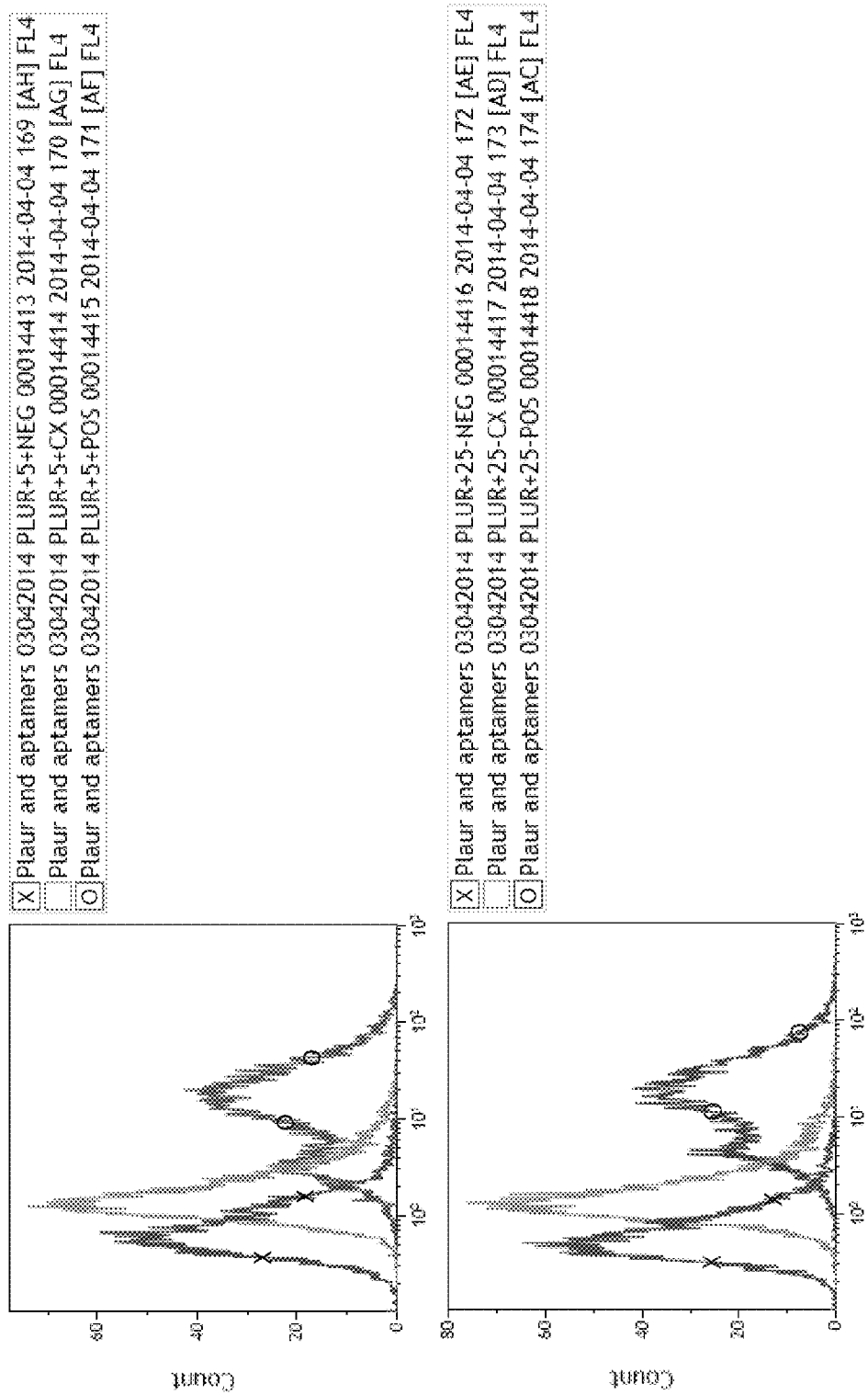
Figure 14B:
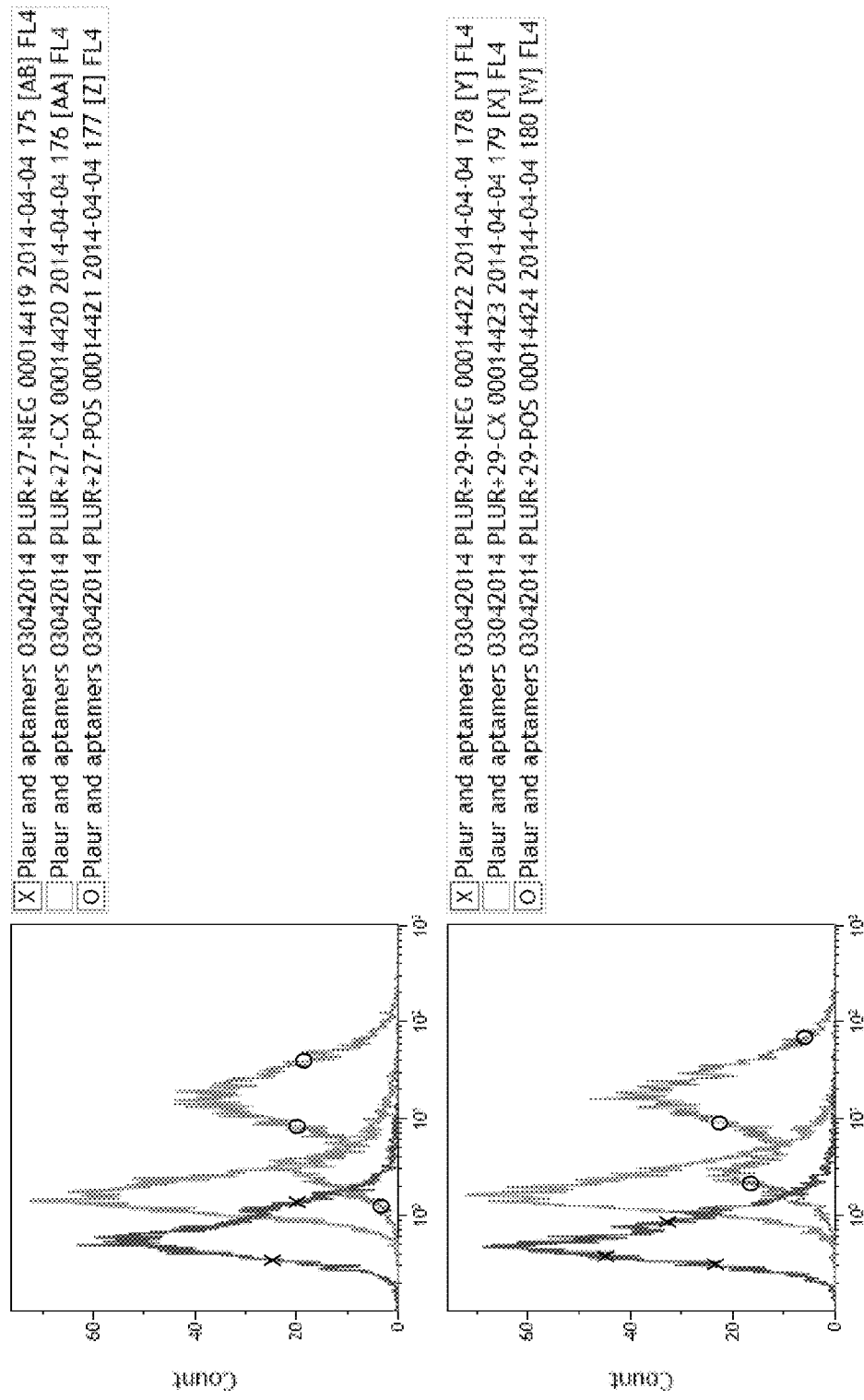
Figure 14C:
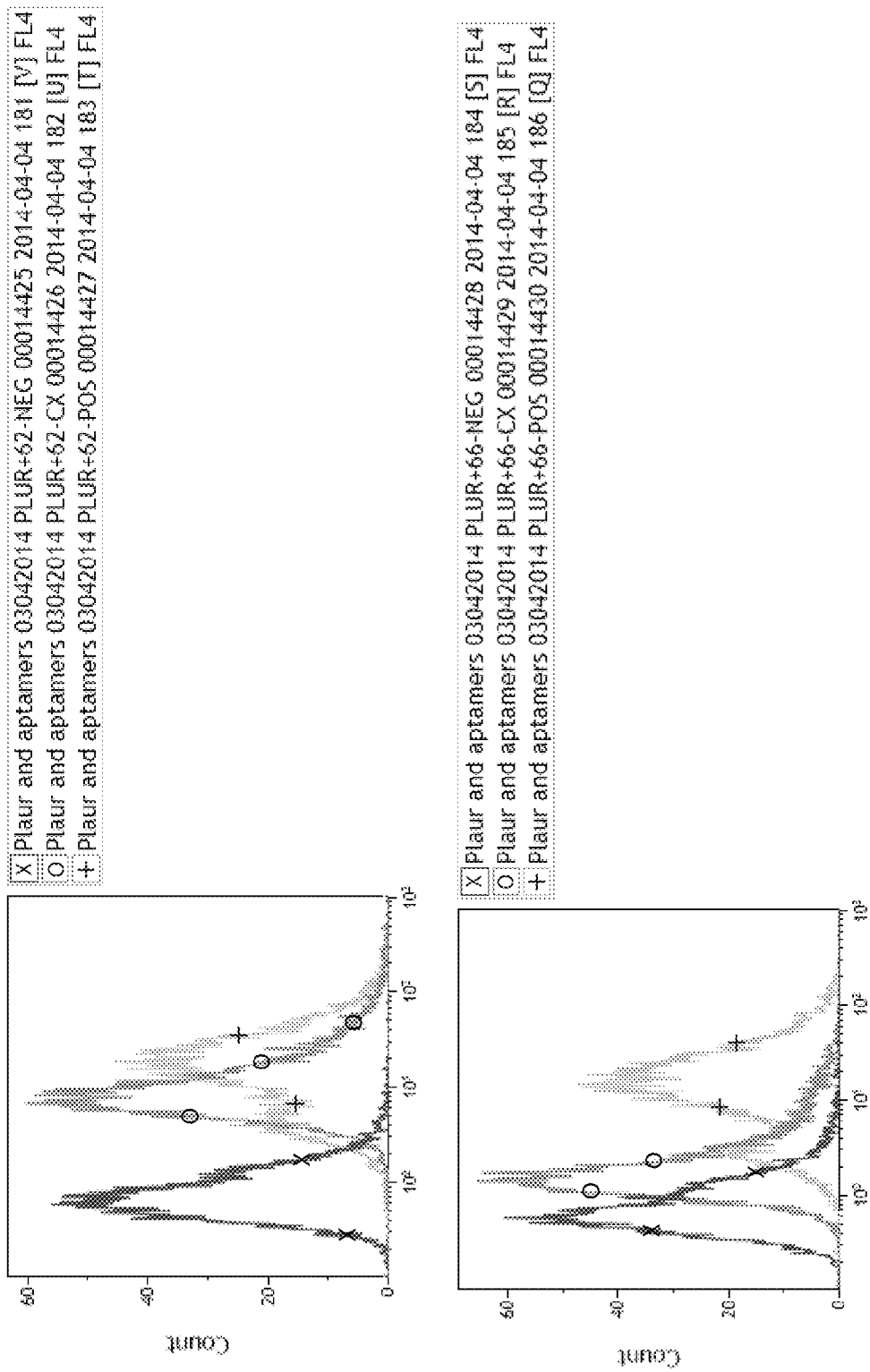
Figure 14D:
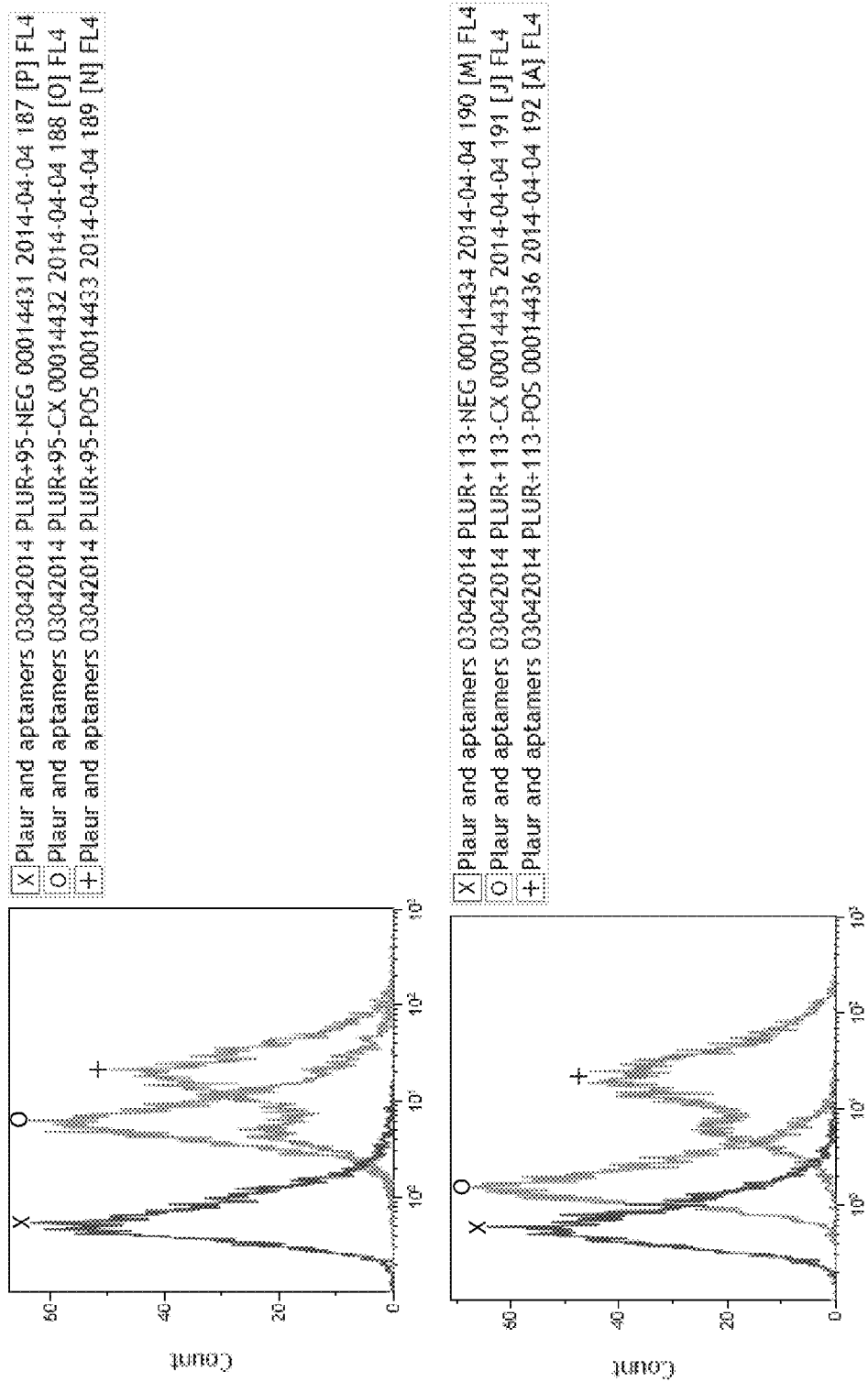
Figure 14E:
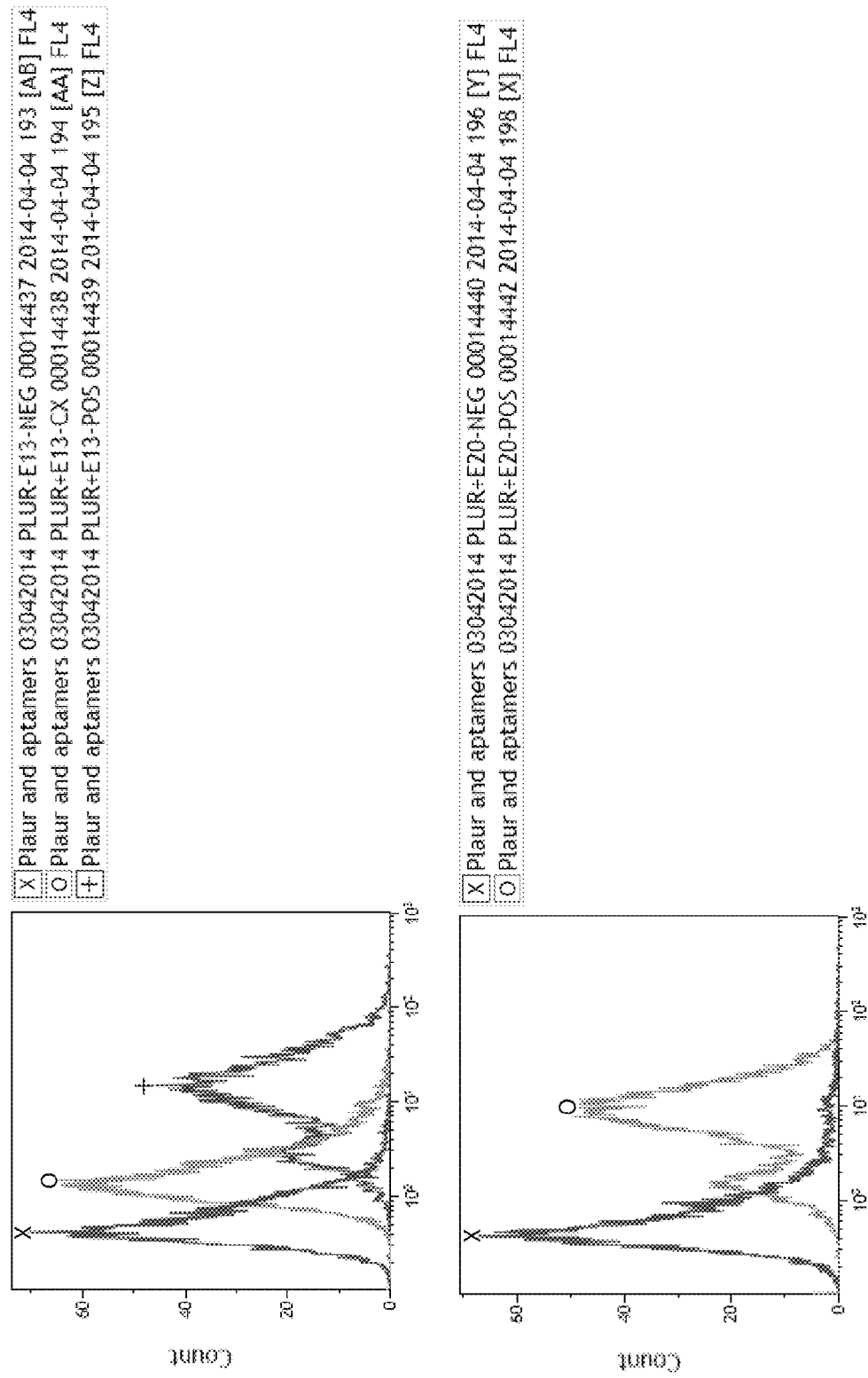
Figure 14F:
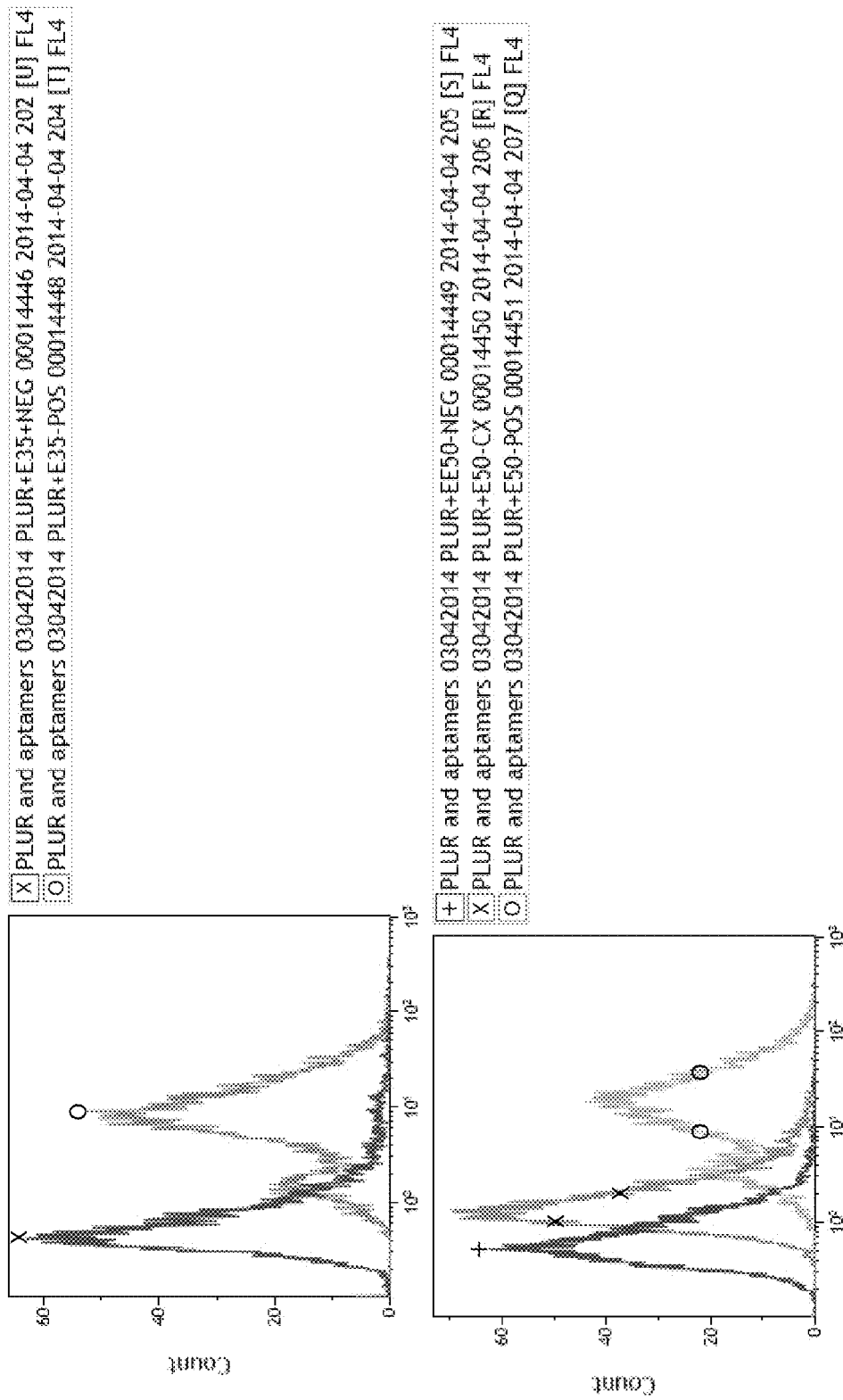
Figure 14G:
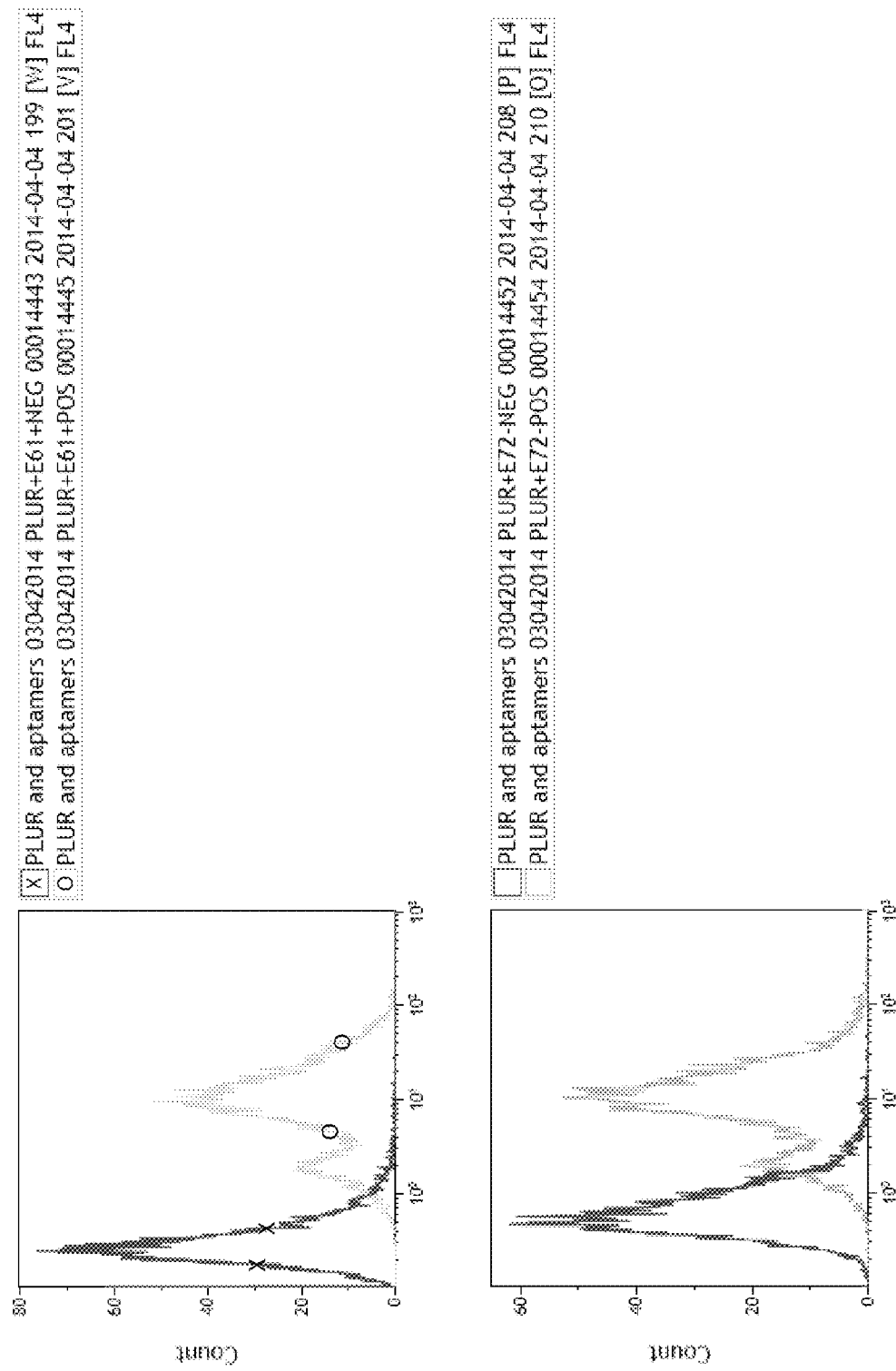
Figure 14H:
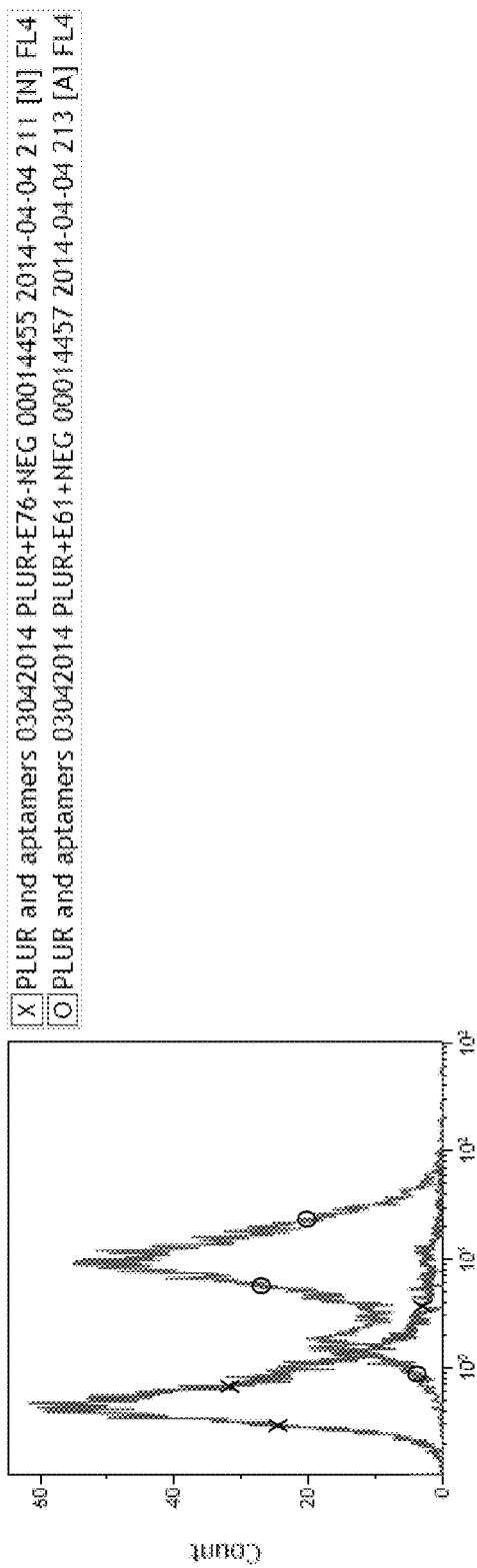
Figure 14I:
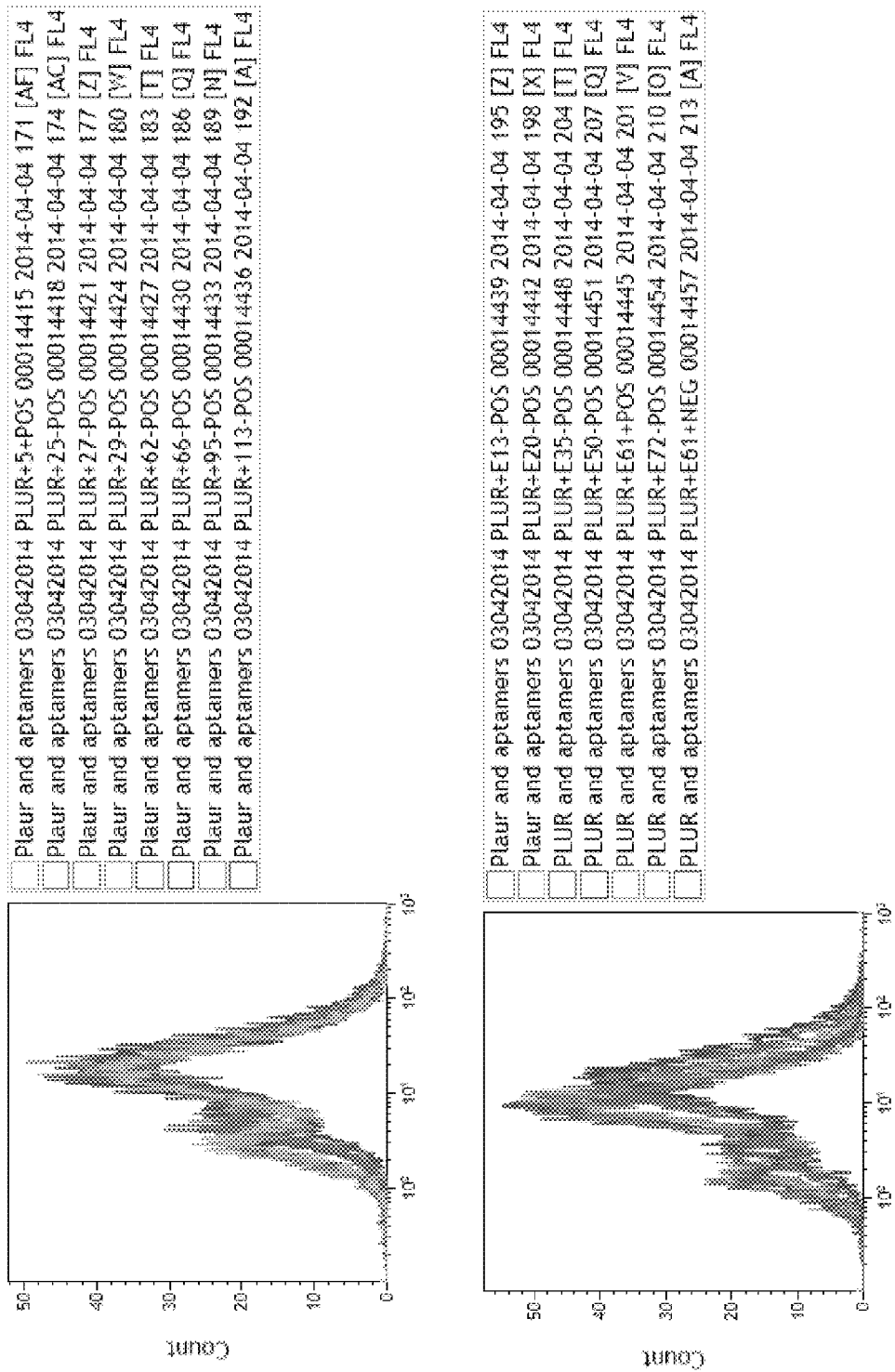
Figure 15A:
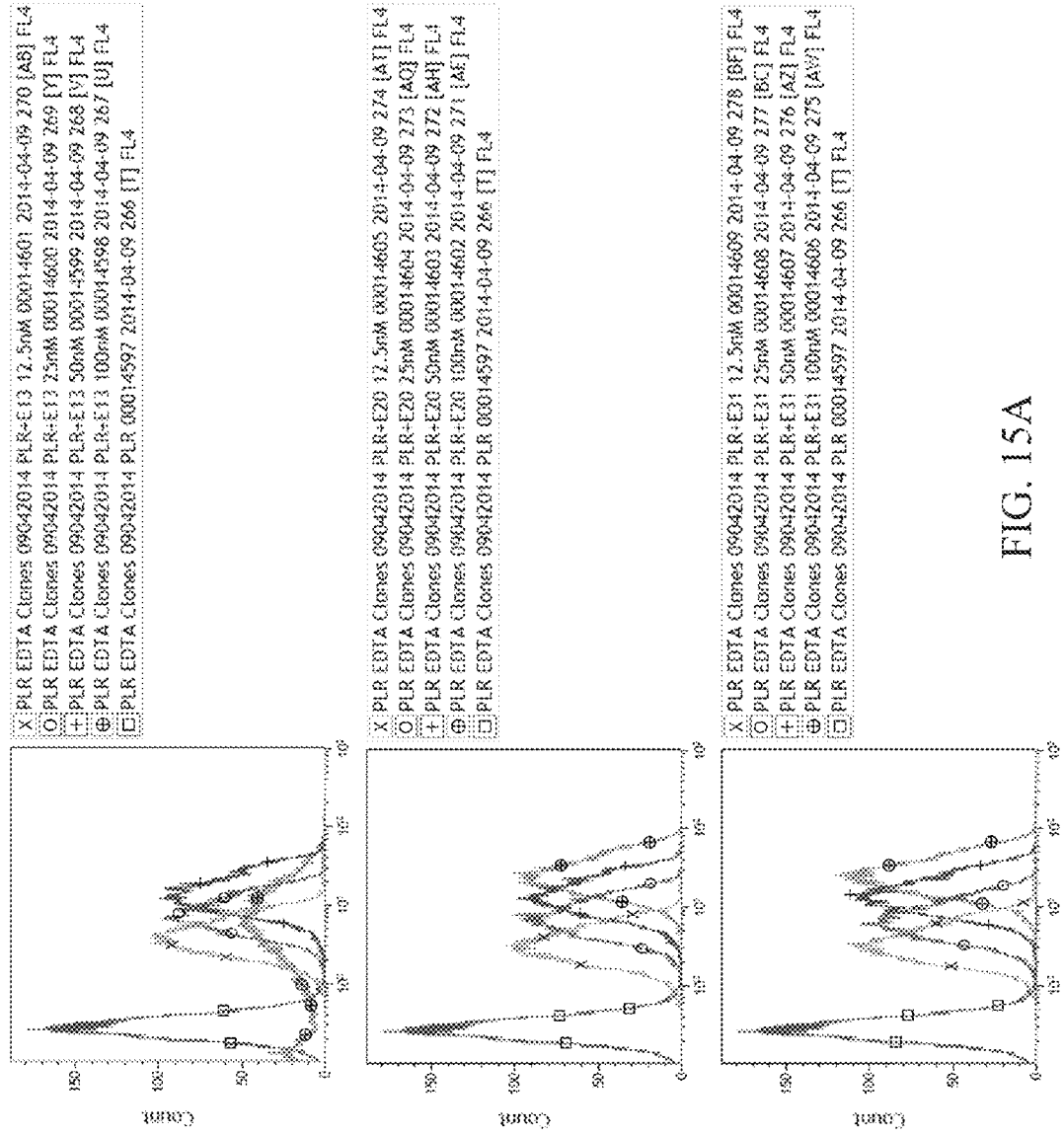
Figure 15B:
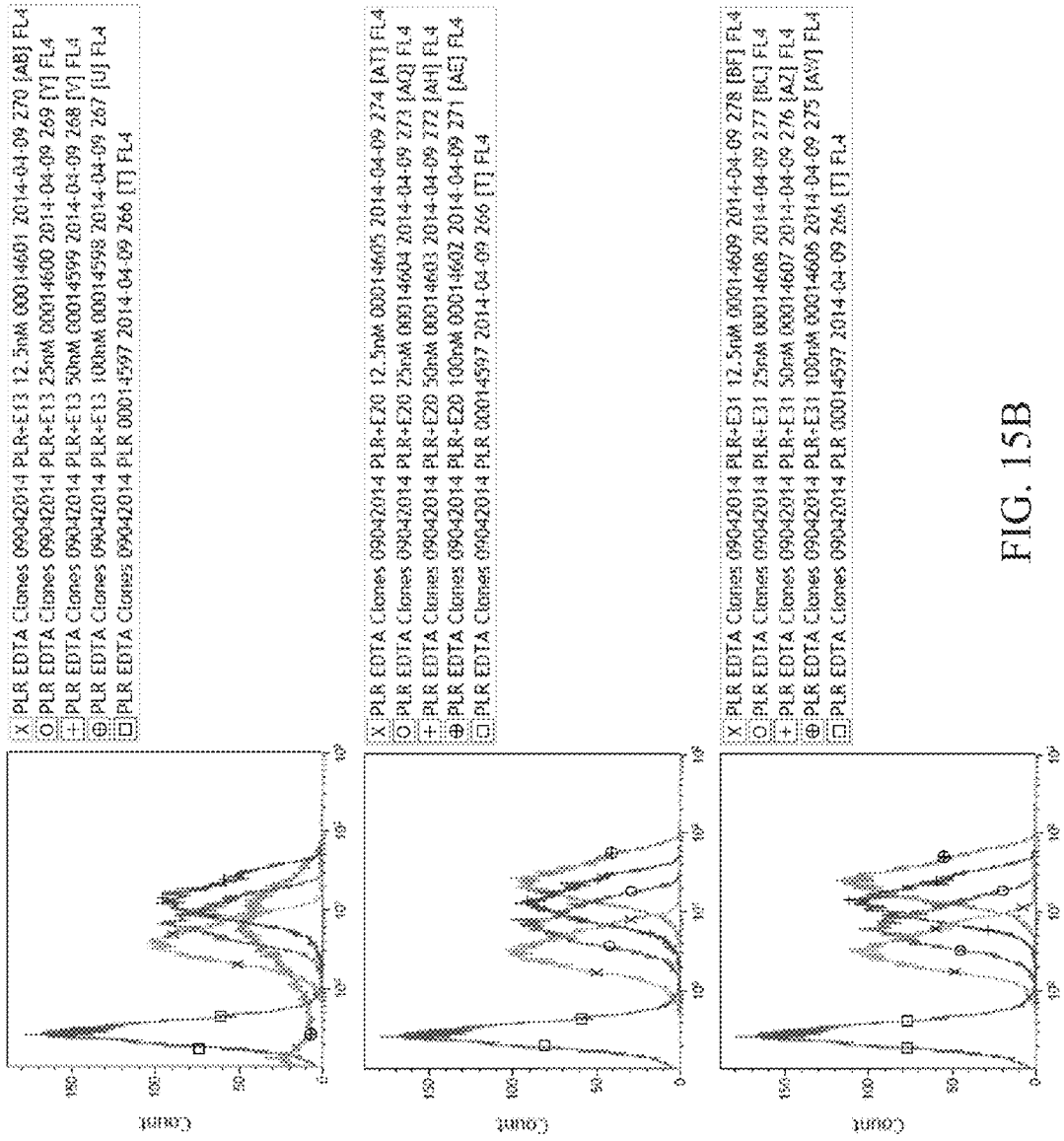
Figure 15D:
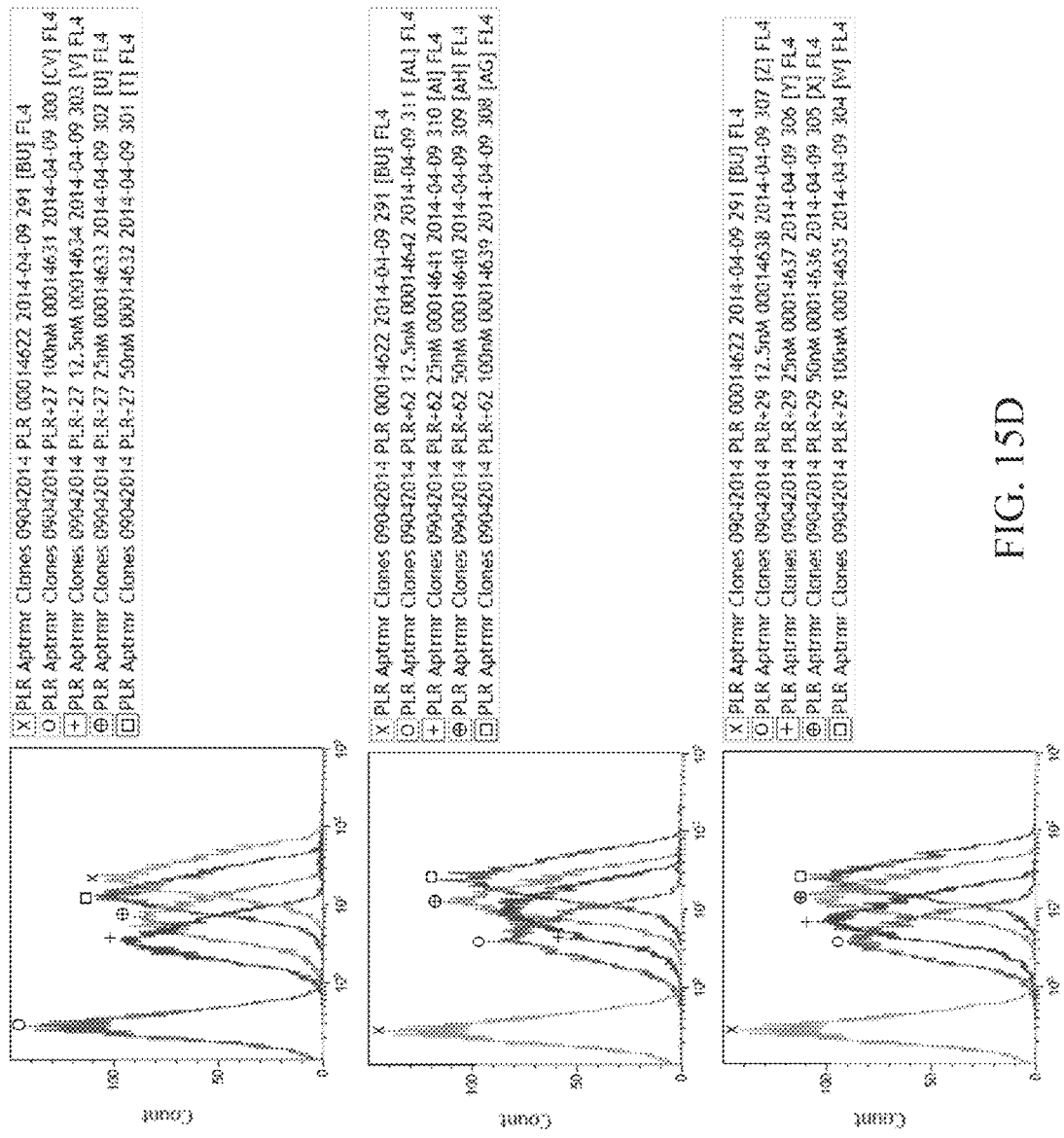
Figure 15E:
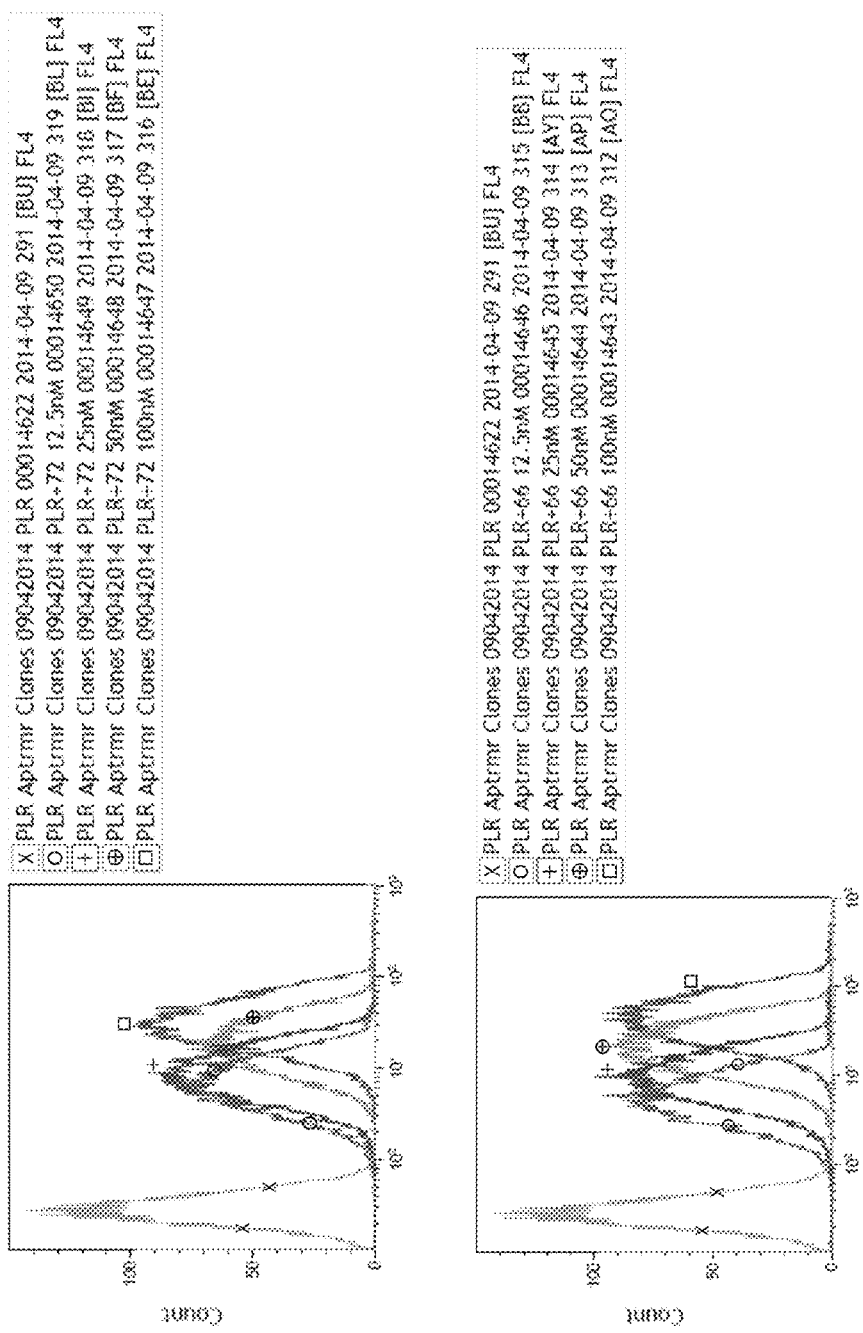
Figure 15F:
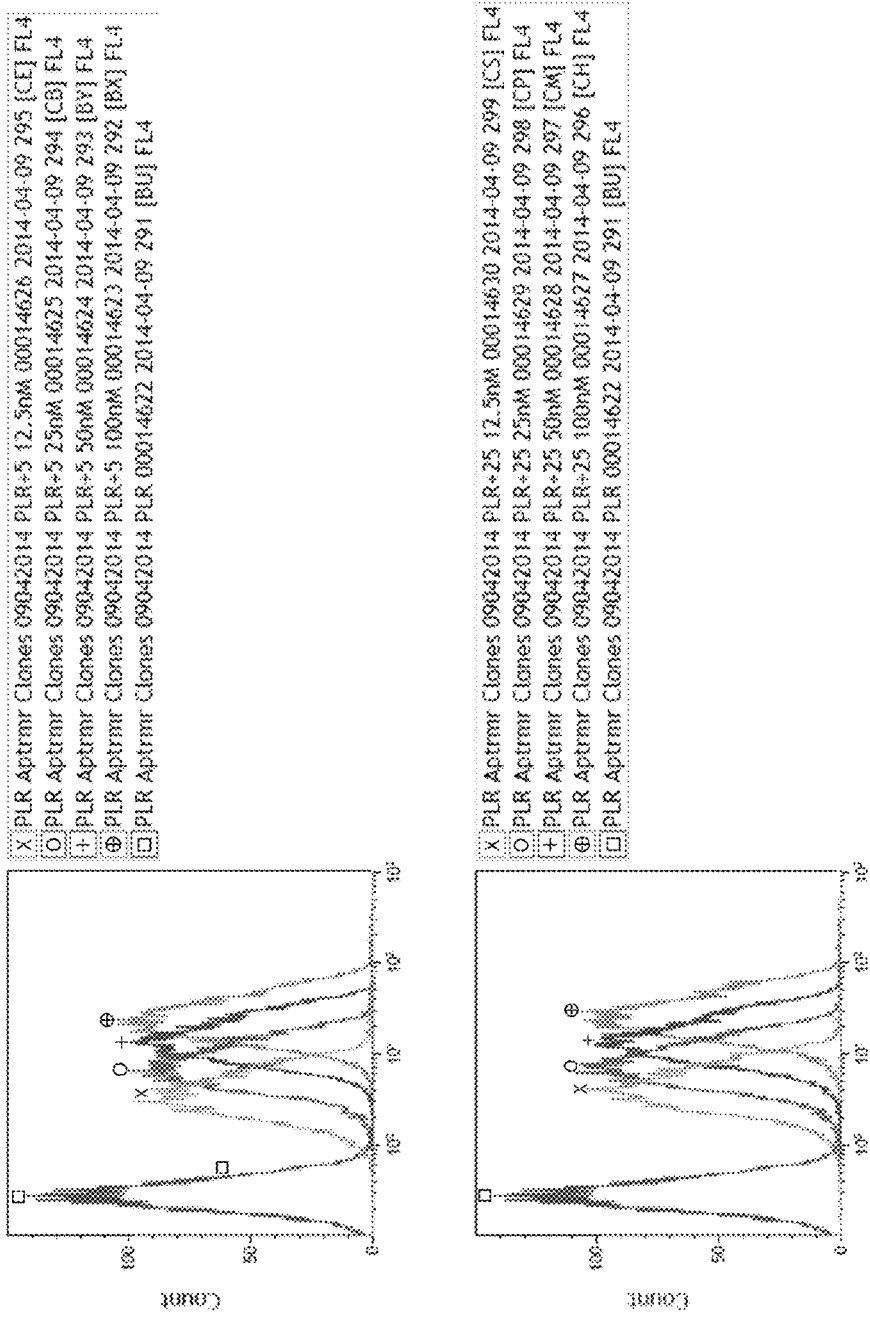
Figure 15G:
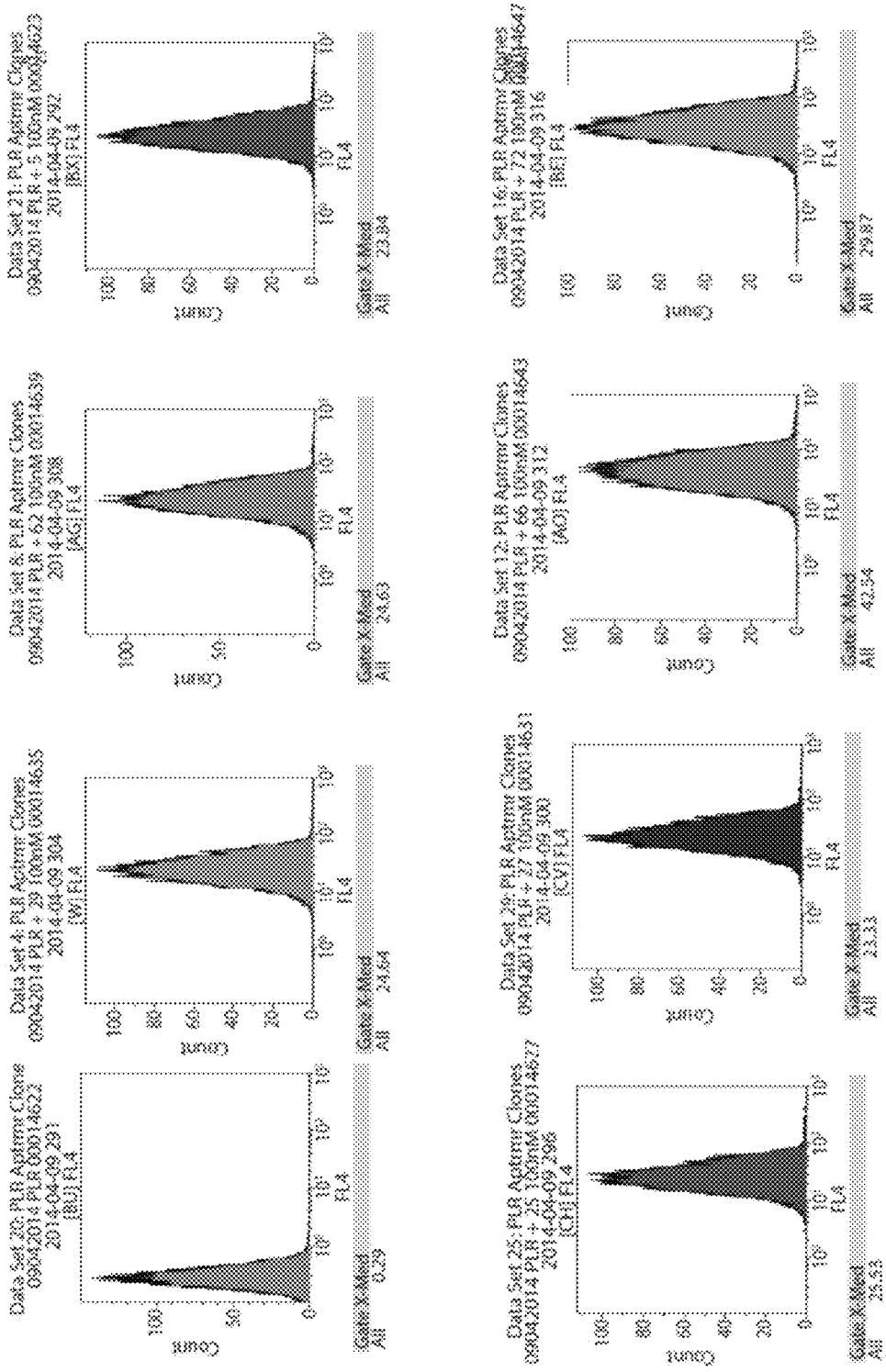
Figure 15H:
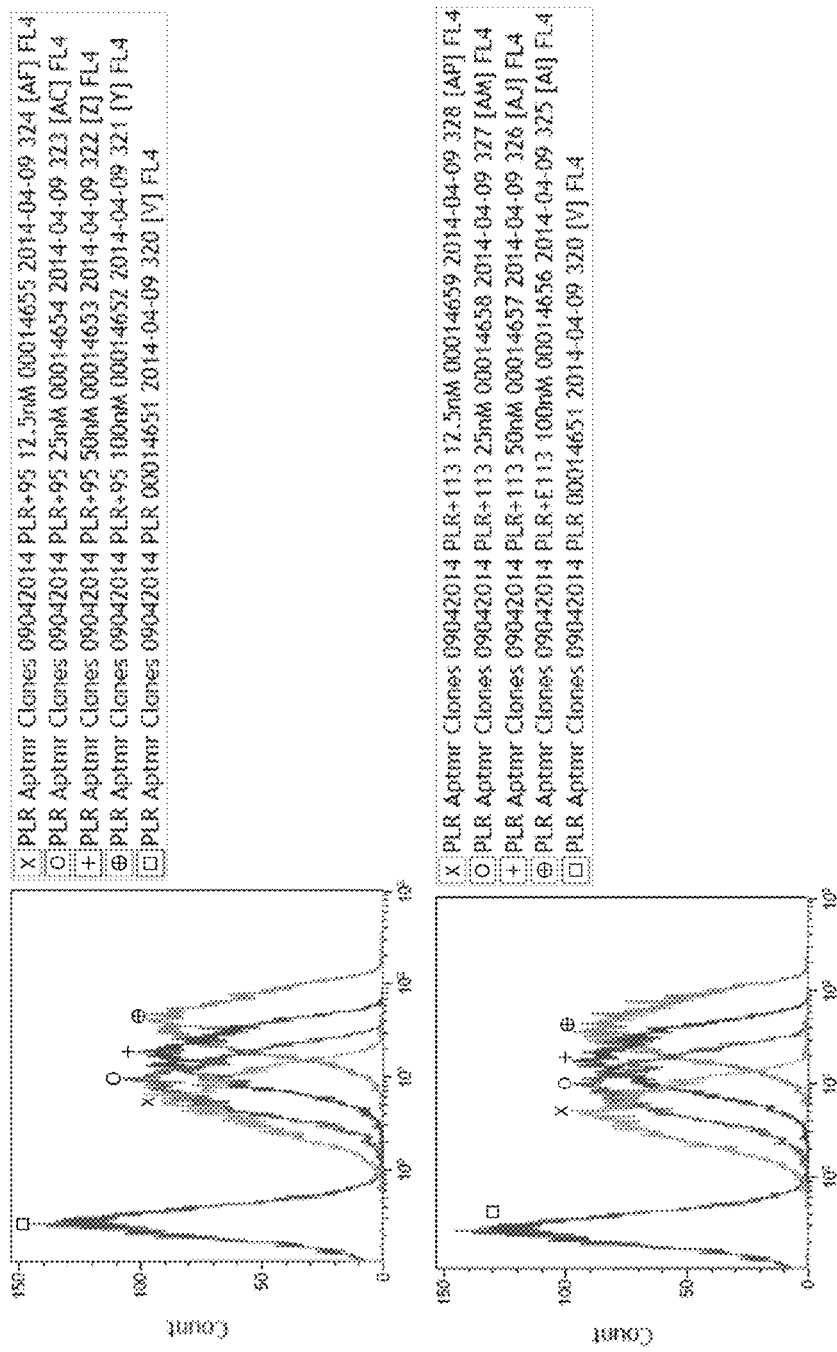
Figure 15I:
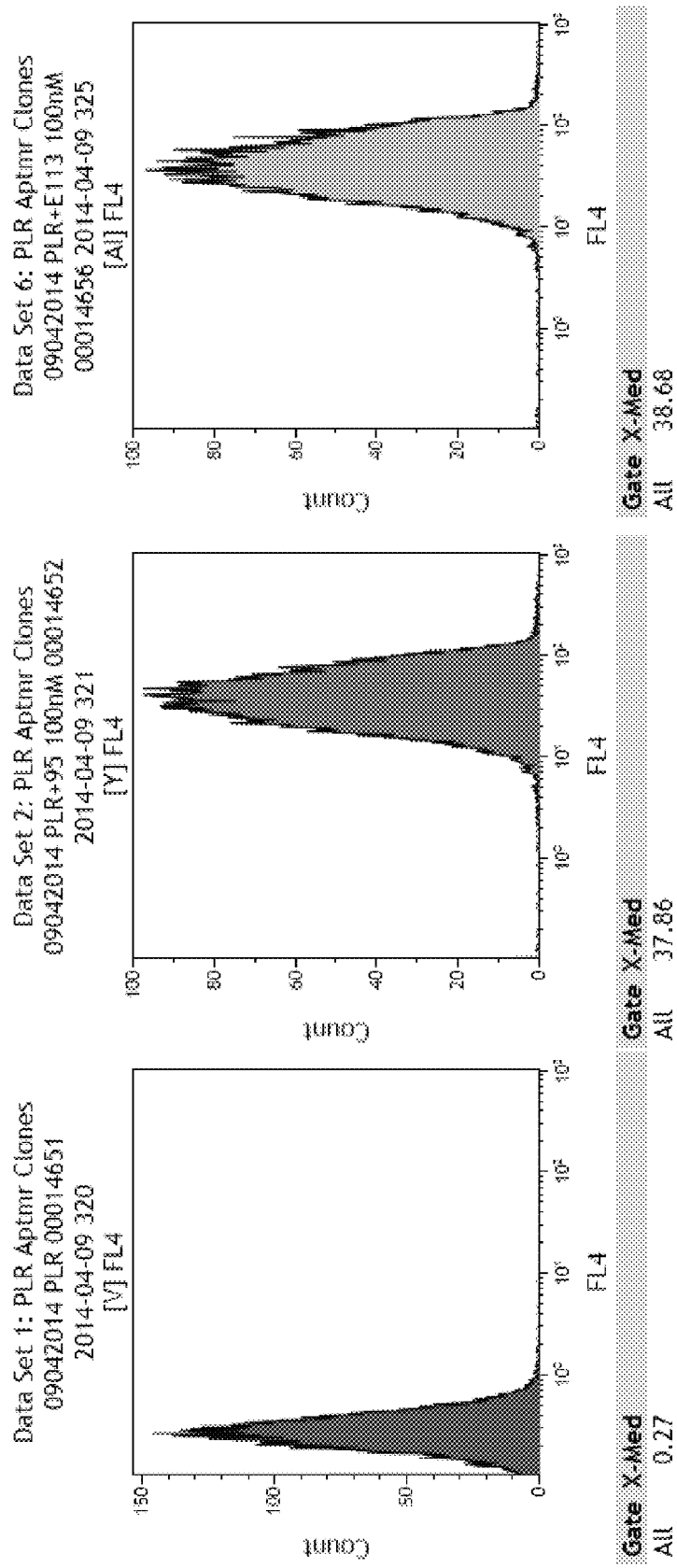

The analysis was carried out using a plaque forming assay as seen in FIG. 9 where a 33% yield was obtained from the purification scheme. Specifically, FIG. 9 shows the plaque forming assay with infection of Vero cells with VSV, after VSV has undergone SwAps-based purification. Panel 1 shows DPBS alone, panel 2 shows infection of 100 PFU from stock VSV and panel 3 shows VSV retrieved upon completion of the purification. There is no infection seen in panel 1 containing DPBS alone. Panel 2 shows $5.3 \times 10^6$ PFU mL$^{-1}$ VSV and panel 3 has $1.8 \times 10^6$ PFU mL$^{-1}$ liberated VSV. The resulting VSV recovered from the cell debris was 33.96%. 100% recovery would indicate the total activity of pure VSV before mixing it with cell debris and purification with the method described herein.

Example 10

Cloning and Sequencing of High Affinity SwAps to Neuropilin 1 (NRP) Receptor

An aptamer which showed both high affinity and switchability was selected for cloning to obtain individual aptamer sequences to the NRP receptor Pool. This pool was designed to be specific to NRP positive cells. The resulting sequences are provided in SEQ ID NOs: 21 through 30, also reproduced below at Table 4. Briefly, the pool was amplified, purified and cloned using the same method as described in Example 5 above.

TABLE 4

| NRP-SMG-20 SEQ ID NO: 21 | CTCCTCTGACTGTAACCACGGCGTGCCTCATGGTGCGTGTCC AAGTGTGCGTGTAATGACATTCGTGAAAAGTGCGCGGGCATAG GTAGTCCAGAAGCC |
| NRP-SMG-19 SEQ ID NO: 22 | CTCCTCTGACTGTAACCACGGCGCGCGTTTGCACATGTGCGTG CGACATATGCGTGGGGGGAGATGTATGAGACGTGTGGGCATA GGTAGTCCAGAAGCC |
| NRP-SMG-4 SEQ ID NO: 23 | CTCCTCTGACTGTAACCACGGCGCGTTCCTGGTAGCTCATGCG TGGCGTGGACACATGCAGGTGCGGGTTGCCTGTGTGGGCATA GGTAGTCCAGAAGCC |

TABLE 4-continued

| NRP-SMG-12 SEQ ID NO: 24 | CTCCTCTGACTGTAACCACGCGAGTCGCCTACGTACGCACACT TACCGCGCACGTCCGGGCAGGCGTGTCCCGTGCATGCGCATA GGTAGTCCAGAAGCC |
| NRP-SMG-6 SEQ ID NO: 25 | CTCCTCTGACTGTAACCACGGTGTACACTGGCACACGCACATG TCATCCGCGCGGGGCTGCACACGTCAGCCGTGTGTGGGCATA GGTAGTCCAGAAGCC |
| NRP-SMG-14 SEQ ID NO: 26 | CTCCTCTGACTGTAACCACGGCGTACGTGACCCCATACGCACT CTAGCCACATACGTTCGCCCACGCCTGTCGCTCGCGGGCATA GGTAGTCCAGAAGCC |
| NRP-SMG-1 SEQ ID NO: 27 | CTCCTCTGACTGTAACCACGGTGTGCCTGCTTGCTGATGTGTG TTGTCGGTGCGTGAGGGCGTACGTAAGTGTCGTGCGGGCATA GGTAGTCCAGAAGCC |
| NRP-SMG-E1 SEQ ID NO: 28 | CTCCTCTGACTGTAACCACGGTCTGCACTATGGTGCGTGCGTT CGGTGTACCCATGAGCGTCCATGTGTGAGTTGCTCGGGCATAG GTAGTCCAGAAGCC |
| NRP-SMG-E2 SEQ ID NO: 29 | CTCCTCTGACTGTAACCACGGTCTGCACTATGGTGCGTGCGTT CGGTGTACCCATGAGCGTCCATGTGTGAGTTGCTCGGGCATAG GTAGTCCAGAAGCC |
| NRP-SMG-E3 SEQ ID NO: 30 | CTCCTCTGACTGTAACCACGCTACATGTGAGGGCGCTTGCATG CAATATGCAGACTCTGACGCGTGTGTTGGTTGTGTGGGCATAG GTAGTCCAGAAGCC |

Flow cytometry data indicated the aptamers that demonstrated the best switching capability. These are NRP-SMG-E1; NRP-SMG-E2 and NRP-SMG-E3. This data is reproduced at FIGS. 10A-F

Example 11

Cloning and Sequencing of High Affinity SwAps to Leukemia Inhibitory Factor (LIF) Receptor An aptamer pool selected specifically to LIF positive cells and which showed both high affinity and switchability was selected for cloning to obtain individual aptamer sequences to the NRP receptor. The resulting sequences are provided in SEQ ID NOs: 31 through 47, also reproduced below at Table 5. Briefly, the pool was amplified, purified and cloned using the same method as described in Example 5 above.

TABLE 5

| LIF-SMG-1 SEQ ID NO: 31 | CTCCTCTGACTGTAACCACGGTAGCTATGGCCACGTGCACATT CAGTATGCACGTTAATGCTCGCATGTCGTACGCGTGGGCATAG GTAGTCCAGAAGCC |
| LIF-SMG-12 SEQ ID NO: 32 | CTCCTCTGACTGTAACCACGCCACCCGTCTTTGTGCATGCTTG TACTGCATACATCTCGCCACACGCGTACAGCACACGTGCATAG GTAGTCCAGAAGCC |
| LIF-SMG-5 SEQ ID NO: 33 | CTCCTCTGACTGTAACCACGGGCATAGGCGGGTGTGTATCTGC CAAGCGCGTGCTTGCTGATTCTCGCGCGAATCACAGGCGCATA GGTAGTCCAGAAGCC |

TABLE 5 -continued

| | |
|---|---|
| LIF-SMG-8 SEQ ID NO: 34 | CTCCTCTGACTGTAACCACGGTGCAGGTGAGAGCATGTGCGTG TCATGGTCGAACCGTGGCGCTTGCATTGGGTGTGCGTGCATAG GTAGTCCAGAAGCC |
| LIF-SMG-9 SEQ ID NO: 35 | CTCCTCTGACTGTAACCACGGCGTACATCCCCACACGTGCGTA TTACGTGCTCCCCCGTGCGTGTCGGTGGAGCGTGTGTGCATAG GTAGTCCAGAAGCC |
| LIF-SMG-10 SEQ ID NO: 36 | CTCCTCTGACTGTAACCACGCTGCATCCTAGGGTCTATGCCTA GGGGGCTGCTATGCGTGCACGCGTGTCGGTCATGTGGGCATAG GTAGTCCAGAAGCC |
| LIF-SMG-21 SEQ ID NO: 37 | CTCCTCTGACTGTAACCACGGCATGTTTCCCCGCGTGTGCATT TGACGTGTGTGTCCCCACGCACGTATCACGCAAGGGGGCATAG GTAGTCCAGAAGCC |
| LIF-SMG-11 SEQ ID NO: 38 | CTCCTCTGACTGTAACCACGGCGTGCACCTCCGCGTATGGCTT GCATATGAGTGCTGTTCTCCGTATTTCGGACATACGGGCATAG GTAGTCCAGAAGCC |
| LIF-SMG-16 SEQ ID NO: 39 | CTCCTCTGACTGTAACCACGGCACATATCTTGCTGCCCACGTG CCACCACCGTGTCTCCCTGCCCATCCGAAGTGCGCGCGCATAG GTAGTCCAGAAGCC |
| LIF-SMG-E46 SEQ ID NO: 40 | CTCCTCTGACTGTAACCACGGCACCTGAGTCTGTCCGTCCGCT TGACACGCACGCAAGGGTATGCGCATCCCACACGCGCGCATAG GTAGTCCAGAAGCC |
| LIF-SMG-E8 SEQ ID NO: 41 | CTCCTCTGACTGTAACCACGGCGCGTATCCCCGAGTGCGTACG CGGTGTTTGCTCGATCGTACGTGCATGGTGTGCGTGTGCATAG GTAGTCCAGAAGCC |
| LIF-SMG-E16 SEQ ID NO: 42 | CTCCTCTGACTGTAACCACGGCGTGTGTCCCGGTGTGCGCATA GTCCAAGTACGTCGCCGTGTGTACGTTCAATGCGTGGGCATAG GTAGTCCAGAAGC CTCCTCTGACTGTAACCACGGTGCGTATGGACACGTCTGTACT GAGTGCGCATGTTGAGACGCATGCGTCGTGCGTGTGTGCATAG GTAGTCCAGAAGCC |
| LIF-SMG-E6 SEQ ID NO: 43 | CTCCTCTGACTGTAACCACGGTGCGTATGGACACGTCTGTACT GAGTGCGCATGTTGAGACGCATGCGTCGTGCGTGTGTGCATAG GTAGTCCAGAAGCC |
| LIF-SMG-E45 SEQ ID NO: 44 | CTCCTCTGACTGTAACCACGGTGCATGTGTCGGTATGCGGGCC GCTTGTGCGTGTGACGACTCGTGTGTGTAATGCGCGCGCATAG GTAGTCCAGAAGCC |
| LIF-SMG-E13 SEQ ID NO: 45 | TCCTCTGACTGTAACCACGCCATGCACCCGTGTGTGTGGTG TACGTGTGTGTCCACGGGAACGTATCACGTCATAGGGCATAGG TAGTCCAGAAGCC |
| LIF-SMG-E7 SEQ ID NO: 46 | CTCCTCTGACTGTAACCACGGCGCGTGCGTAGGCATAGGTGTC GTGTACGCGTGTCTCAGCGCAATTGCGTCGGGTGTGTGCATAG GTAGTCCAGAAGCC |
| LIF-SMG-E55 SEQ ID NO: 47 | CTCCTCTGACTGTAACCACGGCATGCGGTCTCGCACTCGGTTC TAGTGTCCACGCTTGTGTATGCGTGCGCGGTGTGTGTGCATAG GTAGTCCAGAAGCC |

Flow cytometry data showed that the aptamers with the best switching capability are LIF-SMG-E46, E8, E16, E6, E45, E13, E7 and E55. This data is reproduced at FIGS. 11A-J.\

Example 12

Cloning and Sequencing of High Affinity SwAps to Patched 1 (PTCH1) Receptor An aptamer pool selected specifically to PTCH1 positive cells and which showed both high affinity and switchability was selected for cloning to obtain individual aptamer sequences to the NRP receptor. The resulting sequences are provided in SEQ ID NOs: 48 through 59, also reproduced below at Table 6. Briefly, the pool was amplified, purified and cloned using the same method as described in Example 5 above.

TABLE 6

| | |
|---|---|
| PTCH1-SMG-17 SEQ ID NO: 48 | CTCCTCTGACTGTAACCACGCCGCGAGTTGCCACACATGCACT TCTCACACATACCCGTGTACACGTACAGCACATATGCGCATAG GTAGTCCAGAAGCC |
| PTCH1-SMG-22 SEQ ID NO: 49 | CTCCTCTGACTGTAACCACGCCGCGAGTTGCCACACATGCACT TCTCACACATACCCGTGTACACGTACAGCACATATGCGCATAG GTAGTCCAGAAGCC |
| PTCH1-SMG-16 SEQ ID NO: 50 | CTCCTCTGACTGTAACCACGCCCAATCCCGCACCACGTGCATG CCACGCCCACGCATGAGTACACACGTACGGCGCATGTGCATAG GTAGTCCAGAAGCC |
| PTCH1-SMG-21 SEQ ID NO: 51 | CTCCTCTGACTGTAACCACGCCCAATCCCGCACCACGTGCATG CCACGCCCACGCATGAGTACACACGTACGGCGCATGTGCATAG GTAGTCCAGAAGCC |
| PTCH1-SMG-4 SEQ ID NO: 52 | CTCCTCTGACTGTAACCACGGTGCCTGCAGGGACGCGTGTAAC CGGAATGTACGCCGCGACGCACACGCCTAGTGTACGTGCATAG GTAGTCCAGAAGCC |
| PTCH1-SMG-11 SEQ ID NO: 53 | CTCCTCTGACTGTAACCACGGTGCCTGCAGGGACGCGTGTAAC CGGAATGTACGCCGCGACGCACACGCCTAGTGTACGTGCATAG GTAGTCCAGAAGCC |
| PTCH1-SMG-18 SEQ ID NO: 54 | CTCCTCTGACTGTAACCACGGTACGGTCGTCACTGTGCGTACG CTGTGCAAAGATGCAAGTGCGCATACTGGGTGTCGGTGCATAG GTAGTCCAGAAGCC |
| PTCH1-SMG-23 SEQ ID NO: 55 | CTCCTCTGACTGTAACCACGGTACGGTCGTCACTGTGCGTACG CTGTGCAAAGATGCAAGTGCGCATACTGGGTGTCGGTGCATAG GTAGTCCAGAAGCC |
| PTCH1-SMG-24 SEQ ID NO: 56 | CTCCTCTGACTGTAACCACGGGACACGCCGGGACGTGCATACC GGATGCGCACGTAATCACCTGTGGGTGGGACGAGCCGGCATAG GTAGTCCAGAAGCC |
| PTCH1-SMG-E1 SEQ ID NO: 57 | CTCCTCTGACTGTAACCACGACGCGCGATGCGGCAAGCATGTT ACGCCCATGTATCTTCGTGCACATGCCCTCCGTGTGTGCATAG GTAGTCCAGAAGCC |

TABLE 6-continued

| | |
|---|---|
| PTCH1-SMG-E2 SEQ ID NO: 58 | CTCCTCTGACTGTAACCACGACACTGTCCTCCTCTGACTGTAA CCACGGCATAGGTAGTCCAGAAGCC |
| PTCH1-SMG-E3 SEQ ID NO: 59 | CTCCTCTGACTGTAACCACGACGCGCGATGCGGCAAGCATGTT ACGCCCATGTATCTTCGTGCACATGCCCTCCGTGTGTGCATAG GTAGTCCAGAAGCC |

Flow cytometry data shows that aptamers PTCH1-SMG-E1, E2 and E3 have the best switching capability. This data is reproduced at FIGS. 12A-G Example 13

Cloning and Sequencing of High Affinity SwAps to Delta-Like Ligand 4 (DLL4) Receptor An aptamer pool selected specifically to DLL4 positive cells and which showed both high affinity and switchability was selected for cloning to obtain individual aptamer sequences to the NRP receptor. The resulting sequences are provided in SEQ ID NOs 60 through 74, also reproduced below at Table 7. Briefly, the pool was amplified, purified and cloned using the same method as described in Example 5 above.

TABLE 7

| | |
|---|---|
| DLL4-SMG-10 SEQ ID NO: 60 | CTCCTCTGACTGTAACCACGGCGCGTGCGGTTGAACAT GTCCCTGTACCCGTGCCCGATCGTGTGTGTGGGGTGT GCGGGCATAGGTAGTCCAGAAGCC |
| DLL4-SMG-21 SEQ ID NO: 61 | CTCCTCTGACTGTAACCACGGTGCGCGTGCGAGTCTGC GCGTCCTGCACATGTGTGTGTGTGTGCGTTCGGCGT GCGGGCATAGGTAGTCCAGAAGCC |
| DLL4-SMG-3 SEQ ID NO: 62 | CTCCTCTGACTGTAACCACGTCGGGTGATGCGGCGCAC ACACCGTGGCCACGTGCCAAGGTGTGTCTTTGCTGTGC GTGCGCATAGGTAGTCCAGAAGCC |
| DLL4-SMG-25 SEQ ID NO: 63 | CTCCTCTGACTGTAACCACGGCATGAGTTGGGGTACCAA TGTGTATTACGTATGCGTCGGGACACGAGTCTAATGTGT GTGCATAGGTAGTCCAGAAGCC |
| DLL4-SMG-24 SEQ ID NO: 64 | CTCCTCTGACTGTAACCACGGTGTGCGCGTTGCTACATG TTCGTTCTGCGGGCGGTGAGGTTCGTATGTTGTGTCCGT GTGCATAGGTAGTCCAGAAGCC |
| DLL4-SMG-19 SEQ ID NO: 65 | CTCCTCTGACTGTAACCACGGCGCGTGTGGAGGCGTAC ACGTAGCGCATCAGTGTCAGAGCATGTATACGGTGCAT GTGAGCATAGGTAGTCCAGAAGCC |
| DLL4-SMG-E25 SEQ ID NO: 66 | CTCCTCTGACTGTAACCACGACGGGTTTCGCCGCGTAC ATATCGAGTGGATGTGCTGCCGGGCGCTCTTCTCGTGC TCGTGCATAGGTAGTCCAGAAGCC |
| DLL4-SMG-E43 SEQ ID NO: 67 | CTCCTCTGACTGTAACCACGATGCGTGTTGTCATGCGCG TACAGGGTGCACGTGTACTCATGCGTGTGTATATCGTGT GTGCATAGGTAGTCCAGAAGCC |
| DLL4-SMG-E69 SEQ ID NO: 68 | CTCCTCTGACTGTAACCACGGCCCGTGCGCCAATACAA CTGTGCAATGTGTGTGCCGCTGTGTCTTCTTCCGGCGTG TGTGCATAGGTAGTCCAGAAGCC |
| DLL4-SMG-E24 SEQ ID NO: 69 | CTCCTCTGACTGTAACCACGTCGTGTGTGTGGGTGTACG CATTCTGTGCGCGTACCAGGCCACGCACGTCTCGCCTG TGTGCATAGGTAGTCCAGAAGCC |
| DLL4-SMG-E76 SEQ ID NO: 70 | CTCCTCTGACTGTAACCACGGTACACATAGCCATGTGAG CGCGCCGCGTGGATGTCCGCACTCATGCGTTTCGTACG TGCGCATAGGTAGTCCAGAAGCC |
| DLL4-SMG-E31 SEQ ID NO: 71 | CTCCTCTGACTGTAACCACGCCATGAACCGTGGCCCCT GCATCGCGCATATGTGTGATAGTGTGTGTGCTCTCCGCC TGGGCATAGGTAGTCCAGAAGCC |
| DLL4-SMG-E9 SEQ ID NO: 72 | CTCCTCTGACTGTAACCACGGCGCGCGCACCAATGTAC GCATATTTTGCTCGTATAGGTTTCCCTGCGTTGACTGTG TGGGCATAGGTAGTCCAGAAGCC |
| DLL4-SMG-E7 SEQ ID NO: 73 | CTCCTCTGACTGTAACCACGACGGGTACGTAGATCCGC GTATCGCGTGTAGGTACCGGGGTTCGTTGATCGAGTGT GTGCGCATAGGTAGTCCAGAAGCC |
| DLL4-SMG-E1 SEQ ID NO: 74 | CTCCTCTGACTGTAACCACGGCACGCATATCAGTGCACA CATCGCACACATGCACGCGAAAACCTGGGCCGCATGTG TGGGCATAGGTAGTCCAGAAGCC |

Flow cytometry data showed that DLL4-SMG-E25, E43, E69, E24, E76, E31, E9, E7 and E1 had the best switching capability. This data is reproduced at FIGS. 13A-F Example 14

Cloning and Sequencing of High Affinity SwAps to Plasminogen Activator, Urokinase Receptor (PLAUR)

An aptamer pool selected specifically to PLUR/PLAUR) positive cells and which showed both high affinity and switchability was selected for cloning to obtain individual aptamer sequences to the NRP receptor. The resulting sequences are provided in SEQ ID NOs: 75 through 89, also reproduced below at Table 8. Briefly, the pool was amplified, purified and cloned using the same method as described in Example 5 above.

TABLE 8

| | |
|---|---|
| PLUR-SMG-72 SEQ ID NO: 75 | CTCCTCTGACTGTAACCACGCATAGGTAGTCCAGAAGCCAGCC TCCTTTGACTGTAACCACGGCATAGGTAGTTCAGATGTGCATA GGTAGTCCAGAAGCC |
| PLUR-SMG-95 SEQ ID NO: 76 | CTCCTCTGACTGTAACCACGGCATGTGTACCGGTGTATGCATG CAGCGCACATGTTCCCGAATGTGCGTCGAGTGCGCGTGCATAG GTAGTCCAGAAGCC |
| PLUR-SMG-62 SEQ ID NO: 77 | CTCCTCTGACTGTAACCACGGCATGTTCGGTAGCGCGTATGTG CAGTTCGCGTGTTTATGCCTCGACGTAGTGTGCGCGTGCATAG GTAGTCCAGAAGCC |

TABLE 8 -continued

| | |
|---|---|
| PLUR-SMG-5 SEQ ID NO: 78 | CTCCTCTGACTGTAACCACGCCATACTTGGTGGTCTGTGCGTG AGGCGAGTGTGCATCGGCATGCGTCTGCGGTGTGCGTGCATAG GTAGTCCAGAAGCC |
| PLUR-SMG-29 SEQ ID NO: 79 | CTCCTCTGACTGTAACCACGACGTGTGCCCGGGTGAACCGGCG CAGCGCGTGTATGGTTATGCATGTGTCAGGTCCGTGCGCATAG GTAGTCCAGAAGCC |
| PLUR-SMG-66 SEQ ID NO: 80 | CTCCTCTGACTGTAACCACGACGCACTTTTGGGGTTGTATGCG GGGTGCGCACACGTCCGGACATGTGTCCTTCGTTCGTGCATAG GTAGTCCAGAAGCC |
| PLUR-SMG-113 SEQ ID NO: 81 | CTCCTCTGACTGTAACCACGGCATGCGTCAGCATGGGTGCATC CAGCGTGCGCGTCGAAGGATGTGAATCTTGTGTATGCGCATAG GTAGTCCAGAAGCC |
| PLU R-SMG-25 SEQ ID NO: 82 | CTCCTCTGACTGTAACCACGACACATGCAGTGGTGTTTGTGTC ATGCGTACATGTCTACGTGTGCGAGTTTGATGCGCGTGCATAG GTAGTCCAGAAGCC |
| PLUR-SMG-27 SEQ ID NO: 83 | CTCCTCTGACTGTAACCACGATGCGCGTTCGTGTGCGTAGGTT GGGTATGTGCGTTTGAGTATGTGGACGTCGTGTGGGGCATAG GTAGTCCAGAAGCC |
| PLUR-SMG-E50 SEQ ID NO: 84 | CTCCTCTGACTGTAACCACGCTCTGTGGCGTTATGCGCGTGTC CAGTGTGTTCCCTGACATGTATGAGTTCGATACGCGGGCATAG GTAGTCCAGAAGCC |
| PLUR-SMG-E13 SEQ ID NO: 85 | CTCCTCTGACTGTAACCACGGCGTCGGAGTGTGCATGTTCGTC TGATGCGCGGATGTCTCCTCATGTGTCGTGCGTATGTGCATAG GTAGTCCAGAAGCC |
| PLUR-SMG-E76 SEQ ID NO: 86 | CTCCTCTGACTGTAACCACGGCACACGATTAGGCGCGGGACC CTGTGTGTATCGCGTGATACGTATGCGCAGTACGCGTGCATAG GTAGTCCAGAAGCC |
| PLUR-SMG-E35 SEQ ID NO: 87 | CTCCTCTGACTGTAACCACGGTGTATGTGGCTGTAGGTGCGTG CGGTTTGTGTGTCACGGTAAGCTTGCCCGGTGTGTGTGCATAG GTAGTCCAGAAGCC |
| PLUR-SMG-E20 SEQ ID NO: 88 | CTCCTCTGACTGTAACCACGATACGGGTAAACGCGAGCGTGCA TGAAGTGATTGACGGCGCAGGCCTGTGGAGTGGGCAGGCATA GGTAGTCCAGAAGCC |
| PLUR-SMG-E31 SEQ ID NO: 89 | CTCCTCTGACTGTAACCACGGAGTGCGTGGCTAAGCGCGTCTC GGGTTTCCATATTGCTGTGTGTGCATCCACCATGTGCGCATAG GTAGTCCAGAAGCC |

Flow cytometry data indicated that PLAUR-SMG-E50, E13, E76, E35, E20 and E31 had the best switching capability. This data is reproduced at FIGS. 14A-I. PLAUR titration data is reproduced at FIGS. 15A-H.

The scope of the disclosure should not be limited by the embodiments set forth in the examples but should be given the broadest interpretation consistent with the description as a whole. The claims are not to be limited to the preferred or exemplified embodiments of the disclosure.

REFERENCES

To the extent that external references may be incorporated by reference into the present specification, all references identified herein are incorporated into this specification by reference in their entirety.

Ayyar, B. V.; Arora, S.; Murphy, C.; O'Kennedy, R. *Methods* 2012, 56, 116.

Berezovski M V, Lechmann M, Musheev M U, Mak T W, Krylov S N. "Aptamer-facilitated biomarker discovery (AptaBiD)" J Am Chem Soc. 2008 Jul. 16; 130(28):9137-43.

Carrasquilla C, Li Y, Brennan J D. Surface immobilization of structure-switching DNA aptamers on macroporous sol-gel-derived films for solid-phase biosensing applications. Anal Chem. 2011 Feb. 1; 83(3):957-65)

Darfeuille, F.; S. Reigadas, J. Hansen, H. Orum, C. Di Primo, J. Toulme (2006). "Aptamers targeted to an RNA hairpin show improved specificity compared to that of complementary oligonucleotides" Biochemistry 45: 12076-12082.

Deng Q P, Tie C, Zhou Y L, Zhang X X, Cocaine detection by structure-switch aptamer-based capillary zone electrophoresis, Electrophoresis. 2012 May; 33(9-10):1465-70.

Diallo, J.; Vähä-Koskela, M.; Le Boeuf, F.; Bell, J. *Methods in Molecular Biology* 2012, 127.

Fitzgerald, J.; Leonard, P.; Darcy, E.; O'Kennedy, R. *Methods Mol Biol* 2011, 681, 35.

Jiang, Y.; Fang, X.; Bai, a. C. *Analytical Chemistry* 2004, 5230.

Jeong, S.; S. R. Han, Y. J. Lee, S. W. Lee (2010). "Selection of RNA aptamers specific to active prostate-specific antigen." Biotechnology Letters 32: 379-85.

Liu, M.; T. Kagahara, H. Abe, Y. Ito (2009). "Direct In Vitro Selection of Hemin-Binding DNA Aptamer with Peroxidase Activity". Bulletin of the Chemical Society of Japan 82: 99-104.

Long, S.; M. Long, R. White, B. Sullenger (2008). "Crystal structure of an RNA aptamer bound to thrombin". RNA 14 (2): 2504-2512.

Min, K.; M. Cho, S. Han, Y. Shim, J. Ku, C. Ban (2008). "A simple and direct electrochemical detection of interferon-gamma using its RNA and DNA aptamers." Biosensors & Bioelectronics 23: 1819-1824.

Ng E. W. M; D. T. Shima, P. Calias, E. T. Cunningham, D. R. Guyer, A. P. Adamis (2006). "Pegaptanib, a targeted anti-VEGF aptamer for ocular vascular disease." Nature Reviews Drug Discovery 5 (2): 123-132.

Potty, A.; K. Kourentzi, H. Fang, G. Jackson, X. Zhang, G. Legge, R. Willson (2009). "Biophysical Characterization of DNA Aptamer Interactions with Vascular Endothelial Growth Factor", Biopolymers 91: 145-156.

Romig T S, Bell C, Drolet D W. J Chromatogr B Biomed Sci Appl. 1999 Aug. 20; 731(2):275-84.

Savory, N.; K. Abe, K. Sode, K. Ikebukuro (2010). "Selection of DNA aptamer against prostate specific antigen using a genetic algorithm and application to sensing." Biosensors & Bioelectronics 15: 1386-91.

Sefah et al. (Sefah K, Phillips J A, Xiong X, Meng L, Van Simaeys D, Chen H, Martin J, Tan W. Nucleic acid aptamers for biosensors and bio-analytical applications. Analyst. 2009 September; 134(9):1765-75.

Wei, S.; Mizaikoff, B. *J Sep Sci* 2007, 30, 1794.

Yang, H.; Gurgel, P. V.; Carbonell, R. G. *J Chromatogr A* 2009, 1216, 910.

Zhu Z, Ravelet C, Perrier S, Guieu V, Roy B, Perigaud C, Peyrin E. Multiplexed detection of small analytes by structure-switching aptamer-based capillary electrophoresis. Anal Chem. 2010 Jun. 1; 82(11):4613-20.

The invention claimed is:

1. A switchable aptamer which is obtained through a method comprising:
   a) incubating a pool comprising a mixture of aptamers with a target ligand and a binding ion to form target-aptamer complexes comprising said target ligand and aptamers specific to said target;
   b) separating unbound aptamer molecules from the target-aptamer complexes;
   c) contacting the target-aptamer complexes with a chelating agent having affinity for said binding ion wherein a switchable aptamer specific to said target is released from the target-aptamer complexes; and
   d) isolating the switchable aptamer released in step c;
   wherein the switchable aptamer comprises a nucleotide sequence represented in any one of SEQ ID NOS: 31 through 47 or a nucleotide sequence with at least 70%, 75%, 80%, 85%, 90%, 95% or 99% identity with any one of SEQ ID NOS: 31 through 47.

2. The switchable aptamer of claim 1 wherein said binding ion is calcium or magnesium or a combination thereof.

3. A method for purifying a selected target from a complex mixture, the method comprising the steps of:
   a) incubating switchable aptamer with the complex mixture in the presence of a binding ion to produce target-aptamer complexes wherein the switchable aptamer comprises a nucleotide sequence represented in any one of SEQ ID NOS: 31 through 47 or a nucleotide sequence with at least 70%, 75%, 80%, 85%, 90%, 95% or 99% identity with any one of SEQ ID NOS: 31 through 47;
   b) separating the target-aptamer complexes from unbound components of the complex mixture;
   c) adding a chelating agent having affinity for the binding ion to the target-aptamer complexes to release the target from the target-aptamer complexes; and
   d) separating the released target from said switchable aptamer.

4. The method of claim 3 performed at a maximum temperature of 25° C.

5. The method of claim 3 wherein the binding ion is calcium or magnesium or a combination thereof.

6. The method of claim 3 wherein the chelating agent is ethylenediaminetetraacetic acid (EDTA) or ethylene glycol tetraacetic acid (EGTA) or a combination thereof.

7. The method of claim 3 wherein the target is a virus, a cell or an antibody.

8. The method of claim 7 wherein the virus is Vesicular Stomatis Virus (VSV).

9. The method of claim 7 wherein said cell is a eukaryote.

10. The method of claim 9 wherein said cell is receptor positive for one of: a Neuropilin 1 (NRP) receptor, a Leukemia inhibitory factor (LIF) receptor, a Patched 1 (PTCH1) receptor, a Delta-Like Ligand 4 (0114) receptor or a plasminogen activator/urokinase receptor (PLAUR).

11. The method of claim 3 wherein target-aptamer complexes are separated from the unbound components of the complex mixture using a magnetic field or by elution.

12. The method of claim 3 comprising the further step of re-using the separated switchable aptamer to repeat said steps a) through d) on the same or a different complex mixture.

13. The method of claim 3 wherein said switchable aptamer is obtained through a method comprising:
   a) incubating said pool with said target ligand and a binding ion to form target-aptamer complexes comprising said target ligand and aptamers specific to said target;
   b) separating unbound aptamer molecules from the target-aptamer complexes;
   c) contacting the target-aptamer complexes with a chelating agent having affinity for said binding ion wherein a switchable aptamer specific to said target is released from the target-aptamer complexes; and
   d) isolating the switchable aptamer released in step c.

14. A switchable aptamer comprising the nucleotide sequence of SEQ ID NO: 43, or a nucleotide sequence with at least 70%, 75%, 80%, 85%, 90%, 95% or 99% identity with SEQ ID NO: 43.

* * * * *

SEQUENCE LISTING

```
<160> NUMBER OF SEQ ID NOS: 92

<210> SEQ ID NO 1
<211> LENGTH: 20
<212> TYPE: DNA
<213> ORGANISM: Artificial Sequence
<220> FEATURE:
<223> OTHER INFORMATION: Forward Primer Sequence

<400> SEQUENCE: 1
ctcctctgac tgtaaccacg                                                   20

<210> SEQ ID NO 2
<211> LENGTH: 20
<212> TYPE: DNA
<213> ORGANISM: Artificial Sequence
<220> FEATURE:
<223> OTHER INFORMATION: Reverse Primer Sequence

<400> SEQUENCE: 2
gcataggtag tccagaagcc                                                   20

<210> SEQ ID NO 3
<211> LENGTH: 80
<212> TYPE: DNA
<213> ORGANISM: Artificial Sequence
<220> FEATURE:
<223> OTHER INFORMATION: SwAp1

<400> SEQUENCE: 3
ctcctctgac tgtaaccacg cgccctcaga acttttgtat ccgaacacct gcatcgtccg       60
ggcttctgga ctacctatgc                                                   80

<210> SEQ ID NO 4
<211> LENGTH: 80
<212> TYPE: DNA
<213> ORGANISM: Artificial Sequence
<220> FEATURE:
<223> OTHER INFORMATION: SwAp2

<400> SEQUENCE: 4
ctcctctgac tgtaaccacg taccacccgt gacgcgcaca tccctcctct gttctccgcg       60
ggcttctgga ctacctatgc                                                   80

<210> SEQ ID NO 5
<211> LENGTH: 80
<212> TYPE: DNA
<213> ORGANISM: Artificial Sequence
<220> FEATURE:
<223> OTHER INFORMATION: SwAp3

<400> SEQUENCE: 5
ctcctctgac tgtaaccacg tgcccctcc atcccgagta acctacgtcc atgtctcgct        60
ggcttctgga ctacctatgc                                                   80

<210> SEQ ID NO 6
<211> LENGTH: 80
<212> TYPE: DNA
<213> ORGANISM: Artificial Sequence
<220> FEATURE:
<223> OTHER INFORMATION: SwAp4

<400> SEQUENCE: 6
ctcctctgac tgtaaccacg tgcccctcc atcccgagta acctacgtcc atgtctcgct        60
```
ggcttctgga ctacctatgc                                              80

<210> SEQ ID NO 7
<211> LENGTH: 80
<212> TYPE: DNA
<213> ORGANISM: Artificial Sequence
<220> FEATURE:
<223> OTHER INFORMATION: SwAp5

<400> SEQUENCE: 7
ctcctctgac tgtaaccacg taccacccgt gaccctcaca tccctcctct gttctccgcg    60
ggcttctgga ctacctatgc                                              80

<210> SEQ ID NO 8
<211> LENGTH: 80
<212> TYPE: DNA
<213> ORGANISM: Artificial Sequence
<220> FEATURE:
<223> OTHER INFORMATION: SwAp6

<400> SEQUENCE: 8
ctcctctgac tgtaaccacg tggcactgtt gtcatcactg tcccccccta actcgtccgt    60
ggcttctgga ctacctatgc                                              80

<210> SEQ ID NO 9
<211> LENGTH: 80
<212> TYPE: DNA
<213> ORGANISM: Artificial Sequence
<220> FEATURE:
<223> OTHER INFORMATION: SwAp7

<400> SEQUENCE: 9
ctcctctgac tgtaaccacg taccacccgt ggccctcaca tccctcctct gttctccgcg    60
ggcttctgga ctacctatgc                                              80

<210> SEQ ID NO 10
<211> LENGTH: 84
<212> TYPE: DNA
<213> ORGANISM: Artificial Sequence
<220> FEATURE:
<223> OTHER INFORMATION: SwAp8

<400> SEQUENCE: 10
ctcctctgac tgtaaccacg taccacccgt gaccctcaca tccctcctct gacgtaacca    60
cgcgggcttc tggactacct atgc                                         84

<210> SEQ ID NO 11
<211> LENGTH: 80
<212> TYPE: DNA
<213> ORGANISM: Artificial Sequence
<220> FEATURE:
<223> OTHER INFORMATION: SwAp9

<400> SEQUENCE: 11
ctcctctgac tgtaaccacg taccacccgt ggccctcaca tccctcctct gttctccgcg    60
ggcttctgga ctacctatgc                                              80

<210> SEQ ID NO 12
<211> LENGTH: 80
<212> TYPE: DNA
<213> ORGANISM: Artificial Sequence
<220> FEATURE:

<223> OTHER INFORMATION: SwAp10

<400> SEQUENCE: 12
ctcctctgac tgtaaccacg taccgcccgt gaccctcaca tccctcctct gttctccgcg    60
ggcttctgga ctacctatgc    80

<210> SEQ ID NO 13
<211> LENGTH: 79
<212> TYPE: DNA
<213> ORGANISM: Artificial Sequence
<220> FEATURE:
<223> OTHER INFORMATION: SwAp11

<400> SEQUENCE: 13
tcctctgact gtaaccacgc agccaccata ctgtcccgtt tgccccgcc gattccgtcg    60 gcttctggac tacctatgc    79

<210> SEQ ID NO 14
<211> LENGTH: 80
<212> TYPE: DNA
<213> ORGANISM: Artificial Sequence
<220> FEATURE:
<223> OTHER INFORMATION: SwAp12

<400> SEQUENCE: 14
ctcctctgac tgtaaccacg taccacccgt gaccttaca tccctcctct gttctccgcg    60
ggcttctgga ctacctatgc    80

<210> SEQ ID NO 15
<211> LENGTH: 80
<212> TYPE: DNA
<213> ORGANISM: Artificial Sequence
<220> FEATURE:
<223> OTHER INFORMATION: SwAp13

<400> SEQUENCE: 15
ctcctctgac tgtaaccacg taccacccgt gaccctcaca tccctcctct gttctccgcg    60
ggcttctgga ctacctatgc    80

<210> SEQ ID NO 16
<211> LENGTH: 80
<212> TYPE: DNA
<213> ORGANISM: Artificial Sequence
<220> FEATURE:
<223> OTHER INFORMATION: SwAp14

<400> SEQUENCE: 16
ctcctctgac tgtaaccacg taccaccctt gaccctcaca tccctcctct gttctccgcg    60
ggcttctgga ctacctatgc    80

<210> SEQ ID NO 17
<211> LENGTH: 80
<212> TYPE: DNA
<213> ORGANISM: Artificial Sequence
<220> FEATURE:
<223> OTHER INFORMATION: SwAp 15

<400> SEQUENCE: 17
ctcctctgac tgtaaccacg gcaccccgag gcaatttcgc gcatagttca tcctgtttgg    60
ggcttctgga ctacctatgc    80

```
<210> SEQ ID NO 18
<211> LENGTH: 79
<212> TYPE: DNA
<213> ORGANISM: Artificial Sequence
<220> FEATURE:
<223> OTHER INFORMATION: Pool 10
<220> FEATURE:
<221> NAME/KEY: misc_feature
<222> LOCATION: (21)..(59)
<223> OTHER INFORMATION: n is a, c, g, or t

<400> SEQUENCE: 18
ctcctctgac tgtaaccacg nnnnnnnnnn nnnnnnnnnn nnnnnnnnnn nnnnnnnnng      60
gcttctggac tacctatgc                                                  79

<210> SEQ ID NO 19
<211> LENGTH: 20
<212> TYPE: DNA
<213> ORGANISM: Artificial Sequence
<220> FEATURE:
<223> OTHER INFORMATION: Forward Primer

<400> SEQUENCE: 19
cgtggttaca gtcagaggag                                                 20

<210> SEQ ID NO 20
<211> LENGTH: 20
<212> TYPE: DNA
<213> ORGANISM: Artificial Sequence
<220> FEATURE:
<223> OTHER INFORMATION: Reverse Primer

<400> SEQUENCE: 20
ggcttctgga ctacctatgc                                                 20

<210> SEQ ID NO 21
<211> LENGTH: 100
<212> TYPE: DNA
<213> ORGANISM: Artificial Sequence
<220> FEATURE:
<223> OTHER INFORMATION: NRP-SMG-20

<400> SEQUENCE: 21
ctcctctgac tgtaaccacg gcgtgcctca tggtgcgtgt gccaagtgtg cgtgtaatga      60
cattcgtgaa aagtgcgcgg gcataggtag tccagaagcc                          100

<210> SEQ ID NO 22
<211> LENGTH: 100
<212> TYPE: DNA
<213> ORGANISM: Artificial Sequence
<220> FEATURE:
<223> OTHER INFORMATION: NRP-SMG-19

<400> SEQUENCE: 22
ctcctctgac tgtaaccacg gcgcgcgttt gcacatgtgc gtgcgacata tgcgtggggg      60
gagatgtatg agacgtgtgg gcataggtag tccagaagcc                          100

<210> SEQ ID NO 23
<211> LENGTH: 100
<212> TYPE: DNA
<213> ORGANISM: Artificial Sequence
<220> FEATURE:
<223> OTHER INFORMATION: NRP-SMG-4

<400> SEQUENCE: 23
```

```
ctcctctgac tgtaaccacg gcgcgttcct ggtagctcat gcgtggcgtg gacacatgca    60
ggtgcgggtt gcctgtgtgg gcataggtag tccagaagcc                          100
```

<210> SEQ ID NO 24
<211> LENGTH: 100
<212> TYPE: DNA
<213> ORGANISM: Artificial Sequence
<220> FEATURE:
<223> OTHER INFORMATION: NRP-SMG-12

<400> SEQUENCE: 24

```
ctcctctgac tgtaaccacg cgagtcgcct acgtacgcac acttaccgcg cacgtccggg    60
caggcgtgtc ccgtgcatgc gcataggtag tccagaagcc                          100
```

<210> SEQ ID NO 25
<211> LENGTH: 100
<212> TYPE: DNA
<213> ORGANISM: Artificial Sequence
<220> FEATURE:
<223> OTHER INFORMATION: NRP-SMG-6

<400> SEQUENCE: 25

```
ctcctctgac tgtaaccacg gtgtacactg gcacacgcac atgtcatccg cgcggggctg    60
cacacgtcag ccgtgtgtgg gcataggtag tccagaagcc                          100
```

<210> SEQ ID NO 26
<211> LENGTH: 100
<212> TYPE: DNA
<213> ORGANISM: Artificial Sequence
<220> FEATURE:
<223> OTHER INFORMATION: NRP-SMG-14

<400> SEQUENCE: 26

```
ctcctctgac tgtaaccacg gcgtacgtga ccccatacgc actctagcca catacgttcg    60
cccacgcctg tcgctcgcgg gcataggtag tccagaagcc                          100
```

<210> SEQ ID NO 27
<211> LENGTH: 100
<212> TYPE: DNA
<213> ORGANISM: Artificial Sequence
<220> FEATURE:
<223> OTHER INFORMATION: NRP-SMG-1

<400> SEQUENCE: 27

```
ctcctctgac tgtaaccacg gtgtgcctgc ttgctgatgt gtgttgtcgg tgcgtgaggg    60
cgtacgtaag tgtcgtgcgg gcataggtag tccagaagcc                          100
```

<210> SEQ ID NO 28
<211> LENGTH: 100
<212> TYPE: DNA
<213> ORGANISM: Artificial Sequence
<220> FEATURE:
<223> OTHER INFORMATION: NRP-SMG-E1

<400> SEQUENCE: 28

```
ctcctctgac tgtaaccacg gtctgcacta tggtgcgtgc gttcggtgta cccatgagcg    60
tccatgtgtg agttgctcgg gcataggtag tccagaagcc                          100
```

<210> SEQ ID NO 29
<211> LENGTH: 100
<212> TYPE: DNA
<213> ORGANISM: Artificial Sequence

```
<220> FEATURE:
<223> OTHER INFORMATION: NRP-SMG-E2

<400> SEQUENCE: 29
ctcctctgac tgtaaccacg gtctgcacta tggtgcgtgc gttcggtgta cccatgagcg      60
tccatgtgtg agttgctcgg gcataggtag tccagaagcc                          100

<210> SEQ ID NO 30
<211> LENGTH: 100
<212> TYPE: DNA
<213> ORGANISM: Artificial Sequence
<220> FEATURE:
<223> OTHER INFORMATION: NRP-SMG-E3

<400> SEQUENCE: 30
ctcctctgac tgtaaccacg ctacatgtga gggcgcttgc atgcaatatg cagactctga      60
cgcgtgtgtt ggttgtgtgg gcataggtag tccagaagcc                          100

<210> SEQ ID NO 31
<211> LENGTH: 100
<212> TYPE: DNA
<213> ORGANISM: Artificial Sequence
<220> FEATURE:
<223> OTHER INFORMATION: LIF-SMG-1

<400> SEQUENCE: 31
ctcctctgac tgtaaccacg gtagctatgg ccacgtgcac attcagtatg cacgttaatg      60
ctcgcatgtc gtacgcgtgg gcataggtag tccagaagcc                          100

<210> SEQ ID NO 32
<211> LENGTH: 100
<212> TYPE: DNA
<213> ORGANISM: Artificial Sequence
<220> FEATURE:
<223> OTHER INFORMATION: LIF-SMG-12

<400> SEQUENCE: 32
ctcctctgac tgtaaccacg ccaccgtct ttgtgcatgc ttgtactgca tacatctcgc       60
cacacgcgta cagcacacgt gcataggtag tccagaagcc                          100

<210> SEQ ID NO 33
<211> LENGTH: 101
<212> TYPE: DNA
<213> ORGANISM: Artificial Sequence
<220> FEATURE:
<223> OTHER INFORMATION: LIF-SMG-5

<400> SEQUENCE: 33
ctcctctgac tgtaaccacg ggcataggcg ggtgtgtatc tgccaagcgc gtgcttgctg      60
attctcgcgc gaatcacagg cgcataggta gtccagaagc c                        101

<210> SEQ ID NO 34
<211> LENGTH: 100
<212> TYPE: DNA
<213> ORGANISM: Artificial Sequence
<220> FEATURE:
<223> OTHER INFORMATION: LIF-SMG-8

<400> SEQUENCE: 34
ctcctctgac tgtaaccacg gtgcaggtga gagcatgtgc gtgtcatggt cgaaccgtgg      60
cgcttgcatt gggtgtgcgt gcataggtag tccagaagcc                          100
```

<210> SEQ ID NO 35
<211> LENGTH: 100
<212> TYPE: DNA
<213> ORGANISM: Artificial Sequence
<220> FEATURE:
<223> OTHER INFORMATION: LIF-SMG-9

<400> SEQUENCE: 35
ctcctctgac tgtaaccacg gcgtacatcc ccacacgtgc gtattacgtg ctcccccgtg     60
cgtgtcggtg gagcgtgtgt gcataggtag tccagaagcc                         100

<210> SEQ ID NO 36
<211> LENGTH: 100
<212> TYPE: DNA
<213> ORGANISM: Artificial Sequence
<220> FEATURE:
<223> OTHER INFORMATION: LIF-SMG-10

<400> SEQUENCE: 36
ctcctctgac tgtaaccacg ctgcatccta gggtctatgc ctaggggct gctatgcgtg     60 cacgcgtgtc ggtcatgtgg gcataggtag tccagaagcc                         100

<210> SEQ ID NO 37
<211> LENGTH: 100
<212> TYPE: DNA
<213> ORGANISM: Artificial Sequence
<220> FEATURE:
<223> OTHER INFORMATION: LIF-SMG-21

<400> SEQUENCE: 37
ctcctctgac tgtaaccacg gcatgtttcc ccgcgtgtgc atttgacgtg tgtgtcccca    60
cgcacgtatc acgcaagggg gcataggtag tccagaagcc                         100

<210> SEQ ID NO 38
<211> LENGTH: 100
<212> TYPE: DNA
<213> ORGANISM: Artificial Sequence
<220> FEATURE:
<223> OTHER INFORMATION: LIF-SMG-11

<400> SEQUENCE: 38
ctcctctgac tgtaaccacg gcgtgcacct ccgcgtatgg cttgcatatg agtgctgttc    60
tccgtatttc ggacatacgg gcataggtag tccagaagcc                         100

<210> SEQ ID NO 39
<211> LENGTH: 100
<212> TYPE: DNA
<213> ORGANISM: Artificial Sequence
<220> FEATURE:
<223> OTHER INFORMATION: LIF-SMG-16

<400> SEQUENCE: 39
ctcctctgac tgtaaccacg gcacatatct tgctgcccac gtgccaccac cgtgtctccc    60
tgcccatccg aagtgcgcgc gcataggtag tccagaagcc                         100

<210> SEQ ID NO 40
<211> LENGTH: 100
<212> TYPE: DNA
<213> ORGANISM: Artificial Sequence
<220> FEATURE:
<223> OTHER INFORMATION: LIF-SMG-E46

<400> SEQUENCE: 40

```
ctcctctgac tgtaaccacg gcacctgagt ctgtccgtcc gcttgacacg cacgcaaggg      60
tatgcgcatc ccacacgcgc gcataggtag tccagaagcc                           100

<210> SEQ ID NO 41
<211> LENGTH: 100
<212> TYPE: DNA
<213> ORGANISM: Artificial Sequence
<220> FEATURE:
<223> OTHER INFORMATION: LIF-SMG-E8

<400> SEQUENCE: 41
ctcctctgac tgtaaccacg gcgcgtatcc ccgagtgcgt acgcggtgtt tgctcgatcg      60
tacgtgcatg gtgtgcgtgt gcataggtag tccagaagcc                           100

<210> SEQ ID NO 42
<211> LENGTH: 199
<212> TYPE: DNA
<213> ORGANISM: Artificial Sequence
<220> FEATURE:
<223> OTHER INFORMATION: LIF-SMG-E16

<400> SEQUENCE: 42
ctcctctgac tgtaaccacg gcgtgtgtcc cggtgtgcgc atagtccaag tacgtcgccg      60
tgtgtacgtt caatgcgtgg gcataggtag tccagaagcc tcctctgact gtaaccacgg    120
tgcgtatgga cacgtctgta ctgagtgcgc atgttgagac gcatgcgtcg tgcgtgtgtg    180
cataggtagt ccagaagcc                                                 199

<210> SEQ ID NO 43
<211> LENGTH: 100
<212> TYPE: DNA
<213> ORGANISM: Artificial Sequence
<220> FEATURE:
<223> OTHER INFORMATION: LIF-SMG-E6

<400> SEQUENCE: 43
ctcctctgac tgtaaccacg gtgcgtatgg acacgtctgt actgagtgcg catgttgaga      60
cgcatgcgtc gtgcgtgtgt gcataggtag tccagaagcc                           100

<210> SEQ ID NO 44
<211> LENGTH: 100
<212> TYPE: DNA
<213> ORGANISM: Artificial Sequence
<220> FEATURE:
<223> OTHER INFORMATION: LIF-SMG-E45

<400> SEQUENCE: 44
ctcctctgac tgtaaccacg gtgcatgtgt cggtatgcgg gccgcttgtg cgtgtgacga      60
ctcgtgtgtg taatgcgcgc gcataggtag tccagaagcc                           100

<210> SEQ ID NO 45
<211> LENGTH: 99
<212> TYPE: DNA
<213> ORGANISM: Artificial Sequence
<220> FEATURE:
<223> OTHER INFORMATION: LIF-SMG-E13

<400> SEQUENCE: 45
tcctctgact gtaaccacgc catgcacccg tgtgtgtgtg gtgtacgtgt gtgtccacgg      60
gaacgtatca cgtcataggg cataggtagt ccagaagcc                            99
```

<210> SEQ ID NO 46
<211> LENGTH: 100
<212> TYPE: DNA
<213> ORGANISM: Artificial Sequence
<220> FEATURE:
<223> OTHER INFORMATION: LIF-SMG-E7

<400> SEQUENCE: 46
ctcctctgac tgtaaccacg gcgcgtgcgt aggcataggt gtcgtgtacg cgtgtctcag    60
cgcaattgcg tcgggtgtgt gcataggtag tccagaagcc    100

<210> SEQ ID NO 47
<211> LENGTH: 100
<212> TYPE: DNA
<213> ORGANISM: Artificial Sequence
<220> FEATURE:
<223> OTHER INFORMATION: LIF-SMG-E55

<400> SEQUENCE: 47
ctcctctgac tgtaaccacg gcatgcggtc tcgcactcgg ttctagtgtc cacgcttgtg    60
tatgcgtgcg cggtgtgtgt gcataggtag tccagaagcc    100

<210> SEQ ID NO 48
<211> LENGTH: 100
<212> TYPE: DNA
<213> ORGANISM: Artificial Sequence
<220> FEATURE:
<223> OTHER INFORMATION: PTCH1-SMG-17

<400> SEQUENCE: 48
ctcctctgac tgtaaccacg ccgcgagttg ccacacatgc acttctcaca catacccgtg    60
tacacgtaca gcacatatgc gcataggtag tccagaagcc    100

<210> SEQ ID NO 49
<211> LENGTH: 100
<212> TYPE: DNA
<213> ORGANISM: Artificial Sequence
<220> FEATURE:
<223> OTHER INFORMATION: PTCH1-SMG-22

<400> SEQUENCE: 49
ctcctctgac tgtaaccacg ccgcgagttg ccacacatgc acttctcaca catacccgtg    60
tacacgtaca gcacatatgc gcataggtag tccagaagcc    100

<210> SEQ ID NO 50
<211> LENGTH: 100
<212> TYPE: DNA
<213> ORGANISM: Artificial Sequence
<220> FEATURE:
<223> OTHER INFORMATION: PTCH1-SMG-16

<400> SEQUENCE: 50
ctcctctgac tgtaaccacg cccaatcccg caccacgtgc atgccacgcc cacgcatgag    60
tacacacgta cggcgcatgt gcataggtag tccagaagcc    100

<210> SEQ ID NO 51
<211> LENGTH: 100
<212> TYPE: DNA
<213> ORGANISM: Artificial Sequence
<220> FEATURE:
<223> OTHER INFORMATION: PTCH1-SMG-21

<400> SEQUENCE: 51

```
ctcctctgac tgtaaccacg cccaatcccg caccacgtgc atgccacgcc cacgcatgag    60
tacacacgta cggcgcatgt gcataggtag tccagaagcc                         100
```

<210> SEQ ID NO 52
<211> LENGTH: 100
<212> TYPE: DNA
<213> ORGANISM: Artificial Sequence
<220> FEATURE:
<223> OTHER INFORMATION: PTCH1-SMG-4

<400> SEQUENCE: 52

```
ctcctctgac tgtaaccacg gtgcctgcag ggacgcgtgt aaccggaatg tacgccgcga    60
cgcacacgcc tagtgtacgt gcataggtag tccagaagcc                         100
```

<210> SEQ ID NO 53
<211> LENGTH: 100
<212> TYPE: DNA
<213> ORGANISM: Artificial Sequence
<220> FEATURE:
<223> OTHER INFORMATION: PTCH1-SMG-11

<400> SEQUENCE: 53

```
ctcctctgac tgtaaccacg gtgcctgcag ggacgcgtgt aaccggaatg tacgccgcga    60
cgcacacgcc tagtgtacgt gcataggtag tccagaagcc                         100
```

<210> SEQ ID NO 54
<211> LENGTH: 100
<212> TYPE: DNA
<213> ORGANISM: Artificial Sequence
<220> FEATURE:
<223> OTHER INFORMATION: PTCH1-SMG-18

<400> SEQUENCE: 54

```
ctcctctgac tgtaaccacg gtacggtcgt cactgtgcgt acgctgtgca aagatgcaag    60
tgcgcatact gggtgtcggt gcataggtag tccagaagcc                         100
```

<210> SEQ ID NO 55
<211> LENGTH: 100
<212> TYPE: DNA
<213> ORGANISM: Artificial Sequence
<220> FEATURE:
<223> OTHER INFORMATION: PTCH1-SMG-23

<400> SEQUENCE: 55

```
ctcctctgac tgtaaccacg gtacggtcgt cactgtgcgt acgctgtgca aagatgcaag    60
tgcgcatact gggtgtcggt gcataggtag tccagaagcc                         100
```

<210> SEQ ID NO 56
<211> LENGTH: 100
<212> TYPE: DNA
<213> ORGANISM: Artificial Sequence
<220> FEATURE:
<223> OTHER INFORMATION: PTCH1-SMG-24

<400> SEQUENCE: 56

```
ctcctctgac tgtaaccacg ggacacgccg ggacgtgcat accggatgcg cacgtaatca    60
cctgtgggtg ggacgagccg gcataggtag tccagaagcc                         100
```

<210> SEQ ID NO 57
<211> LENGTH: 100
<212> TYPE: DNA

```
<213> ORGANISM: Artificial Sequence
<220> FEATURE:
<223> OTHER INFORMATION: PTCH1-SMG-E1

<400> SEQUENCE: 57
ctcctctgac tgtaaccacg acgcgcgatg cggcaagcat gttacgccca tgtatcttcg    60
tgcacatgcc ctccgtgtgt gcataggtag tccagaagcc                         100

<210> SEQ ID NO 58
<211> LENGTH: 68
<212> TYPE: DNA
<213> ORGANISM: Artificial Sequence
<220> FEATURE:
<223> OTHER INFORMATION: PTCH1-SMG-E2

<400> SEQUENCE: 58
ctcctctgac tgtaaccacg acactgtcct cctctgactg taaccacggc ataggtagtc    60
cagaagcc                                                            68

<210> SEQ ID NO 59
<211> LENGTH: 100
<212> TYPE: DNA
<213> ORGANISM: Artificial Sequence
<220> FEATURE:
<223> OTHER INFORMATION: PTCH1-SMG-E3

<400> SEQUENCE: 59
ctcctctgac tgtaaccacg acgcgcgatg cggcaagcat gttacgccca tgtatcttcg    60
tgcacatgcc ctccgtgtgt gcataggtag tccagaagcc                         100

<210> SEQ ID NO 60
<211> LENGTH: 100
<212> TYPE: DNA
<213> ORGANISM: Artificial Sequence
<220> FEATURE:
<223> OTHER INFORMATION: DLL4-SMG-10

<400> SEQUENCE: 60
ctcctctgac tgtaaccacg gcgcgtgcgg ttgaacatgt ccctgtacc cgtgcccgat     60 cgtgtgtgtg gggtgtgcgg gcataggtag tccagaagcc                         100

<210> SEQ ID NO 61
<211> LENGTH: 100
<212> TYPE: DNA
<213> ORGANISM: Artificial Sequence
<220> FEATURE:
<223> OTHER INFORMATION: DLL4-SMG-21

<400> SEQUENCE: 61
ctcctctgac tgtaaccacg gtgcgcgtgc gagtctgcgc gtcctgcaca tgtgtgtgtg    60
tgtgtgcgtt cggcgtgcgg gcataggtag tccagaagcc                         100

<210> SEQ ID NO 62
<211> LENGTH: 100
<212> TYPE: DNA
<213> ORGANISM: Artificial Sequence
<220> FEATURE:
<223> OTHER INFORMATION: DLL4-SMG-3

<400> SEQUENCE: 62
ctcctctgac tgtaaccacg tcgggtgatg cggcgcacac accgtggcca cgtgccaagg    60
tgtgtctttg ctgtgcgtgc gcataggtag tccagaagcc                         100
```

<210> SEQ ID NO 63
<211> LENGTH: 100
<212> TYPE: DNA
<213> ORGANISM: Artificial Sequence
<220> FEATURE:
<223> OTHER INFORMATION: DLL4-SMG-25

<400> SEQUENCE: 63
ctcctctgac tgtaaccacg gcatgagttg gggtaccaat gtgtattacg tatgcgtcgg    60
gacacgagtc taatgtgtgt gcataggtag tccagaagcc                         100

<210> SEQ ID NO 64
<211> LENGTH: 100
<212> TYPE: DNA
<213> ORGANISM: Artificial Sequence
<220> FEATURE:
<223> OTHER INFORMATION: DLL4-SMG-24

<400> SEQUENCE: 64
ctcctctgac tgtaaccacg gtgtgcgcgt tgctacatgt tcgttctgcg ggcggtgagg    60
ttcgtatgtt gtgtccgtgt gcataggtag tccagaagcc                         100

<210> SEQ ID NO 65
<211> LENGTH: 100
<212> TYPE: DNA
<213> ORGANISM: Artificial Sequence
<220> FEATURE:
<223> OTHER INFORMATION: DLL4-SMG-19

<400> SEQUENCE: 65
ctcctctgac tgtaaccacg gcgcgtgtgg aggcgtacac gtagcgcatc agtgtcagag    60
catgtatacg gtgcatgtga gcataggtag tccagaagcc                         100

<210> SEQ ID NO 66
<211> LENGTH: 100
<212> TYPE: DNA
<213> ORGANISM: Artificial Sequence
<220> FEATURE:
<223> OTHER INFORMATION: DLL4-SMG-E25

<400> SEQUENCE: 66
ctcctctgac tgtaaccacg acgggtttcg ccgcgtacat atcgagtgga tgtgctgccg    60
ggcgctcttc tcgtgctcgt gcataggtag tccagaagcc                         100

<210> SEQ ID NO 67
<211> LENGTH: 100
<212> TYPE: DNA
<213> ORGANISM: Artificial Sequence
<220> FEATURE:
<223> OTHER INFORMATION: DLL4-SMG-E43

<400> SEQUENCE: 67
ctcctctgac tgtaaccacg atgcgtgttg tcatgcgcgt acagggtgca cgtgtactca    60
tgcgtgtgta tatcgtgtgt gcataggtag tccagaagcc                         100

<210> SEQ ID NO 68
<211> LENGTH: 100
<212> TYPE: DNA
<213> ORGANISM: Artificial Sequence
<220> FEATURE:
<223> OTHER INFORMATION: DLL4-SMG-E69

```
<400> SEQUENCE: 68
ctcctctgac tgtaaccacg gcccgtgcgc caatacaact gtgcaatgtg tgtgccgctg      60
tgtcttcttc cggcgtgtgt gcataggtag tccagaagcc                          100

<210> SEQ ID NO 69
<211> LENGTH: 100
<212> TYPE: DNA
<213> ORGANISM: Artificial Sequence
<220> FEATURE:
<223> OTHER INFORMATION: DLL4-SMG-E24

<400> SEQUENCE: 69
ctcctctgac tgtaaccacg tcgtgtgtgt gggtgtacgc attctgtgcg cgtaccaggc      60
cacgcacgtc tcgcctgtgt gcataggtag tccagaagcc                          100

<210> SEQ ID NO 70
<211> LENGTH: 100
<212> TYPE: DNA
<213> ORGANISM: Artificial Sequence
<220> FEATURE:
<223> OTHER INFORMATION: DLL4-SMG-E76

<400> SEQUENCE: 70
ctcctctgac tgtaaccacg gtacacatag ccatgtgagc gcgccgcgtg gatgtccgca      60
ctcatgcgtt tcgtacgtgc gcataggtag tccagaagcc                          100

<210> SEQ ID NO 71
<211> LENGTH: 100
<212> TYPE: DNA
<213> ORGANISM: Artificial Sequence
<220> FEATURE:
<223> OTHER INFORMATION: DLL4-SMG-E31

<400> SEQUENCE: 71
ctcctctgac tgtaaccacg ccatgaaccg tggcccctgc atcgcgcata tgtgtgatag      60
tgtgtgtgct ctccgcctgg gcataggtag tccagaagcc                          100

<210> SEQ ID NO 72
<211> LENGTH: 100
<212> TYPE: DNA
<213> ORGANISM: Artificial Sequence
<220> FEATURE:
<223> OTHER INFORMATION: DLL4-SMG-E9

<400> SEQUENCE: 72
ctcctctgac tgtaaccacg gcgcgcgcac caatgtacgc atattttgct cgtataggtt      60
tccctgcgtt gactgtgtgg gcataggtag tccagaagcc                          100

<210> SEQ ID NO 73
<211> LENGTH: 100
<212> TYPE: DNA
<213> ORGANISM: Artificial Sequence
<220> FEATURE:
<223> OTHER INFORMATION: DLL4-SMG-E7

<400> SEQUENCE: 73
ctcctctgac tgtaaccacg acgggtacgt agatccgcgt atcgcgtgta ggtaccgggg      60
ttcgttgatc gagtgtgtgc gcataggtag tccagaagcc                          100

<210> SEQ ID NO 74
<211> LENGTH: 100
```

```
<212> TYPE: DNA
<213> ORGANISM: Artificial Sequence
<220> FEATURE:
<223> OTHER INFORMATION: DLL4-SMG-E1

<400> SEQUENCE: 74
ctcctctgac tgtaaccacg gcacgcatat cagtgcacac atcgcacaca tgcacgcgaa      60
aacctgggcc gcatgtgtgg gcataggtag tccagaagcc                           100

<210> SEQ ID NO 75
<211> LENGTH: 101
<212> TYPE: DNA
<213> ORGANISM: Artificial Sequence
<220> FEATURE:
<223> OTHER INFORMATION: PLUR-SMG-72

<400> SEQUENCE: 75
ctcctctgac tgtaaccacg cataggtagt ccagaagcca gcctcctttg actgtaacca     60
cggcataggt agttcagatg tgcataggta gtccagaagc c                         101

<210> SEQ ID NO 76
<211> LENGTH: 100
<212> TYPE: DNA
<213> ORGANISM: Artificial Sequence
<220> FEATURE:
<223> OTHER INFORMATION: PLUR-SMG-95

<400> SEQUENCE: 76
ctcctctgac tgtaaccacg gcatgtgtac cggtgtatgc atgcagcgca catgttcccg      60
aatgtgcgtc gagtgcgcgt gcataggtag tccagaagcc                           100

<210> SEQ ID NO 77
<211> LENGTH: 100
<212> TYPE: DNA
<213> ORGANISM: Artificial Sequence
<220> FEATURE:
<223> OTHER INFORMATION: PLUR-SMG-62

<400> SEQUENCE: 77
ctcctctgac tgtaaccacg gcatgttcgg tagcgcgtat gtgcagttcg cgtgtttatg      60
cctcgacgta gtgtgcgcgt gcataggtag tccagaagcc                           100

<210> SEQ ID NO 78
<211> LENGTH: 100
<212> TYPE: DNA
<213> ORGANISM: Artificial Sequence
<220> FEATURE:
<223> OTHER INFORMATION: PLUR-SMG-5

<400> SEQUENCE: 78
ctcctctgac tgtaaccacg ccatacttgg tggtctgtgc gtgaggcgag tgtgcatcgg      60
catgcgtctg cggtgtgcgt gcataggtag tccagaagcc                           100

<210> SEQ ID NO 79
<211> LENGTH: 100
<212> TYPE: DNA
<213> ORGANISM: Artificial Sequence
<220> FEATURE:
<223> OTHER INFORMATION: PLUR-SMG-29

<400> SEQUENCE: 79
ctcctctgac tgtaaccacg acgtgtgccc gggtgaaccg gcgcagcgcg tgtatggtta      60
```
tgcatgtgtc aggtccgtgc gcataggtag tccagaagcc                                    100

<210> SEQ ID NO 80
<211> LENGTH: 100
<212> TYPE: DNA
<213> ORGANISM: Artificial Sequence
<220> FEATURE:
<223> OTHER INFORMATION: PLUR-SMG-66

<400> SEQUENCE: 80
ctcctctgac tgtaaccacg acgcactttt ggggttgtat gcggggtgcg cacacgtccg    60
gacatgtgtc cttcgttcgt gcataggtag tccagaagcc                          100

<210> SEQ ID NO 81
<211> LENGTH: 100
<212> TYPE: DNA
<213> ORGANISM: Artificial Sequence
<220> FEATURE:
<223> OTHER INFORMATION: PLUR-SMG-113

<400> SEQUENCE: 81
ctcctctgac tgtaaccacg gcatgcgtca gcatgggtgc atccagcgtg cgcgtcgaag    60
gatgtgaatc ttgtgtatgc gcataggtag tccagaagcc                          100

<210> SEQ ID NO 82
<211> LENGTH: 100
<212> TYPE: DNA
<213> ORGANISM: Artificial Sequence
<220> FEATURE:
<223> OTHER INFORMATION: PLUR-SMG-25

<400> SEQUENCE: 82
ctcctctgac tgtaaccacg acacatgcag tggtgtttgt gtcatgcgta catgtctacg    60
tgtgcgagtt tgatgcgcgt gcataggtag tccagaagcc                          100

<210> SEQ ID NO 83
<211> LENGTH: 100
<212> TYPE: DNA
<213> ORGANISM: Artificial Sequence
<220> FEATURE:
<223> OTHER INFORMATION: PLUR-SMG-27

<400> SEQUENCE: 83
ctcctctgac tgtaaccacg atgcgcgttc gtgtgcgtag gttgggtatg tgcgtttgag    60
tatgtggacg tcgtgtgggg gcataggtag tccagaagcc                          100

<210> SEQ ID NO 84
<211> LENGTH: 100
<212> TYPE: DNA
<213> ORGANISM: Artificial Sequence
<220> FEATURE:
<223> OTHER INFORMATION: PLUR-SMG-E50

<400> SEQUENCE: 84
ctcctctgac tgtaaccacg ctctgtggcg ttatgcgcgt gtccagtgtg ttccctgaca    60
tgtatgagtt cgatacgcgg gcataggtag tccagaagcc                          100

<210> SEQ ID NO 85
<211> LENGTH: 100
<212> TYPE: DNA
<213> ORGANISM: Artificial Sequence
<220> FEATURE:
<223> OTHER INFORMATION: PLUR-SMG-E13

<400> SEQUENCE: 85
ctcctctgac tgtaaccacg gcgtcggagt gtgcatgttc gtctgatgcg cggatgtctc    60
ctcatgtgtc gtgcgtatgt gcataggtag tccagaagcc                        100

<210> SEQ ID NO 86
<211> LENGTH: 100
<212> TYPE: DNA
<213> ORGANISM: Artificial Sequence
<220> FEATURE:
<223> OTHER INFORMATION: PLUR-SMG-E76

<400> SEQUENCE: 86
ctcctctgac tgtaaccacg gcacacgatt aggcgcgggg accctgtgtg tatcgcgtga    60
tacgtatgcg cagtacgcgt gcataggtag tccagaagcc                        100

<210> SEQ ID NO 87
<211> LENGTH: 100
<212> TYPE: DNA
<213> ORGANISM: Artificial Sequence
<220> FEATURE:
<223> OTHER INFORMATION: PLUR-SMG-E35

<400> SEQUENCE: 87
ctcctctgac tgtaaccacg gtgtatgtgg ctgtaggtgc gtgcggtttg tgtgtcacgg    60
taagcttgcc cggtgtgtgt gcataggtag tccagaagcc                        100

<210> SEQ ID NO 88
<211> LENGTH: 100
<212> TYPE: DNA
<213> ORGANISM: Artificial Sequence
<220> FEATURE:
<223> OTHER INFORMATION: PLUR-SMG-E20

<400> SEQUENCE: 88
ctcctctgac tgtaaccacg atacgggtaa acgcgagcgt gcatgaagtg attgacggcg    60
caggcctgtg gagtgggcag gcataggtag tccagaagcc                        100

<210> SEQ ID NO 89
<211> LENGTH: 100
<212> TYPE: DNA
<213> ORGANISM: Artificial Sequence
<220> FEATURE:
<223> OTHER INFORMATION: PLUR-SMG-E31

<400> SEQUENCE: 89
ctcctctgac tgtaaccacg gagtgcgtgg ctaagcgcgt ctcgggtttc catattgctg    60
tgtgtgcatc caccatgtgc gcataggtag tccagaagcc                        100

<210> SEQ ID NO 90
<211> LENGTH: 80
<212> TYPE: DNA
<213> ORGANISM: Artificial Sequence
<220> FEATURE:
<223> OTHER INFORMATION: N40 ssDNA library construct
<220> FEATURE:
<221> NAME/KEY: misc_feature
<222> LOCATION: (21)..(60)
<223> OTHER INFORMATION: n is a, c, g, or t

<400> SEQUENCE: 90
ctcctctgac tgtaaccacg nnnnnnnnnn nnnnnnnnnn nnnnnnnnnn nnnnnnnnnn    60

```
gcataggtag tccagaagcc                                                    80

<210> SEQ ID NO 91
<211> LENGTH: 17
<212> TYPE: DNA
<213> ORGANISM: Artificial Sequence
<220> FEATURE:
<223> OTHER INFORMATION: M13 forward primer

<400> SEQUENCE: 91
gtaaaacgac ggccagt                                                       17

<210> SEQ ID NO 92
<211> LENGTH: 23
<212> TYPE: DNA
<213> ORGANISM: Artificial Sequence
<220> FEATURE:
<223> OTHER INFORMATION: M13 reverse primer

<400> SEQUENCE: 92
agcggataac aatttcacac agg                                                23
```